US009422607B2

(12) United States Patent
Walrafen et al.

(10) Patent No.: US 9,422,607 B2
(45) Date of Patent: Aug. 23, 2016

(54) METHOD FOR ANALYZING D4Z4 TANDEM REPEAT ARRAYS OF NUCLEIC ACID AND KIT THEREFORE

(75) Inventors: Pierre Walrafen, Montrouge (FR); Anne Vannier, Etrechy (FR); Aaron Bensimon, Antony (FR); Nicolas Levy, Marseilles (FR)

(73) Assignees: UNIVERSITE D'AIX-MARSEILLE, Marseilles (FR); ASSISTANCE PUBLIQUE DES HOPITAUX MARSEILLE, Marseilles (FR); GENOMIC VISION, Paris (FR)

( * ) Notice: Subject to any disclaimer, the term of this patent is extended or adjusted under 35 U.S.C. 154(b) by 628 days.

(21) Appl. No.: 13/120,063

(22) PCT Filed: Sep. 25, 2009
(Under 37 CFR 1.47)

(86) PCT No.: PCT/IB2009/007197
§ 371 (c)(1),
(2), (4) Date: Nov. 4, 2011

(87) PCT Pub. No.: WO2010/035140
PCT Pub. Date: Apr. 1, 2010

(65) Prior Publication Data
US 2013/0130924 A1    May 23, 2013

(30) Foreign Application Priority Data
Sep. 26, 2008   (EP) .................................... 08165310

(51) Int. Cl.
*C12Q 1/68*    (2006.01)
*C40B 30/04*   (2006.01)

(52) U.S. Cl.
CPC ........... *C12Q 1/6883* (2013.01); *C12Q 1/6834* (2013.01); *C12Q 2600/112* (2013.01); *C12Q 2600/154* (2013.01); *C12Q 2600/172* (2013.01); *C40B 30/04* (2013.01)

(58) Field of Classification Search
None
See application file for complete search history.

(56) References Cited

U.S. PATENT DOCUMENTS

2005/0054012 A1    3/2005  Tupler et al.

FOREIGN PATENT DOCUMENTS

WO    WO 2008/028931 A1    3/2008
WO    WO 2010/035140 A8    4/2010

OTHER PUBLICATIONS

Rossi et al, "The Facioscapulohumeral muscular dystrophy region on 4qter and the homologous locus on 10qter evolved independently under different evolutionary pressure," BMC Med. Genet. 2007, 8:8.*

(Continued)

*Primary Examiner* — Samuel Woolwine
*Assistant Examiner* — Kaijiang Zhang
(74) *Attorney, Agent, or Firm* — Oblon, McClelland, Maier & Neustadt, L.L.P.

(57) ABSTRACT

The present invention relates to a method for analyzing in vitro D4Z4 tandem repeat arrays of nucleic acid contained on nucleic acid representative of chromosomes, in particular on nucleic acid representative of Human chromosomes 4 and 10, and to a kit therefore. Said method is in particular suitable for determining the number of D4Z4 repeat units in said D4Z4 repeat arrays. Said method is based on stretching of nucleic acid and in particular on Molecular Combing and relies on the use of probes, especially nucleic acid probes, with a particular design. The invention also relates to a method for providing tools for the diagnosis of facioscapulohumeral muscular dystrophy (FSHD) and to a diagnostic kit therefore. The invention further relates to a method for identifying biochemical events and/or genetic in regions containing such tandem repeat arrays.

41 Claims, 10 Drawing Sheets

(56) References Cited

OTHER PUBLICATIONS

Michalet et al., "Dynamic Molecular Combing: Stretching the Whole Human Genome for High-Resolution Studies," *Science* 1997, 277:1518-1523.*

Caburet, Sandrine, et al., "Combining the genome for genomic instability", *Trends in Biotechnology*, 20(8): 344-350 (Aug. 2002).

Gad, Sophie, et al., "Color Bar Coding the BRCAI Gene on Combed DNA: A Useful Strategy for Detecting Large Gene Rearrangements", *Genes, Chromosomes & Cancer*, 31: 75-84 (2001).

Herrick, John, et al., "Quantifying single gene copy number by measuring fluorescent probe lengths on combed genomic DNA", *Proceedings of the National Academy of Sciences of the United States of America*, 97(1): 222-227 (Jan. 4, 2000).

International Search Report and Written Opinion, mailed Jan. 27, 2010, from International Application No. PCT/IB2009/007197 filed Sep. 25, 2009.

Lemmers, R.J.L.F., et al., "D4F104S1 deletion in facioscapulohumeral muscular dystrophy", *Neurology*, 61(2) 178-183 (Jul. 22, 2003).

Lemmers, R.J.L.F., et al., "Facioscapulohumeral muscular dystrophy is uniquely associated with one of the two variants of the 4q subtelomere", *Nature Genetics*, 32(2): 235-236 (Oct. 2002).

Pasero, Philippe, et al., "Single-molecule analysis reveals clustering and epigenetic regulation of replication origins at the yeast rDNA locus", *Genes and Development*, 16(19): 2479-2484 (Oct. 1, 2002).

Reisinger, Jürgen, et al., "Visualization of episomal and integrated Epstein-Barr virus DNA by fiber fluorescence in situ hybridization", *International Journal of Cancer*, 118(7): 1603-1608 (Apr. 2006).

Thomas, N.S.T., et al., "A large patient study confirming that facioscapulohumeral muscular dystrophy (FSHD) disease expression is almost exclusively associated with an FSHD locus located on a 4qA-defined 4qter subtelomere", *Journal of Medical Genetics*, 44(3): 215-218 (Mar. 2007).

* cited by examiner

4qA

4qB

10q(A)

METHOD FOR ANALYZING D4Z4 TANDEM REPEAT ARRAYS OF NUCLEIC ACID AND KIT THEREFORE

RELATED APPLICATIONS

This application is the U.S. National Stage of International Application No. PCT/IB2009/007197, filed on Sep. 25, 2009, published in English. This application claims priority under 35 U.S.C. §119 or 365 to European Application No. 08165310.7, filed Sep. 26, 2008.

The present invention relates to a method for analyzing in vitro D4Z4 tandem repeat arrays of nucleic acid, including for analysing larger regions comprising said repeats or surrounding said repeats, contained on nucleic acid representative of chromosomes, and in particular for determining in vitro the number of D4Z4 repeat units in said D4Z4 tandem repeat arrays. Said method comprises the use of probes, especially nucleic acid probes, with a particular design.

The invention also relates to a method for providing tools for the diagnosis of facioscapulohumeral muscular dystrophy (FSHD) and to a diagnostic kit therefore.

The invention further relates to a method for identifying biochemical and/or genetic events in regions comprising such tandem repeat arrays, or in said tandem repeat arrays.

The invention also relates to a kit comprising the probes used to carry out a method of the invention and to a composition comprising said probes in solution.

The present invention is based on stretching of nucleic acid and in particular on stretching obtained by Molecular Combing. Stretching nucleic acid, in particular genomic DNA provides immobilized nucleic acids in linear and parallel strands, and is preferably performed with a controlled stretching factor, on an appropriate surface (e.g. surface-treated glass slides). After stretching, it is possible to bind and especially to hybridize sequence-specific probes detectable for example by fluorescence microscopy (Lebofsky and Bensimon, 2006). Thus, the physical cartography of a locus may be directly visualized, on a single molecule level. The length of the fluorescent signals and/or their number, and their spacing on the slide provides a direct reading of the size and relative spacing of the probes. In the case of a tandem repeat, the length of the signal for a probe hybridizing on the repeated sequence reflects the number of repeat units. During the sample preparation for stretching, in particular according to Molecular Combing technology, genomic DNA is broken at random locations. Thus, the analyzed DNA molecules are of variable length, with an average of about 300 kb, the longest molecules reaching several megabases.

Molecular combing technology has been disclosed in various patents and publications, including in U.S. Pat. No. 6,303,296, WO9818959, WO0073503, US2006257910, US2004033510, U.S. Pat. No. 6,130,044, U.S. Pat. No. 6,225,055, U.S. Pat. No. 6,054,327, WO2008028931 and in Michalet et al., 1997; Herrick et al., 2000; Conti et al., 2001; Gad et al., 2001; Lebofsky and Bensimon, 2005; Lebofsky and Bensimon, 2006

The invention concerns in particular application of the disclosed methods and products in the field of detection of FSHD. For a recent review on the FSHD pathology, one can refer to (van der Maarel et al., 2007 and references therein. FSHD is the third most frequent muscular dystrophy (incidence 1/20000. Clinically, the presentation includes symptoms such as weakness of the scapula fixators, asymmetrical facial weakness, pelvic girdle weakness, abdominal, upper arm and/or foot extensor muscles weaknesses, among other features. It is an autosomal dominant genetic disease, with sporadic (non-inherited) cases representing between 10% and 30% of new cases.

The FSHD locus was mapped at chromosome 4q35. It was shown that a contraction of a tandem repeat array is a genetic marker of the susceptibility to the disease or to the occurrence thereof. The repeated sequence unit, termed D4Z4, is 3.3 kb long, and is present, among other loci, in the telomeric region of the long arm of chromosome 4. Individuals with more than 12 repeat units on both chromosomes 4q do not carry FSHD, whereas individuals with shorter repeat arrays on one or two alleles may carry FSHD. It was further shown that among carriers of FSHD-size repeat arrays, the disease was exclusively associated with a specific haplotype of chromosome 4q. Two haplotypes of 4q, occurring with roughly 50% frequency each, 4qA and 4qB, differ in the sequences immediately telomeric relatively to the repeat array. Only those individuals with a short (<12 repeat units) repeat array on a 4qA chromosome are susceptible to the disease.

Sequences similar to the D4Z4 sequences found on chromosome 4q are present in several other loci, with sequence similarities up to 90%. The similarity between the telomeric regions of 4q and 10q chromosomes is most striking. Indeed, 10q chromosomes also bear a D4Z4 repeat array, a ~40 kb sequence upstream of the array highly similar to the equivalent location on 4q, and a telomeric end identical to the 4qA extremity. The D4Z4 sequence units on 10q are ~98% similar to those on 4q (Cacurri et al, 1998). Other repeat arrays with sequences similar to D4Z4 are located in particular on chromosome Y.

Probably more than 95% of patients with FSHD phenotype carry a short repeat array on a 4qA chromosome. However, among individuals with such an allele, penetrance of the disease is not full and clinical severity is very variable (Van der Maarel et al., 2007). For one thing, the size of the repeat array seems to be negatively correlated with severity and penetrance, with very short (<4 repeat units) arrays being associated with the most severe presentations, and longer (8-12 repeat units) arrays with milder to normal phenotype (Van der Maarel et al., 2007 and references therein). However, other factors are certainly involved. Genetic factors may include sequence variations and/or rearrangements on the pathogenic allele, or on homologous chromosomes, or other genetic determinants. For example, individuals with a specific SSLP (simple sequence length polymorphism) upstream of the repeat array are found to be healthy, although they carry an FSHD-sized, 4qA alleles (Lemmers et al., 2007). Other rearrangements occur in this region, such as deletions of various sizes of the sequences centromeric to the repeat array, which may or may not include some of the repeats. In such cases, the presence of an FSHD-size allele on a 4qA chromosome still translates in an FSHD phenotype (Lemmers et al., 2003; Deak et al., 2007).

Although clinical diagnosis is fairly reliable, genetic diagnosis of FSHD is a necessity to allow for relevant genetic counseling. Beside the fairly complex genetic description for a single-gene disease, other challenging factors for the genetic diagnosis of FSHD are the occurrence of somatic mosaicism (van der Maarel et al, 2000), an important parameter for genetic counseling, and of recombination between 4q and 10q regions (Lemmers et al, 1998). These recombination events lead to diagnostic failures since they translate into 4q-carried D4Z4 repeat units with 10q sequences and only the location and number of repeat units are relevant to diagnostics, not their sequence. Nonetheless, most FSHD tests in routine setups distinguish 4q- and 10q-D4Z4 repeat units by their sequence rather than their location.

Indeed, the most common setup for genetic tests for FSHD relies on restriction enzyme digestions of genomic DNA and fragment size analysis by electrophoresis and southern blotting. A common setup is to visualize the size of the entire repeat array with a probe recognizing all 4q and 10q alleles and in the presence of an FSHD-size allele to assess its location with enzymes digesting either 4q- or 10q-D4Z4 sequences specifically, based on their sequence differences. Probes specific for 4qA or 4qB may be used to confirm the haplotype for a short 4q allele (Ehrlich et al., 2006). Also, since the probe used to visualize all 4q and 10q alleles hybridizes in a region that is sometimes deleted, it may be necessary to confirm the absence of an FSHD-allele by using a probe hybridizing in the repeat array.

This family of tests is highly time-consuming, requiring sometimes several rounds of pulse-field gel electrophoresis and in all cases southern blotting, implying manipulation of radioactivity, long migration and/or exposure time. More importantly, the results are often ambiguous, especially for borderline-size alleles or in the case of recombination events. Moreover, the detection of mosaicism is unreliable and its sensitivity is low (at best a mosaicism may be detected if it is carried by 10%-30% of cells) (van der Maarel et al, 2000). Also, in some cases the deletion of the region centromeric to the repeat array may not be suspected and the failure to detect an FSHD-allele in such a case may lead to the erroneous conclusion that there is no such allele.

Other types of tests have been suggested to be able to overcome these limitations. A non-radioactive test has been described, but it bears all the other drawbacks of the typical southern blot tests, with a considerably reduced sensitivity and specificity (Kekou et al., 2005). A long-range PCR-based test, presumably capable of determining the size of 4q-located repeat arrays up to 5-7 repeat units was also described (Goto et al., 2006). This test has several advantages, mainly in terms of time, cost, and ease of execution, over southern blot tests. However, it suffers major drawbacks, which include inability to detect repeat arrays with more than 7 repeat units, to distinguish 4qA from 4qB chromosomes, to account for mosaicism or to detect variant cases with, for example, deletion of sequences upstream of the repeat array (Lemmers et al., 2006). Besides, it relies on a single nucleotide divergence between 4q and 10q sequences to distinguish 4q- and 10q-located arrays, making it vulnerable to point mutations.

The method of the invention enables to assess the sizes and haplotypes of D4Z4 repeat arrays reliably, with single-repeat resolution, in a time- and cost-effective fashion, and with none of the constraints of manipulating radioactivity. This method should also be highly sensitive to mosaicism and account for 4q/10q recombination as well as other variant cases. The method of the invention also enables to determine further biochemical or genetic events in this array.

In the context of the invention, molecular combing or other nucleic acid stretching methods, allowing direct visualization of stretched nucleic acid, may be successfully applied to the determination of D4Z4 repeat arrays and possibly to the diagnosis of FSHD, which was never suggested before.

More generally, the present invention is the first application of Molecular Combing to a case of copy number polymorphism for tandem repeat arrays, where the length of the repeat probe is measured, rather than the repetition of a motif of probes.

DETAILED DESCRIPTION OF THE INVENTION

The present invention relates to a method for analysing in vitro D4Z4 tandem repeat arrays of nucleic acid including for analysing larger regions comprising said repeats or surrounding said repeats, contained on nucleic acid representative of chromosomes, in particular nucleic acid representative of Human chromosomes 4 and 10, and optionally nucleic acid of chromosomes Y. Said method is especially suitable for determining the number of D4Z4 repeat units in said D4Z4 repeat arrays. Said method comprises a hybridization step of nucleic acid representative of said chromosomes with at least the following probes:

a probe or a set of probes which is (are) specific for D4Z4 tandem repeat array(s);

one probe or one or several set(s) of probes which enable(s) to distinguish one chromosome from another, in particular chromosome 4 (4q) from chromosome 10 (10q); and one probe or one or several set(s) of probes which enable(s) to distinguish one haplotype from another, in particular to distinguish the qA haplotype from the qB haplotype; and optionally, a probe or one or several set(s) of probes which enable(s) to distinguish chromosome Y from chromosome 4 and/or from chromosome 10.

In a particular embodiment, the D4Z4 repeat arrays are tandem repeat arrays which are found on human chromosomes 4, 10 and/or Y.

By "analysing D4Z4 tandem repeat arrays" or "analysing organization of D4Z4 repeat arrays" it is meant herein in particular:

determining the number of D4Z4 repeat units in said D4Z4 repeat arrays; and/or determining the orientation of the D4Z4 repeat units in said D4Z4 repeat arrays;

detecting and/or analysing rearrangements (in particular deletions and/or insertions of nucleotides sequences) in said D4Z4 repeat arrays and/or in regions found in the vicinity or in regions adjacent or essentially adjacent to said D4Z4 repeat arrays; and/or analysing methylation in particular CpG methylation; and/or analysing biochemical events, in particular replication and/or transcription and/or transcription factor binding and/or binding of other DNA binding proteins, in said D4Z4 repeat arrays and/or in regions in the vicinity or in regions adjacent or essentially adjacent to said D4Z4 repeat arrays.

By "D4Z4 repeat unit" it is meant herein any sequence termed D4Z4, which is present as a repeated sequence on a human chromosome, especially in a tandem repeat array in particular on the long arm of chromosomes 4 and 10 and optionally on chromosome Y. Said D4Z4 repeat unit is generally 3.3 kb in length in the case of the D4Z4 repeat array of chromosome 4. The nucleotide composition of the D4Z4 repeat unit is described in Hewitt et al., 1994 and Cacurri et al, 1998.

The term "nucleic acid" and in particular "nucleic acid representative of chromosomes" as used herein designates one or several molecules of any type of nucleic acid capable of being attached to and stretched on a support as defined herein, and more particularly stretched by using molecular combing technology; nucleic acid molecules include DNA (in particular genomic DNA, especially chromosomic DNA, or cDNA) and RNA (in particular mRNA). A nucleic acid molecule can be single-stranded or double-stranded but is preferably.

"Nucleic acid representative of a given chromosome" means that said nucleic acid contains the totality of the genetic information or the essential information with respect to the purpose of the invention, which is present on said chrosomome. In particular, it is chromosomic DNA.

In a particular embodiment, the nucleic acid sample used for stretching is genomic DNA, in particular total genomic DNA or more preferably chromosomic genomic DNA (nuclear genomic DNA), and/or fragments thereof. The term "nucleic acid" is in particular used herein to designate a nucleic acid representative of one or several chromosome(s) and/or of one or several fragment(s) of chromosomes. Said fragments can be of any size, the longest molecules reaching several megabases. Said fragment are generally comprised between 5 and 2000 kb or 10 and 2000 kb, preferably between 5 and 1000 kb or 5 and 500 kb, and more preferably between 20 and 500 kb and are in average of about 300 kb.

The nucleic acid sample used in the method of the invention can be obtained from a biological fluid or from a tissue of biological origin, said sample or tissue being isolated for example from a human (also called patient herein) or a non human mammalian.

As defined herein, a probe is a polynucleotide, a nucleic acid/polypeptide hybrid or a polypeptide, which has the capacity to hybridize to nucleic acid representative of chromosomes as defined herein, in particular to RNA and DNA. This term encompasses RNA (in particular mRNA) and DNA (in particular cDNA or genomic DNA) molecules, peptide nuclear acid (PNA), and protein domains.

A polynucleotide probe or a nucleic acid hybrid probe generally comprises or consists of at least 100, 300, 500 nucleotides, preferably at least 700, 800 or 900 nucleotides, and more preferably at least 1, 2, 3, 4 or 5 kb. For example probes of 1, 2, 3, 4, 5, 6, 7, 8, 9, 10, 11, 12, 13, 14, 15 kb or more than 15 kb, in particular 30, 50 or 100 kb can be used. In a particular embodiment, the length of the probes used is ranging from 0.5 to 50 kb, preferably from 1 to 30 kb and more preferably from 1 to 10 kb, from 4 to 20 kb, from 4 to 10 kb, or from 5 to 10 kb.

As used herein, the "sequence" of a probe, when the probe is a polypeptide, should be understood as the sequence to which said polypeptide specifically binds. Thus, in the paragraphs relating to the probes in the present application, which are applicable to polypeptidic probes, the reference to "hybridization" in this particular context should rather be understood as "binding" (for convenience "hybridization" rather than "binding" is used herein). A polypeptide probe generally specifically binds to a sequence of at least 6 nucleotides, and more preferably at least 10, 15, 20 nucleotides. A polypeptide probe as defined herein can be in particular any nucleic acid binding domain (especially a DNA binding domain) of a protein with sequence specificity (i.e. which specifically binds to particular nucleic acid regions). For example, said polypeptide probe can be a restriction enzyme which has been modified in order that in does not cleave nucleic acid (in particular DNA), a transcription factor or the DNA binding domain of a meganuclease.

In a particular embodiment, a probe of the invention hybridizes along its whole length with a particular region of nucleic acid, in particular with chromosomes 4, 10 or Y and/or with the chromosomes of the qA or qB haplotype.

By "probe specific for D4Z4 repeat arrays" or "repeat probe", it is meant herein a probe which hybridizes specifically with D4Z4 repeat arrays, i.e., a probe which hybridizes with D4Z4 repeat arrays, and does not or does not significantly hybridize with other nucleic acid regions in chromosomes 4, 10, and Y and thus, which enables detection of the D4Z4 repeat arrays contained on the nucleic acid sample. Said probe hybridizes at least with the D4Z4 repeat arrays which are found on human chromosomes 4 and more preferably also hybridizes with the D4Z4 repeat arrays which are found on human chromosomes 10. The repeat probes are preferably designed is such a way that at least one of them hybridizes with any D4Z4 repeat array, i.e. in particular with D4Z4 repeat arrays which are located on chromosomes 4, 10 and Y. In a preferred embodiment, said repeat probes may be designed to hybridize with the D4Z4 repeat unit and has the length of said D4Z4 repeat unit.

The probe(s) which is (are) specific for D4Z4 repeat arrays are called "repeat probe(s)". The other probes are called "location probes" or "localization probes" because they enable determination of the position of D4Z4 repeat arrays, i.e. localization of D4Z4 repeat arrays on particular chromosomes, for example on chromosomes 4, 10 or Y and/or on chromosomes of the qA or qB haplotype.

Thus, the location probes used hybridize with at least one region of nucleic acid located outside a D4Z4 repeat array and preferably hybridize only with regions of nucleic acid located outside a D4Z4 repeat array.

In a particular embodiment, the sequence of a probe is at least 99% complementary, i.e., at least 99% identical (for example 99.5%, 99.9% or 100% identical) or at least 99% similar (for example 99.5%, 99.9% or 100% similar) to the sequence of a portion of one strand of the target nucleic acid to which it must hybridize. For example, as described hereafter, in one embodiment, the repeat probe or at least one of the repeat probes is 99.9% (for example 99.5%, 99.9% or 100%) complementary/identical or 99.9% (for example 99.5%, 99.9% or 100%) similar to the sequence of the D4Z4 repeat unit which is located on one strand of a chromosome 4 or to the sequence of a portion of said D4Z4 repeat unit.

The term "complementary sequence" in the context of the invention means "complementary" and "reverse" or "inverse" sequence, i.e. the sequence of a DNA strand that would bind by Watson-Crick interaction to another DNA strand comprising or consisting of said sequence.

By "a portion of" a particular region, it is meant herein consecutive nucleotides of the sequence of said particular region. A portion according to the invention can comprise or consist of at least 15 or 20 consecutive nucleotides, preferably at least 100, 200, 300, 500 or 700 consecutive nucleotides, and more preferably at least 1, 2, 3, 4 or 5 consecutive kilobases (kb) of said particular region. For example, a portion can comprise or consist of 1, 2, 3, 4, 5, 6, 7, 8, 9, 10, 11, 12, 13, 14, 15 consecutive kb of said particular region.

In a particular embodiment, the probe used or at least one of the probes used is a nucleotide variant of the probe showing a sequence complementarity or similarity of 100% to a portion of one strand of the target nucleic acid. The sequence of said variant can have at least 70, 80, 85, 90 or 95% complementarity or similarity to the sequence of a portion of one strand of the target nucleic acid. Said variant can in particular differ from the probe which is 100% identical or complementary by 1 to 20, preferably by 1 to 10, nucleotide deletion(s), insertion(s) and/or more preferably substitution(s), in particular by, 1, 2, 3, 4, 5, 6, 7, 8, 9 or 10 nucleotide deletion(s), insertion(s) and/or more preferably substitution(s) in the original nucleotide sequence. In a particular embodiment, the variant keeps the capacity to hybridize, in particular to specifically hybridize, to the sequence of the nucleic acid target, similarly to the probe that is 100% identical or 100% complementary to a sequence of the nucleic acid target (in particular in the hybridization conditions defined herein).

In a particular embodiment of the invention, the probes or one or several probes used to carry out the invention, in particular the repeat probe(s), are labelled. In general, the repeat probe(s) or at least one of the repeat probes is (are) labelled with one or several label(s) (for example biotin) and the localization probes are labelled with at least one different label (for example digoxygenin). Said probes can be labelled as defined herein and as described in patent application WO 2008/028931, which is incorporated herein by reference.

A set of probes as used herein consists of at least two probes. For example, said set of probes can consist of 2 to 15 probes (2, 3, 4, 5, 6, 7, 8, 9, 10, 11, 12, 13, 14 or 15), preferably 2 to 10 probes or 2 to 6 probes and more preferably 2 to 4 or 2 to 5 probes. The number of probes in a set does usually not exceed 10, 20 or 30 probes; a set of probes preferably consists of 5, 6, 7, 8, 9 or 10 probes at the most.

In a particular embodiment, the method of the invention comprises or consists of the following steps:

a) providing a support on a nucleic acid sample comprising nucleic acid representative of chromosomes has been previously stretched in linear and parallel strands and hybridizing said nucleic acid with the different probes;

b) detecting the hybridization signals corresponding to the different probes; and c) analysing organization of D4Z4 repeat arrays on nucleic acid representative of chromosomes, in particular determining the number of D4Z4 repeat units in said D4Z4 repeat arrays.

The nucleic acid sample is generally stretched on a support in linear and parallel strands using a controlled stretching factor. By stretching factor it is meant herein the conversion factor allowing to connect physical distances measured on the stretched nucleic acid to the sequence length of said nucleic acid. Such a factor may be expressed as X kb/µm, for example 2 kb/µm. By controlled stretching factor it is meant herein a technique for which the stretching factor is sufficiently constant and uniform to allow reliable deduction of the sequence length of a hybridization signal from the measured physical length, without the use of calibration probes on the tested sample.

Stretching of the nucleic acid sample can be in particular performed using a molecular combing technique. Molecular combing can be performed according to published methods, in particular as described in WO 95/22056, WO 95/21939, WO 2008/028931 and in U.S. Pat. No. 6,303,296 (which is incorporated herein by reference) and Lebofsky and Bensimon, 2005. Prior to nucleic acid stretching, nucleic acid manipulation generally causes the strand(s) of nucleic acid to break in random locations.

Other DNA stretching methods may be used as an alternative to Molecular Combing. These methods include, for example:

methods based on the extraction of DNA with detergent and/or high salt concentration, combined or not with the incubation with an intercalating agent and/or UV-light, derived from the methods termed ECF-FISH (extended chromatin fibers-fluorescent in situ hybridization), Halo preparation, and other methods described in (Heng et al., 1992; Haaf and Ward, 1994; Wiegant et al., 1992m Florijn et al., 1995; Vandraager et al., 1998, Raap, 1998, Palotie et al., 1996, Fransz et al., 1996); and methods based on the stretching of DNA through the action of a hydrodynamic flow or through mechanical traction on the DNA molecules, by capillarity, gravity or mechanical force, possibly in a micrometer- or nanometer-scale device, the DNA being or not immobilized on a solid support, derived from methods termed DIRVISH (direct visual hybridization), optical mapping, and other methods described in Parra and Windle, 1993; Raap, 1998; Heiskanen et al., 1994; Heiskanen et al., 1995; Heiskanen et al., 1996, Mann et al., 1996, Schwartz et al., 1993; Samad et al., 1995, Jing et al., 1998; Dimalanta et al., Palotie et al., 1996, Larson et al., 2006).

Some adaptations, accessible to the man skilled in the art, may be necessary to perform the methods described herein using these stretching methods. For most of these methods, the stretching factor is not controlled, and it is therefore necessary to include a means of calibration in order to connect physical distances on the stretched molecules and sequence length. Such a calibration method may be e.g. including a probe (or several probes) of known constant sequence length(s), whose measure(s) will indicate the distance/sequence length ratio. This (these) probe may be one of the probes (include several probes) described in the probe sets herein, e.g. one of the chromosome 4- or chromosome 10-specific probes, or also the "common" probe to 4q and 10q in the region immediately upstream to the D4Z4 repeat array described in the examples herein. Also, the resolution, measurement precision, number of usable labels, may differ in these methods from molecular combing, which may imply modifying the probe design. Examples of how this may be achieved are given in the examples section.

The support on which nucleic acid has been stretched can be any appropriate support, in particular any support appropriate for molecular combing. The support may consist, at least at the surface, of an organic or inorganic polymer, a metal especially gold, a metal oxide or sulfide, a semiconductor element or an oxide of a semiconductor element, such as silicon oxide or a combination thereof, such as glass or a ceramic. There may be mentioned more particularly glass, surface oxidized silicon, graphite, mica and molybdenum sulfide.

A "support" as used herein encompasses a single support such as a slide, beads, especially polymer beads, but also any form such as a bar, a fiber or a structured support, and also particles, whether it be powders, especially silica powders, which can moreover be made magnetic, fluorescent or colored. The support is advantageously a flat surface, for example a coverslip. Preferably, the support has little or no fluorescence.

The nucleic acid sample can be contacted with the different probes before and/or after being stretched on the support. However, the step of stretching is generally performed before the step of hybridization with the different probes.

If necessary, in particular when the nucleic acid molecules of the sample are double-stranded, hybridization is preceded by a step of denaturation of the nucleic acid and/or of the probes. Thus, in a particular embodiment of the invention, nucleic acid is first stretched on the support and then denaturated (if necessary to provide single-stranded nucleic acid) and hybridized with the different probes. In another particular embodiment, nucleic acid is first denaturated (if necessary) and hybridized with the different probes before being stretched on the support.

As used herein, the term "hybridization" or "hybridize with" encompasses high stringency hybridization; in several wash steps all unhybridized probes and the majority of partially hybridized probes are washed away. Hybridization and washing conditions used herein preferably permit nucleotide sequences which are at least 60% complementary to each other to remain hybridized to each other. Preferably, the conditions are such that sequences which are at least about 70%, more preferably at least about 80%, even more preferably at least about 85%, 90%, 95%, 98% complementary or 100% complementary to each other typically remain hybridized to each other, i.e., form stable hybrids for the purpose of detection.

Stringent conditions are known to the person skilled in the art. Examples of such conditions are disclosed in Cell Biology, a Laboratory Handbook, $3^{rd}$ ed., Part F, Elsevier Academic Press, 2006.

Conditions of high stringency hybridization correspond in particular to temperature and ionic strength conditions allowing the maintenance of the hybridization between two single-stranded DNA molecules which share 100% sequence identity. By way of illustration, high stringency hybridization conditions in the context of the invention are the following:

1) hybridization for 20 hours a 37° C. in hybridization buffer (50% formamide, 2×SSC, 0.5% SDS, 0.5% Sarcosyl, 10 mM NaCl, 30% Block-aid) with 10 µg herring sperm DNA and 2.5 µg Human Cot-1 DNA, followed by 3 washes of 5 minutes at 20° C. in 2×SSC+50% formamide and 3 washes of 5 minutes at 20° C. in 2×SSC.

These hybridization conditions can be adapted by the person skilled in the art according to the protocols published in Lebofsky and Bensimon, 2006, Lebofsky, et al., 2005; Conti et al., 2001; Gad et al., 2001; Herrick et al., 2000; Michael et al., 1997.

In a particular embodiment of the invention, step b) further includes transcription of the hybridization signals into codes. Examples of codes as described in patent application WO2008/028931, which is incorporated herein by reference.

In a particular embodiment of the method of the invention, step b) further includes obtaining, for each nucleic acid of the sample which shows at least one hybridization signal corresponding to a repeat probe, information corresponding to one or a combination of the following categories: (1) typing of the hybridization signals corresponding to localization probes, (2) the length of one or several hybridization signals, (3) the position of one or several type(s) of hybridization signals relative to a D4Z4 repeat array, and (4) the distance between two hybridization signals.

By "obtaining information", it is meant achieving some steps (one or several) to obtain said information.

"Typing" hybridization signals consists in associating a particular hybridization signal corresponding to localization probes or a succession of hybridization signals corresponding to localization probes with a particular chromosome or haplotype. In particular said typing can consist in determining whether the presence of a particular hybridization signal or a succession of hybridization signals belongs to a signature of a chromosome or haplotype as defined herein.

Determining "the position of one or several type(s) of hybridization signals relative to a D4Z4 repeat array" can consist in assessing whether said hybridization signals of a strand of nucleic acid are located in a centromeric or in a telomeric region, in particular whether they are immediately centromeric or telomeric relatively to the hybridization signal(s) corresponding to a D4Z4 repeat array which is(are) detected on said strand of nucleic acid. Additionally or alternatively, this expression can also mean measuring the distance separating one or several hybridization signals corresponding to localization probe(s) and a the hybridization signal(s) corresponding to a D4Z4 repeat array which is(are) detected on the same strand of nucleic acid.

As used herein, the term "centromeric to" (respectively "telomeric to") or "centromeric relatively to" (respectively "telomeric relatively to") means closer to the centromere on the same chromosome arm (respectively closer to the telomere on the same chromosome arm).

As used herein, the term "upstream" (respectively "downstream") means closer to the telomere of the "p" arm (i.e. the short arm) on the same chromosome (respectively closer to the telomere of the "q" arm (i.e. the long arm) on the same chromosome). With these definitions, on the long arm of a given chromosome, "upstream" and "centromeric to" have the same meaning and "downstream" and "telomeric to" have the same meaning.

As used herein, the term "immediately" centromeric (respectively telomeric) means (i) adjacent or essentially adjacent and (ii) centromeric (respectively telomeric). Few nucleotides (for example 1, 2, 3, 4, 5, 6, 7, 8, 9 or 10) or few tens of nucleotides, in particular 10 to 100 (for example 10, 20, 30, 40, 50, 60, 70, 80, 90 or 100) nucleotides can separate two regions which are "essentially adjacent".

The term "distance between two hybridization signals" can designate the distance between any hybridization signal detected on a strand of nucleic acid and any other hybridization signal detected on the same nucleic acid strand, and in particular the distance between two consecutive hybridization signals. With the molecular combing method, two hybridization signals are considered as being on the same strand of nucleic acid if they are aligned and separated by less than 500 Mb. Each of these two hybridization signals can correspond to the same of to different probes, which can independently be chosen between a repeat probe and any type of localization probes.

By "the distance between a first hybridization signal and another (for example a last) hybridization signal", it is meant herein the distance (i) between the beginning (or respectively the end) of said first hybridization signal and the end (or respectively the beginning) of said other hybridization signal or (ii) between the beginning (or respectively the end) of said first hybridization signal and the beginning (or respectively the end) of said other hybridization signal.

In a particular embodiment of the method of the invention, the step of detecting the hybridization signals corresponding to the different probes (step b) further includes (i) measuring the length of every hybridization signal corresponding to a repeat probe and/or (ii) measuring, for every detected D4Z4 repeat array, the distance between the first hybridization signal corresponding to a repeat probe and the last hybridization signal corresponding to a repeat probe on the same nucleic acid strand. In particular, the length of every hybridization signal corresponding to a repeat probe hybridizing, along its whole length, with the whole sequence of the repeat unit of a D4Z4 repeat array can be measured, as described hereafter. The number of D4Z4 repeat units in a D4Z4 repeat array can easily be deduced from the length(s) measured, which optionally requires one or several correction factor(s).

Alternatively, the number of D4Z4 repeat units in a D4Z4 repeat array can be determined by simply counting the number of hybridization signals corresponding to the repeat probe or to a repeat probe as described hereafter.

In a particular embodiment, step b) of the method of the invention includes the use of software to display digital images of the hybridization signals and to manually measure the lengths of the hybridization signals and/or the distances between successive hybridization signals.

In a particular embodiment, step b) of the method of the invention includes the use of image analysis software to automatically detect hybridization signals and measure the lengths of the hybridization signals and/or the distances between successive hybridization signals. Such software may comprise signal detection algorithms such as those described in Berlemont et al., 2007, Berlemont et al., 2007a, Berlemont et al., 2007b and in patent US06/911,797.

In a particular embodiment, step b) of the method of the invention further includes establishing a histogram (i.e., a graphical representation) of the lengths of the hybridization signals measured, in particular a histogram of the lengths of the hybridization signals corresponding to a repeat probe and/or establishing a histogram of the distances measured between two hybridization signals corresponding to a repeat probe.

In a particular embodiment, step b) of the method of the invention further includes a step of determining the standard deviation of the measurements, in particular as described in the example part of the present application.

In a particular embodiment, step c) of the method of the invention includes the use of software, in particular of statistical analysis software.

In a particular embodiment, step c) of the method of the invention comprises or consists in identifying the D4Z4 repeat arrays which are located on a chromosome 4qA (organization of these repeat arrays being analyzed by the method of the invention). Step c) can further include the step of identifying the D4Z4 repeat arrays which are located on a nucleic acid derived from a non-4qA chromosome, i.e. in particular, on a chromosome 4qB, on a chromosome 10, and/or on a chromosome Y, and determining the number of D4Z4 repeat units in each of these repeat arrays.

In a particular embodiment of the invention, several measurements (for example 5, 10, 20, 30, 40 or 50) of the length of the D4Z4 repeat array are performed for the same allele of a nucleic acid sample.

In a particular embodiment of the invention, several measurements of the number of D4Z4 repeat units are performed for every 4qA alleles, and for every 4qB alleles contained in the nucleic acid sample of a patient.

Therefore, in a particular embodiment, the nucleic acid sample used corresponds to at least about 10 copies, preferably at least 30 copies and more preferably at least 50 or 60 copies, for example 25-500, 25-300 or 25-100 copies of a genome and in particular of chromosomic DNA which have been stretched on an appropriate support. It should be noted that although a genome, in particular a human genome usually consists of pairs of chromosomes (23 pairs for a human genome), the stretched nucleic acid sample is not always homogeneous. Indeed, since nucleic acid is generally purified, in particular before being stretched, it often happens that for each copy of a genome, only the nucleic acid representative of one chromosome (allele) instead of the nucleic acid representative of a pair of chromosomes is stretched on the appropriate support.

In a particular embodiment, the criteria for interpretation of the data obtained are as described in the example part of the present application and should be understood as being applicable for various embodiments.

In a particular embodiment of the invention, the probe or set(s) of probes which enable(s) to distinguish chromosome 4 from chromosome 10 comprises or consists of:

(i) a probe which is specific for chromosome 4 or (ii) a probe or one or several set(s) of probes hybridizing with chromosome 4, said probe or each of said set(s) of probes being chosen in such a way that upon hybridization to chromosome 4, the position of the probes, one compared to the others, forms a signature which is specific for chromosome 4 and/or (i) a probe which is specific for chromosome 10 or (ii) a probe or one or several set(s) of probes hybridizing with chromosome 10, said probe or each of said set(s) of probes being chosen in such a way that upon hybridization to chromosome 10, the position of the probes, one compared to the others, forms a signature which is specific for chromosome 10.

In a particular embodiment of the invention, if present, the probe or the set(s) of probes which enable(s) to distinguish chromosome Y from chromosome 4 and/or from chromosome 10, comprises or consists of (i) a probe which is specific for chromosome Y or (ii) a probe or one or several set(s) of probes hybridizing with chromosome Y, said probe or each of said set(s) of probes being chosen in such a way that upon hybridization to chromosome Y, the position of the probes, one compared to the others, forms a signature which is specific for chromosome Y.

The "signature" of a particular domain (especially of a chromosome) results from a hybridization pattern obtained with at least one probe or with various different probes, which pattern is specific and defined by the size of the spacing (gap) between two consecutive probes, when hybridized, and/or by a succession of probes and in particular of different probes. As illustrated in the example part of the present application, such a signature can consist, for example, of a succession of several probes (for example 4 probes) of the same length (l) which are interspaced by gaps of the same length, the length of these gaps being equal to the length (l) of the probes or of a different size.

By "different probes", it is meant herein probes of different sizes and/or of different sequences and/or labelled with at least one different label.

Detection of the signature of a domain of interest on a nucleic acid indicates the presence of said domain of interest on said nucleic acid. Hence, detection of a signature specific for either chromosome 4 or 10 or Y or specific for the qA or qB haplotype on a nucleic acid comprising a D4Z4 repeat array indicates that said nucleic acid is respectively a chromosome 4, 10 or Y or a chromosome of the qA or qB haplotype or a fragment of said chromosome and thus that said D4Z4 repeat array is located respectively on chromosome 4, 10 or Y or on a chromosome of the qA or qB haplotype.

As used herein, the term (i) "specific for chromosome 4", (ii) "specific for chromosome 10" or "specific for chromosome Y", means respectively (i) specific for chromosome 4 with respect to chromosome 10 and also with respect to chromosome Y, (ii) specific for chromosome 10 with respect to chromosome 4, and also with respect to chromosome Y, and (iii) specific for chromosome Y with respect to chromosome 4 and with respect to chromosome 10.

By "a probe specific for chromosome 4 (or chromosome 10) with respect to chromosome 10 (chromosome 4 respectively) and also with respect to chromosome Y" it is meant herein a probe hybridizing with chromosome 4 (chromosome 10 respectively) and not with chromosome 10 (chromosome 4 respectively), and also not hybridizing with chromosome Y. Similarly, "a probe specific for chromosome Y with respect to chromosome 4 and with respect to chromosome 10" is a probe hybridizing with chromosome Y and not with chromosome 4 and not with chromosome 10.

As used herein, the term "a signature specific for chromosome 4 (or chromosome 10) with respect to chromosome 10 (chromosome 4 respectively) and also with respect to chromosome Y" means a signature, which upon hybridization of the probe or set of probes forming said signature, is found on chromosome 4 (chromosome 10 respectively) and not on chromosome 10 (chromosome 4 respectively) and not on chromosome Y. Similarly, "a signature for chromosome Y with respect to chromosome 4 and with respect to chromosome 10" is a signature, which upon hybridization of the probe or set of probes forming said signature, is found on chromosome Y and not on chromosome 4 and not on chromosome 10.

In a particular embodiment of the invention, one probe or one or several set(s) of probes which enable(s) to distinguish the qA haplotype from the qB haplotype comprises or consists of:

(i) a probe which is specific for the qA haplotype or (ii) a probe or one or several set(s) of probes hybridizing with chromosomes of the qA haplotype, said probe or each of said set(s) of probes being chosen in such a way that upon hybridization to said chromosomes, the position of the probes, one compared to the others, forms a signature which is specific for the qA haplotype; and/or (i) a probe which is specific for the qB haplotype or (ii) a probe or one or several set(s) of probes hybridizing with chromosomes of the qB haplotype, said probe or each of said set(s) of probes being chosen in such a way that upon hybridization to said chromosomes, the position of the probes, one compared to the others, forms a signature which is specific for the qB haplotype.

A "probe which is specific for the qA haplotype" (or for the qB haplotype) means herein a probe which hybridizes only to chromosomes of the qA haplotype (or chromosomes of the qB haplotype respectively), i.e. a probe which hybridizes with chromosomes of the qA haplotype (chromosomes of the qB haplotype respectively) and not with chromosomes of the qB haplotype (chromosomes of the qA haplotype respectively).

A "signature specific for the qA haplotype" (or for the qB haplotype) means a signature which upon hybridization of the probe or set of probes forming said signature, is found on chromosomes of the qA haplotype (the qB haplotype respectively) and not on chromosomes of the qB haplotype (the qA haplotype respectively).

In a particular embodiment of the invention, the probe forming a signature specific for a particular chromosome or haplotype or at least one probe of the set of probes (preferably every probe of the set or probes) forming a signature specific for a particular chromosome or haplotype hybridizes with a sequence which is specific for said particular chromosome or haplotype.

In a particular embodiment, the probes of a set of probe forming a signature of a particular domain of interest are chosen is such a way that when these probes are hybridized on said domain of interest, the gap between each of these probes is of at least 4 kb, preferably at least 5 kb.

In a particular embodiment of the invention, the probe which is specific for either chromosome 4 or chromosome 10, the probe forming a signature specific for respectively either chromosome 4 or chromosome 10, or at least one probe of the set of probes forming a signature specific for respectively either chromosome 4 or chromosome 10 (preferably every probe of the set) hybridizes with a region of the long arm of respectively either chromosome 4 or chromosome 10, which region is centromeric relatively to the D4Z4 repeat array, for example respectively:

the region of the long arm of chromosome 4 which is located at least 45 (or 48, 50 or 60 kb), preferably at least 65 kb and more preferably at least 65 kb and at most 100 kb upstream of the centromeric end of the D4Z4 repeat array; or the region of the long arm of chromosome 10 which is located at least 42 kb (or 45 kb or 50 kb), and preferably at least 42 kb (or 45 kb or 50 kb) and at most 75 kb upstream of the centromeric end of the D4Z4 repeat array.

In a particular embodiment of the invention, the probe which is specific for chromosome 4, the probe forming a signature specific for chromosome 4 or at least one probe of the set of probes forming a signature specific for chromosome 4 comprises or consists of:

i) a sequence chosen among sequences ranging from the following coordinates relative to the NCBI build 36.1 Human reference sequence: 191089412 to 191096843 (4q1 probe), 191106888 to 191116775 (4q2 probe), 191128570 to 191138567 (4q3 probe) and 191148576 to 191158554 (4q4 probe);

ii) a sequence complementary to sequence i);

iii) a sequence capable of hybridizing to sequence (i) or (ii) under stringent conditions (in particular stringent conditions as defined herein);

iv) a nucleotide variant of sequence i); or v) a portion of any of sequences (i), (ii), (iii) or (iv), said portion being as defined herein.

In a particular embodiment of the invention, the set of probes forming a signature specific for chromosome 4 comprises or consists of several (i.e., two or more than two) probes comprising or consisting in any of the aforementioned sequence i) to v). For example, said set of probes comprises or consists of one 4q1 probe, one 4q2 probe, one 4q3 probe, and one 4q4 probe.

In a particular embodiment of the invention, the probe which is specific for chromosome 10, the probe forming a signature specific for chromosome 10 or at least one probe of the set of probes forming a signature specific for chromosome 10 comprises or consists of:

i) a sequence chosen among sequences ranging from the following coordinates relative to the NCBI build 36.1 Human reference sequence: 135247926 to 135252909 (10q1 probe), 135257958 to 135262966 (10q2 probe), 135267992 to 135272976 (10q3 probe), and 135278058 to 135282988 (10q4 probe);

ii) a sequence complementary to sequence i);

iii) a sequence capable of hybridizing to sequence (i) or (ii) under stringent conditions (in particular stringent conditions as defined herein); or iv) a nucleotide variant of sequence i);

v) a portion of any of sequences (i), (ii), (iii) or (iv), said portion being as defined herein.

In a particular embodiment of the invention, the set of probes forming a signature specific for chromosome 10 comprises or consists of several (i.e., two or more than two) probes comprising or consisting in any of the aforementioned sequence i) to v). For example, said set of probes comprises or consists of one 10q1 probe, one 10q2 probe, one 10q3 probe, and one 10q4 probe.

In a particular embodiment of the invention, the probe which is specific for the qA or qB haplotype, the probe forming a signature specific for the qA or qB haplotype or at least one probe of the set of probes forming a signature specific for the qA or qB haplotype (preferably every probe of the set) hybridizes with a region of the long arm of chromosome 4qA or 4qB respectively which is telomeric, in particular immediately telomeric, relatively to the D4Z4 repeat array.

In a particular embodiment of the invention, the probe which is specific for the qA haplotype, the probe forming a signature specific for the qA haplotype or at least one probe of the set of probes forming a signature specific for the qA haplotype (preferably every probe of the set) hybridizes:
  with the repeat array of a beta-satellite sequence which is immediately telomeric relatively to the D4Z4 repeat array on the long arm of chromosome 4qA or with a portion of this beta-satellite sequence said portion being as defined herein; and/or
  the repeat array of about 1 kb of (TTAGGG)$_n$ repeat units which is immediately telomeric relatively to said repeat array of a beta-satellite sequence on the long arm of chromosome 4qA or with a portion of this region, said portion consisting of for example at least 100, 200 or 300 base pairs (bp), preferably at least 500 or 700 bp, and more preferably at least 800 or 900 bp; and/or
  with the region of about 750 bp (called qA1 in FIG. 4) which is located about 2.5 kb downstream of the telomeric end of said beta-satellite repeat array on the long arm of chromosome 4qA or with a portion of this region, said portion consisting of for example at least 100, 200 or 300, preferably at least 500 or 600 bp, and more preferably at least 700 bp; and/or
  with the region which is located at least about 8.5 kb downstream of the telomeric end of said beta-satellite repeat array on the long arm of chromosome 4qA, or with a portion thereof, said portion consisting of for example at least 100, 200 or 300, preferably at least 1 kb, at least 1.5 kb (for example 1.9 kb) or at least 2 or 5 kb. Said region encompasses the regions of chromosome 4qA which are called qA2 and qA3 herein (see in particular FIG. 4).

In a particular embodiment of the invention, the probe which is specific for the qA haplotype, the probe forming a signature specific for the qA haplotype or at least one probe of the set of probes forming a signature specific for the qA haplotype comprises or consists of:
  i) a sequence chosen among sequences ranging from the following coordinates relative to the Genbank accession number U74496.1: 2756 to 3556 (qA1 probe) and 8723 to 10672 (qA2 probe);
  ii) a sequence complementary to sequence i);
  iii) a sequence capable of hybridizing to sequence (i) or (ii) under stringent conditions (in particular stringent conditions as defined herein); or
  iv) a nucleotide variant of sequence i);
  v) a portion of any of sequences (i), (ii), (iii) or (iv), said portion being as defined herein.

In a particular embodiment of the invention, the set of probes forming a signature specific for the qA haplotype comprises or consists of several (e.g. two or more than two) probes comprising or consisting in any of the aforementioned sequence i) to v). For example, said set of probes can comprise or consist of one qA1 probe and one qA2 probe.

In a particular embodiment of the invention, the probe which is specific for the qB haplotype, the probe forming a signature specific for the qB haplotype or at least one probe of the set of probes forming a signature specific for the qB haplotype hybridizes with the totality of the region of about 6 kb which is immediately telomeric relatively to the D4Z4 repeat array on the long arm of chromosome 4qB or with a portion of this region, said portion being as defined herein. Such a portion can be for example the region of about 5.2 kb located about 800 bp downstream of the telomeric end of the D4Z4 repeat array on the long arm of chromosome 4qB, or the region of about 4.5 kb located about 1.5 kb downstream of the telomeric end of the D4Z4 repeat array on the long arm of chromosome 4qB, or with a portion of one of these regions, said portion being as defined herein.

In a particular embodiment of the invention, the probe which is specific for the qB haplotype, the probe forming a signature specific for the qB haplotype or at least one probe of the set of probes forming a signature specific for the qB haplotype comprises or consists of:
  i) a sequence chosen among sequences ranging from the following coordinates relative to the NCBI build 36.1 Human reference sequence: 191252023 to 191253372 (qB1-3 probe) and 191248879 to 191252040 (qB1-4 probe), or the unique probe formed of qB1-3 and qB1-4 resulting in qB1;
  ii) a sequence complementary to sequence i);
  iii) a sequence capable of hybridizing to sequence (i) or (ii) under stringent conditions (in particular stringent conditions as defined herein);
  iv) a nucleotide variant of sequence i); or
  v) a portion of any of sequences (i), (ii), (iii) or (iv), said portion being as defined herein.

In a particular embodiment of the invention, the set of probes forming a signature specific for the qB haplotype comprises or consists of several (e.g. two or more than two) probes comprising or consisting in any of the aforementioned sequence i) to v). For example, said set of probes can comprise or consist of one qB1-3 probe and one qB1-4 probe.

In a particular embodiment of the invention, the repeat probe or at least one of the repeat probes, and preferably every repeat probe, hybridizes, either (i) along its whole length, with the whole sequence of the D4Z4 repeat unit of a D4Z4 repeat array, or (ii) preferably along its whole length, with a portion of the D4Z4 repeat unit of a D4Z4 repeat array. In particular, said portion can consist in about a half of said D4Z4 repeat unit or be located at one end of said D4Z4 repeat unit or close to one end of said D4Z4 repeat unit.

In a particular embodiment of the invention, the repeat probe or one of the repeat probes is about 3.3 kb in length.

In a particular embodiment of the invention, one or several repeat probe(s) comprise(s) or consist(s) of:
  i) a sequence chosen among sequences ranging from the following coordinates relative to the Genbank accession number U85056.1: 24213 to 27507 (DeeZee probe), 24213 to 25948 (Dee probe) and 25763 to 27507 (Zee probe);
  ii) a sequence complementary to sequence i);
  iii) a sequence capable of hybridizing to sequence (i) or (ii) under stringent conditions (in particular stringent conditions as defined herein);
  iv) a nucleotide variant of sequence i); or
  v) a portion of any of sequences (i), (ii), (iii) or (iv), said portion being as defined herein.

In a particular embodiment of the invention, the repeat probe used is a DeeZee probe. In another particular embodiment of the invention, at least two repeat probes are used, in particular one Dee probe and one Zee probe. The Dee and Zee probes are contained in constructs provided respectively as SEQ ID No 1 and SEQ ID No 2, where they appear supplemented at each of their ends, with a few nucleotides in addition to the respective Dee and Zee probe sequence (positions indicated), used for the construct and corresponding to restriction sites. Each of the Dee and Zee probes contains half of the D4Z4 repeat unit sequence and were obtained by de novo synthesis.

In a particular embodiment, the nucleotide variant of sequence (i) differs from sequence (i) by 1 to 10, nucleotide substitution(s), in particular by, 1, 2, 3, 4, 5, 6, 7, 8, 9 or 10 nucleotide substitution(s).

When the repeat probe or at least one of the repeat probes hybridizes, along its whole length, with the whole sequence of the repeat unit of a D4Z4 repeat array, for example when a repeat probe of sequence DeeZee is used, the number of D4Z4 repeat units in a D4Z4 repeat array can be determined by:

1) measuring, for this repeat array, the total length (L) of the hybridization signal that corresponds to the hybridized repeat probe; and 2) calculating the number (n) of D4Z4 repeat units of said D4Z4 repeat units using the ratio $n=L/I$, wherein I corresponds to the length one D4Z4 repeat unit. L is generally equal to 3.3 kb.

When the repeat probe or at least one of the repeat probes hybridizes with a portion of a D4Z4 unit repeat (e.g. has a length inferior to 3.3 kb), the number of D4Z4 repeat units in a D4Z4 repeat array can be determined by counting the number of hybridization signals corresponding to said repeat probe in said repeat array or by measuring the distance between the beginning of the first hybridization signal corresponding to a repeat probe and the end of the last hybridization signal corresponding to a repeat probe in this repeat array.

In addition, using at least one repeat probe hybridizing (along its whole length) with a portion located at one end of a repeat unit or close to one end of a repeat unit of the D4Z4 repeat array enables determination of the orientation of each of the D4Z4 repeat unit or of at least some of these repeat units in a D4Z4 repeat array. Determining the orientation of the repeat units enables determination of inverted D4Z4 repeats which may be of use in interpretation of the results of the detection.

In one particular embodiment of the invention, several (at least two) different repeat probe(s) are used. Generally (i) each of these repeat probes hybridizes with a distinct region of the D4Z4 repeat unit in a D4D4 repeat array and/or (ii) one of said probes hybridizes with a region of the D4Z4 repeat unit which is included, totally or in part, in the region of the D4Z4 repeat unit which hybridizes with another of said probe(s). In addition, these repeat probes are preferably of different size and/or labelled with at least one different label.

Overlap between two repeat probes hybridizing to different regions of the same D4Z4 repeat unit can be of any size comprised between 0 kb and the length of one repeat unit, for example between 0 and 3.3 kb, especially, 100 bp, 200 bp or 500 bp.

In a particular embodiment, the method of the invention includes detecting and analysing rearrangements in the region close to the D4Z4 repeat arrays, particularly detecting deletions of a portion of the region immediately centromeric to the D4Z4 repeat arrays. This detection may involve measuring of the distances between one or several probes centromeric to the repeat array and comparing with the expected corresponding distances according to reference sequences reflecting a normal region in the vicinity of D4Z4 repeat arrays. If a shorter than expected distance is found, it is an indication of a deletion which occurred in the sequences between the considered probe and the repeat array. Typing of these signals may allow to define whether the deletion occurred on a 4qA chromosome or on a 4qB or on a 10q chromosome or optionally on a Y chromosome.

Alternatively, a deletion may be detected by the absence of a probe within a signature of one of the chromosomes or of one of the haplotypes. Alternatively, or additionally, a deletion may be detected by a shorter than expected distance between several probes within a signature of one of the chromosomes or of one of the haplotypes.

Insertions may be detected as longer than expected distances between probes if the inserted sequences are not contained in the sequences of the probes used, and/or as the presence of unexpected hybridization signals and/or as longer than expected lengths of probes if the inserted sequences are contained in the sequences of the probes used. As described in the examples, the identification of the inserted sequences may involve additional hybridizations with modified probe sets.

Thus, in a particular embodiment, the method of the invention, further includes hybridizing the nucleic acid to be analysed with one or several of the following probes, which are preferably labelled (as described herein):

a probe or a set of probes hybridizing with the region of about 42 kb which is immediately centromeric relatively to the D4Z4 repeat array on the long arm of chromosome 4 or with a portion of this region and/or hybridizing with the region of about 42 kb which is immediately centromeric relatively to the D4Z4 repeat array on the long arm of chromosome 10 or with a portion of this region; and/or a probe or a set of probes hybridizing with the region of about 15 kb which is immediately telomeric relatively to the D4Z4 repeat array on chromosomes of the qA haplotype and/or on chromosomes of the qB haplotype or with a portion of this region.

In a particular embodiment, the method of the invention includes a step of analysing methylation, in particular CpG methylation, especially by detecting methylcytosine-rich regions for example by incubating the nucleic acid sample with one or several anti-methylcytosine antibodies (in particular monoclonal or polyclonal antibodies). The nucleic acid sample can be incubated with said antibodies before or after stretching of the nucleic acid sample on a support but is preferably incubated after the step of stretching. For example, said incubation can be performed together with probes hybridization or preferably together with antibodies used for the detection of hybridized probes.

The probe designs described herein may more generally be used to investigate other biological events occurring in or near the FSHD locus or other D4Z4 repeat array bearing loci, and in particular to study DNA replication in these loci. Thus, in a particular embodiment, the method of the invention further includes a step of analysing biochemical events, in particular DNA replication kinetics, in the telomeric extremities of the long arms of chromosomes 4 and/or 10. For example, replicating cells may be incubated with modified nucleotides (such bromodeoxyuridine, chlorodeoxyuridine, iododeoxyuridine) simultaneously or successively. Said nucleotides, when incorporated during the DNA replication process, may be detected by incubating the nucleic acid of the cells with one or several anti-bromodeoxyuridine-, anti-chlorodeoxyuridine- and/or anti-iododeoxyuridine-antibodies (in particular monoclonal or polyclonal antibodies). The nucleic acid sample can be incubated with said antibodies before or after stretching of the nucleic acid sample on a support but is preferably incubated after the step of stretching. For example, said incubation can be performed together with probes hybridization or preferably together with antibodies used for the detection of hybridized probes.

Said modified nucleotides may be detected with fluorochromes identical to or different from the fluorophores used for the detection of probes, but are preferably detected with fluorochromes different from those used for the detection of probes. Strategies to allow simultaneous detection of incorporated modified nucleotides and hybridized probes are detailed in Lebofsky and Bensimon, 2006.

In a particular embodiment, the method of the invention includes a step of analysing other biological events such as transcription, transcription factor bindings and/or binding of other DNA binding proteins. Such analysis will require specific adaptations, which can be easily done by the person skilled in the art.

Detectable labels suitable for use in the present invention include any composition detectable by spectroscopic, photochemical, biochemical, immunochemical, electrical, optical or chemical means. In a particular embodiment of the invention, probes are labelled with one or several (for example 2) radioactive elements (for example $^3H$, $^{125}I$, $^{35}S$, $^{35}C$ or $^{32}P$) or non radioactive elements. Non-radioactive elements include in particular fluorochromes (or fluorophores) and other "cold" labelling such as haptens (in particular biotin or digoxigenin (DIG)), enzymes chemical (e.g., horse radish peroxidase or alkaline phosphatase) or chemico-luminescent markers, as well as with beads, particles or with targets for antibodies.

In a particular embodiment, fluorescent label(s) is(are) used. Any fluorochrome can be used, in particular the fluorochromes typically used in biotechnology and research applications, including Fluorescein isothiocyanate (FITC), the Alexa Fluor dyes produced by Molecular Probes, such as red fluorescent dyes Alexa (A594), and the DyLight Fluor dyes produced by Thermo Fisher Scientific or by Rockland Immunochemicals, Inc, the Texas Red fluorophore or others fluorophores which are derivatives of rhodamine, coumarin or cyanine.

The probes can be labelled in particular by incorporation of modified nucleotides which are optionally revealed separately, for example by incorporation of nucleotides modified by biotinylation, with DIG or other haptens which are revealed by a system of layers of antibodies or of specific molecules.

In a particular embodiment, the probes are modified to confer them different physicochemical properties (such as by methylation, ethylation). In another particular embodiment, the probes may be modified to add a functional group (such as a thiol group), and optionally immobilized on bead (preferably glass beads).

The labels can be attached directly or through a linker moiety. For example, a label may be attached to a nucleoside, nucleotide, or analogue thereof at any position that does not interfere with detection or hybridization as desired.

The label(s) may be incorporated into the probes by any of a number of means well known to those of skill in the art. For example having recourse to nick translation or PCR or Random Priming using tagged nucleotides. The probe (e.g., DNA) can be amplified, for example by polymerase chain reaction (PCR), in the presence of labelled nucleotide, e.g. fluorescein-labeled UTP and/or CTP, or labelled deoxynucleotide triphosphates (dNTPs). Methods for labelling probes are disclosed for example in Sambrook et al. (Molecular Cloning, A laboratory Manual, Third Edition; chapter 8 and in particular page 9.3.).

Preferably, labeled nucleotide according to the present invention are Chlorodeoxyuridine (CIdU), Bromoeoxyuridine (BrdU) and or Iododeoxyuridine (IdU).

The label of the probes can be either "direct", i.e. directly attached to or incorporated into the probe prior to the step of hybridization or "indirect", i.e. are joined to the hybrid duplex after hybridization. The indirect label is preferably attached to a binding moiety that has been attached to the probe prior to the hybridization. For example, the probe may be biotinylated before the hybridization. After hybridization, an avidin-conjugated fluorophore will bind the biotin bearing hybrid duplexes providing a label that is easily detected.

In a particular embodiment of the invention, all the probes are labelled with the same label(s).

Alternatively, in another particular embodiment of the invention, at least one probe is labelled with one or several label(s) different from the label(s) of other probes. For example, probes can be labelled with two different labels, in particular with two different fluorochromes, for example one fluorochrome that emits in the green/yellow spectrum (such as FITC) and one fluorochrome that emits in the red spectrum (such as A594). In a further particular embodiment, ar least one repeat probe or all the repeat probes is (are) labelled with one or several label(s) different from the label(s) of the localization probes.

In a further aspect, the present invention relates to a method for analyzing in vitro D4Z4 tandem repeat arrays of nucleic acid contained on nucleic acid representative of chromosomes (in particular for determining in vitro the number of D4Z4 repeat units in said D4Z4 tandem repeat arrays) and for localizing said repeat arrays on a particular chromosome, said method comprising performing the method described herein, in which step c) further includes determining, for every detected D4Z4 repeat array, whether said repeat array is located on a chromosome of the qA haplotype and in particular on a chromosome 4, and optionally whether said repeat array is located on a chromosome of the qB haplotype; and optionally, whether said repeat array is located on a chromosome 10; and optionally, whether said repeat array is located on a chromosome Y.

Thus, using a method of the invention, one can assess, for every detected D4Z4 repeat array, whether said repeat array is located on a chromosome 4qA and optionally, whether said repeat array is located on a chromosome 4qB, 10 (in particular on a chromosome 10qA or if any, 10qB) and/or on a chromosome Y.

Another aspect of the present invention relates to a method for the in vitro diagnosis of FSHD and/or for in vitro detecting of susceptibility to FSHD in a patient. Said method comprises or consists in analyzing by a method of the invention as described herein, D4Z4 tandem repeat arrays of nucleic acid contained on nucleic acid representative of chromosomes, in particular D4Z4 tandem repeat arrays contained in a genomic DNA sample obtained from said patient. Said method can in particular comprise or consist in determining in vitro the number of D4Z4 repeat units in the D4Z4 repeat array of every 4qA allele detected in genomic DNA sample obtained from said patient.

In a particular embodiment, said method comprises or consists in determining (i) the number of alleles 4qA in genomic DNA obtained from said patient and (ii) the number of D4Z4 repeat units in the D4Z4 repeat array of each of these alleles.

In one particular embodiment of the invention, a number of D4Z4 repeat units below or equal to 12 and in particular below or equal to 11, 10, 9, 8, 7, 6, 5 or 4 for one or both allele(s) 4qA of a patient is indicative that this patient is susceptible to FSHD.

In another aspect, the present invention relates to a kit characterized in that it comprises or consists of at least:
- one repeat probe or set of repeat probe(s);
- one probe or one or several set(s) of probes which enable(s) to distinguish chromosome 4 from chromosome 10; and
- one probe or one or several set(s) of probes which enable(s) to distinguish the qA haplotype from the qB haplotype, and
- optionally, one probe or one or several set(s) of probes which enable(s) to distinguish chromosome Y from chromosome 4 and/or from chromosome 10, said probes being as defined herein and being labelled or intended to be labelled.

In a particular embodiment of the invention, the kit of the invention can further comprise or consists of one or several elements chosen among:
- a support appropriate for stretching of nucleic acid, in particular appropriate for molecular combing;
- a device allowing stretching of nucleic acid, in particular appropriate for molecular combing of nucleic acid,
- one or several reagent(s) for the hybridization and/or the detection of the probes;
- control samples for example nucleic acid samples that were previously assessed for the repeat number using conventional methods;
- instructions to carry out a method of the invention using said kit; and
- a software which makes the carrying out of the methods of the invention easier.

In a further aspect, the present invention also relates to a composition comprising or consisting of at least the following probes, in solution: one or several repeat probe(s), one probe or one or several set(s) of probes which enables to distinguish chromosome 4 from chromosome 10, one probe or one or several set(s) of probe which enables to distinguish the qA haplotype from the qB haplotype, and optionally, one probe or one or several set(s) of probes which enable(s) to distinguish chromosome Y from chromosome 4 and/or from chromosome 10, said probes being preferably labelled and being as defined herein. In addition, said composition can further comprise any of the other probes or set of probes as defined herein, and/or antibodies as defined herein.

Another aspect of the present invention relates to the kit of the invention or the composition of the invention or for the diagnosis of FSHD and/or for detecting susceptibility to FSHD in a patient. Said diagnostic kit and said composition can be used as described herein.

Another aspect of the present invention relates to the use of the kit of the invention or of the composition of the invention, for analyzing in vitro D4Z4 tandem repeat arrays of nucleic acid contained on nucleic acid representative of chromosomes, and in particular for determining the number of D4Z4 repeat units in D4Z4 repeat arrays of nucleic acid. This analysis can de performed in particular using a method of the invention.

In another aspect, the present invention relates to the use of the method for analyzing D4Z4 tandem repeat arrays according to the invention, of the kit of the invention or of the composition of the invention, for clinical research and/or for diagnosis, in particular for neonatal, prenatal and/or pre-implantation diagnosis and/or for genetic counseling.

Another aspect of the present invention relates to a method for identifying biochemical events and/or genetic and epigenetic parameters involved in the phenotype of FSHD. Said method comprises or consists of analyzing, by a method of the invention, organization of D4Z4 repeat arrays contained on nucleic acid representative of chromosomes obtained from several patients (for example at least 5, 10, 20, 30, 50 or 100 patients), in particular organization of D4Z4 repeat arrays contained on nucleic acid of chromosomes 4, and optionally 10 and/or Y, said analysis being performed independently for each patient. Said method can in particular comprise or consist in determining the number of D4Z4 repeat units in the D4Z4 repeat array contained on said nucleic acid, and/or determining the orientation of the D4Z4 repeat units in said D4Z4 repeat arrays, and/or detecting and analysing rearrangements in said D4Z4 repeat arrays or in regions close to said D4Z4 repeat arrays and/or analysing methylation, in particular CpG methylation, and/or analysing biochemical events, in particular DNA replication kinetics, as described herein. In a particular embodiment, said method further comprises comparing the data obtained for each patient and thus identifying novel biochemical events and/or genetic and epigenetic parameters involved in the phenotype of FSHD, Finally, the present invention relates to the use of a molecular combing technology for analyzing in vitro D4Z4 tandem repeat arrays of nucleic acid contained on nucleic acid representative of chromosomes, in particular for determining in vitro the number of D4Z4 repeat units in said D4Z4 tandem repeat arrays, as described herein.

The invention will be further described in the following examples, which do not limit the scope of the invention described in the claims.

Panels A-D: the location probes (4q1, 4q2, 4q3, 4q4, 10q1, 10q2, 10q3, 10q4, qA1, qA2 and qB1, as described in experimental procedures) were labelled with digoxygenin and revealed in green. The repeat probe was labelled with biotin and revealed in red. The observed signals are shown here, with one signal representative of each allele (A: 4qA allele; B: short 10q allele; C: long 10q allele; D: 4qB allele). Due to lower than 100% hybridization efficiency, some of the signals appear shorter than they should. This is particularly the case with the second probe (counting from the centromere, i.e. the 4q2 probe) in panel A.

Panel E: in a separate hybridization, the beta-satellite probe was also present. A signal representative of the 4qA allele is shown. A signal corresponding to the beta-satellite probe is detected adjacent to the repeat array. The confusion with the qB probe can be seen by comparing with the signal obtained for 4qB (panel D). It should be noted that in the panel E signal, the qA2 probe is not detected, probably because of a break in the molecule or of inefficient hybridization.

Figure 3:
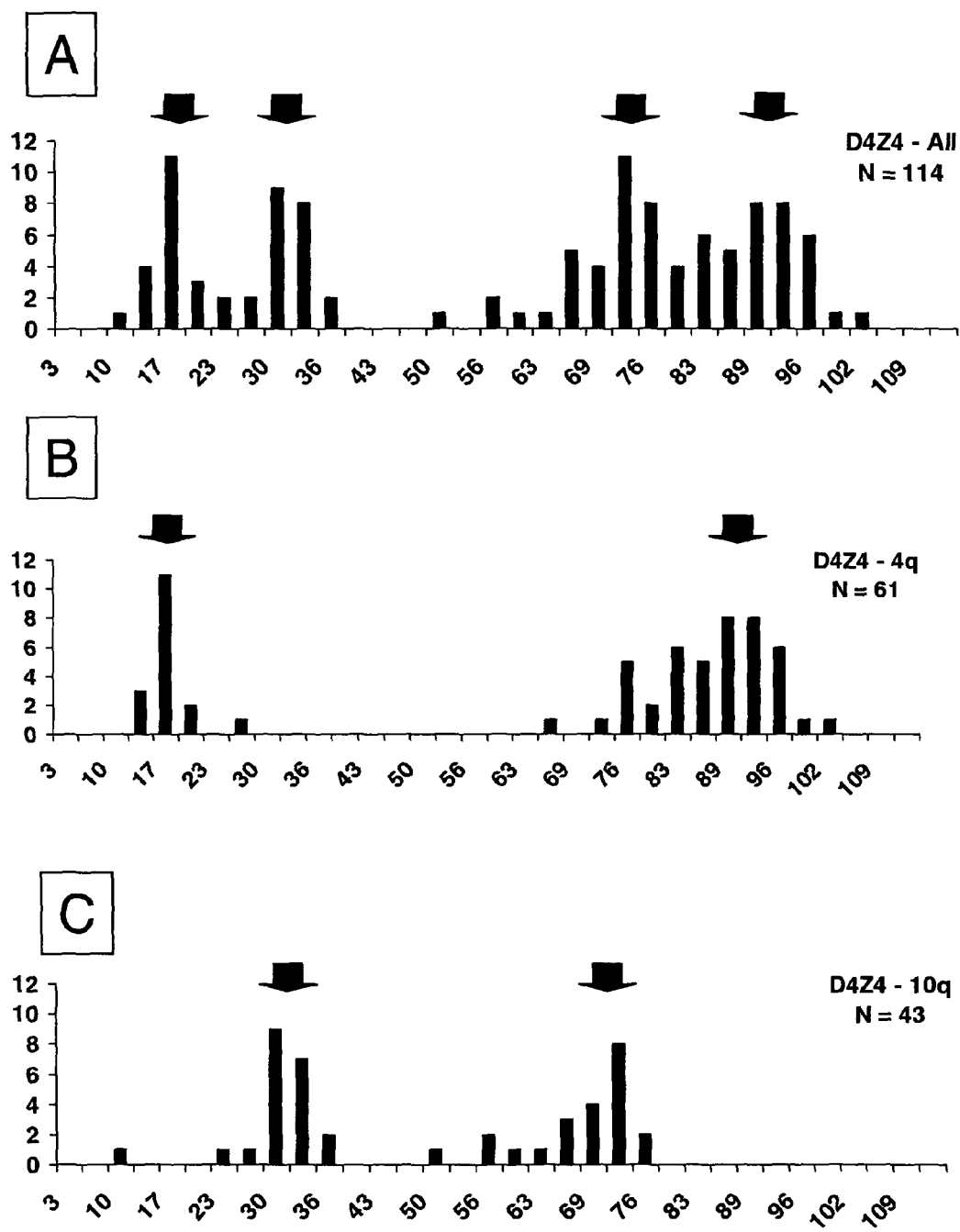
Figure 3:
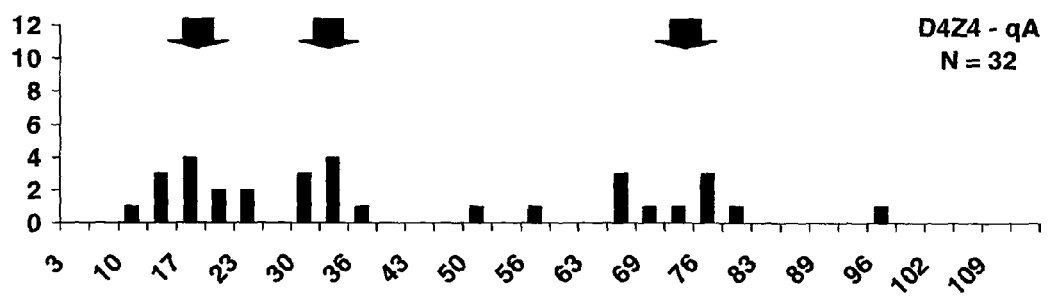
Figure 3:
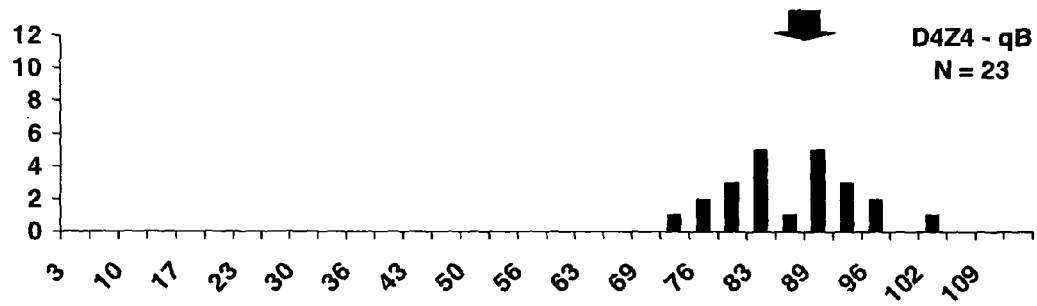

FIG. 3. Histogram of the D4Z4 measures. Histogram showing the number of intact D4Z4 repeat arrays within a given length interval which were contained on genomic DNA isolated from the "Patient 1" blood sample. Interval width is 3.3 kb, the first bar represents the number of measures within the [0-3.3 kb] interval. Thus, for example, the fifth bar represents the number of measures in the [13.2 kb-16.5 kb] interval. Panel A: the length of every detected D4Z4 repeat array was recorded (114 measures). Four different modes appear on this histogram (each of these modes is pointed out by an arrow). Panel B: the length of every intact D4Z4 repeat arrays associated with 4q hybridization signals was recorded (61 measures). Two different modes appear on this histogram (each of these modes is pointed out by an arrow). Panel C: the length of every intact D4Z4 repeat arrays associated with 10q hybridization signals was recorded (43 measures). Two different modes appear on this histogram (each of these modes is pointed out by an arrow). Panel D: the length of every intact D4Z4 repeat arrays associated with qA hybridization signals was recorded (32 measures). Three different modes appear on this histogram (each of these modes is pointed out by an arrow). Panel E: the length of every intact D4Z4 repeat arrays associated with qB hybridization signals was recorded (23 measures). One mode appears on this histogram (pointed out by an arrow).

Figure 4:
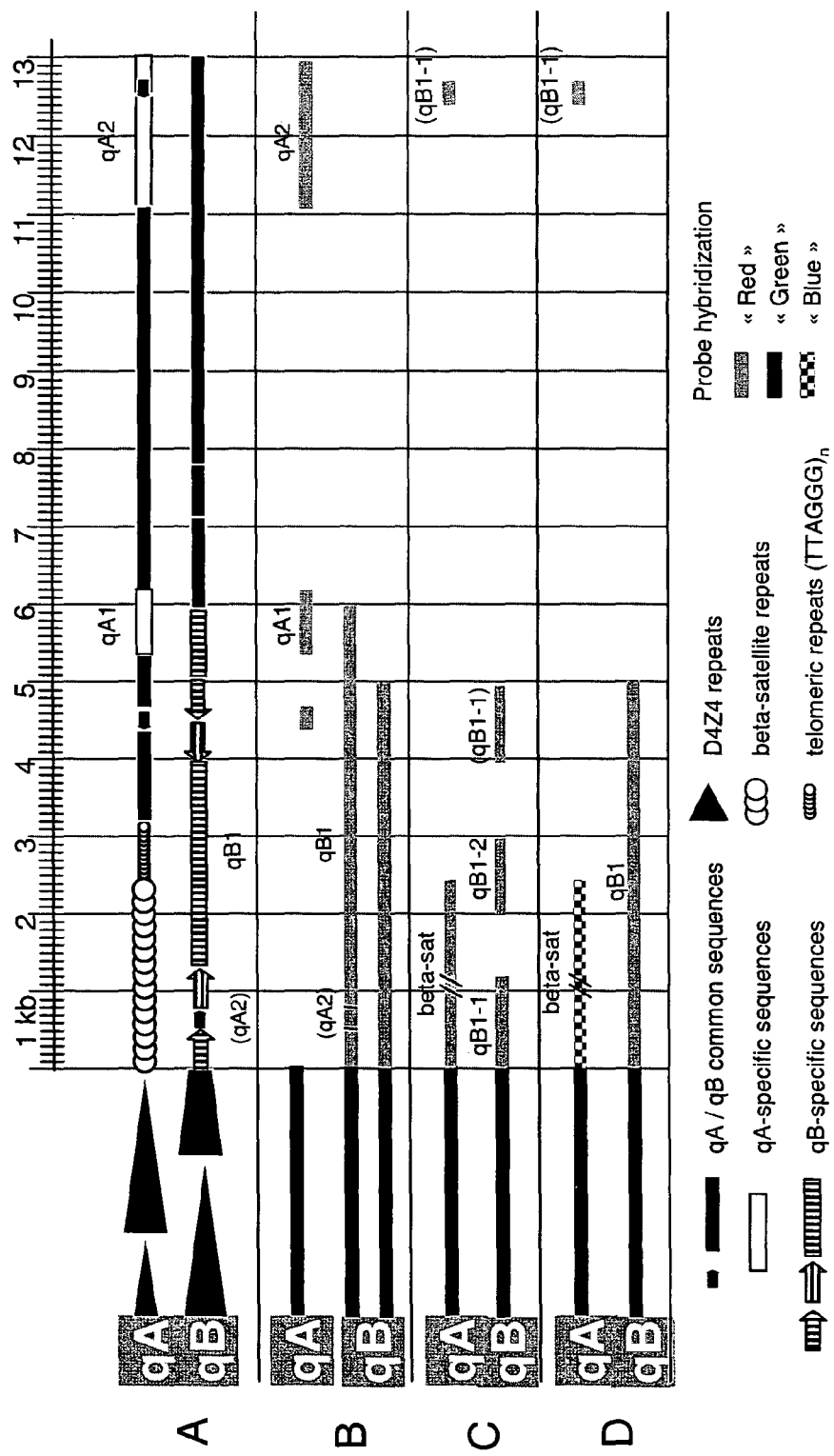

FIG. 4. A. Scheme showing the organization of the different regions which are telomeric to the D4Z4 repeat array on the long arm of chromosomes of the qA haplotype (in particular chromosomes 4qA and 10qA) and on the long arm of chromosomes of the qB haplotype (in particular chromosome 4qB). For the qA haplotype, the length of the beta-satellite repeat array and the TTAGGG$_n$ repea array were chosen arbitrarily, since these lengths are highly variable. B-D. Examples of sets of probes that can be used to distinguish the qA haplotype from the qB haplotype. In panel B, two options are indicated for the unique qB probe. In panel C is shown how one can obtain three ~1 kb-signals with two probes on qB.

Figure 5A:
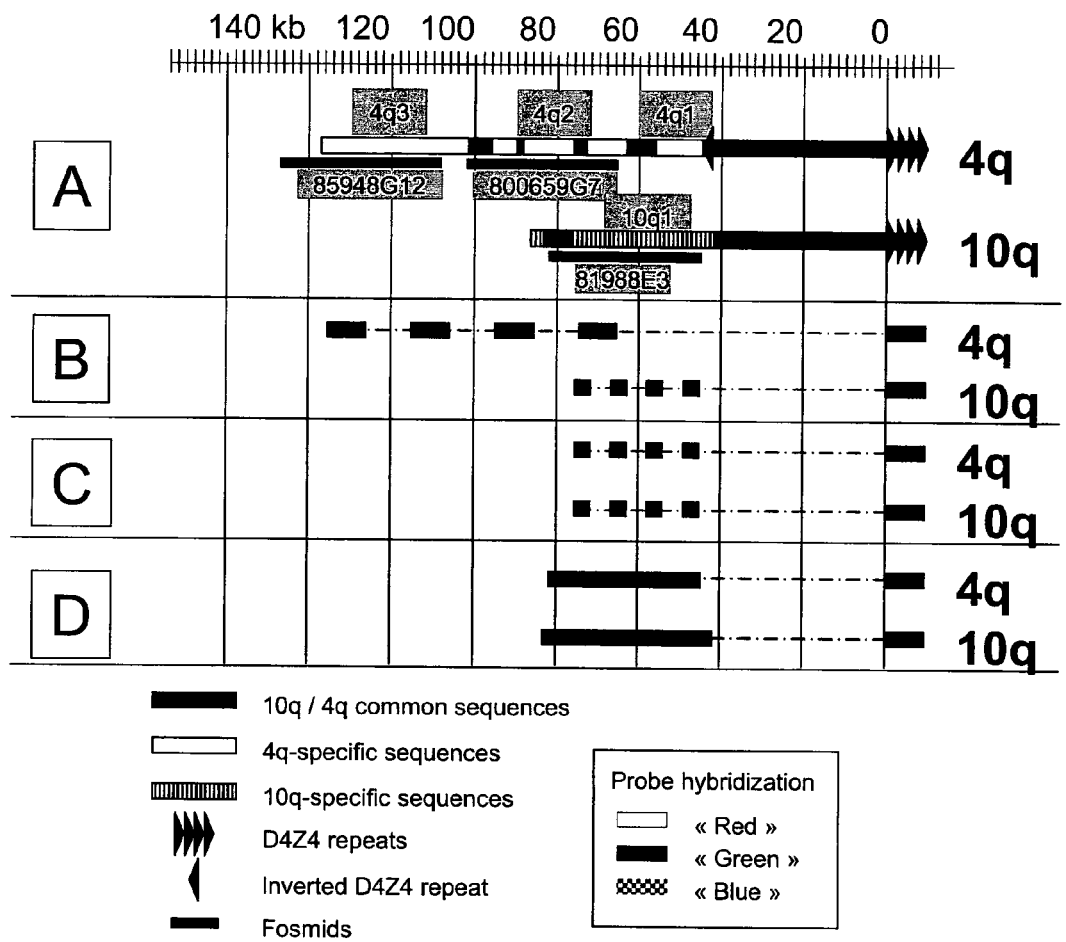
Figure 5B:
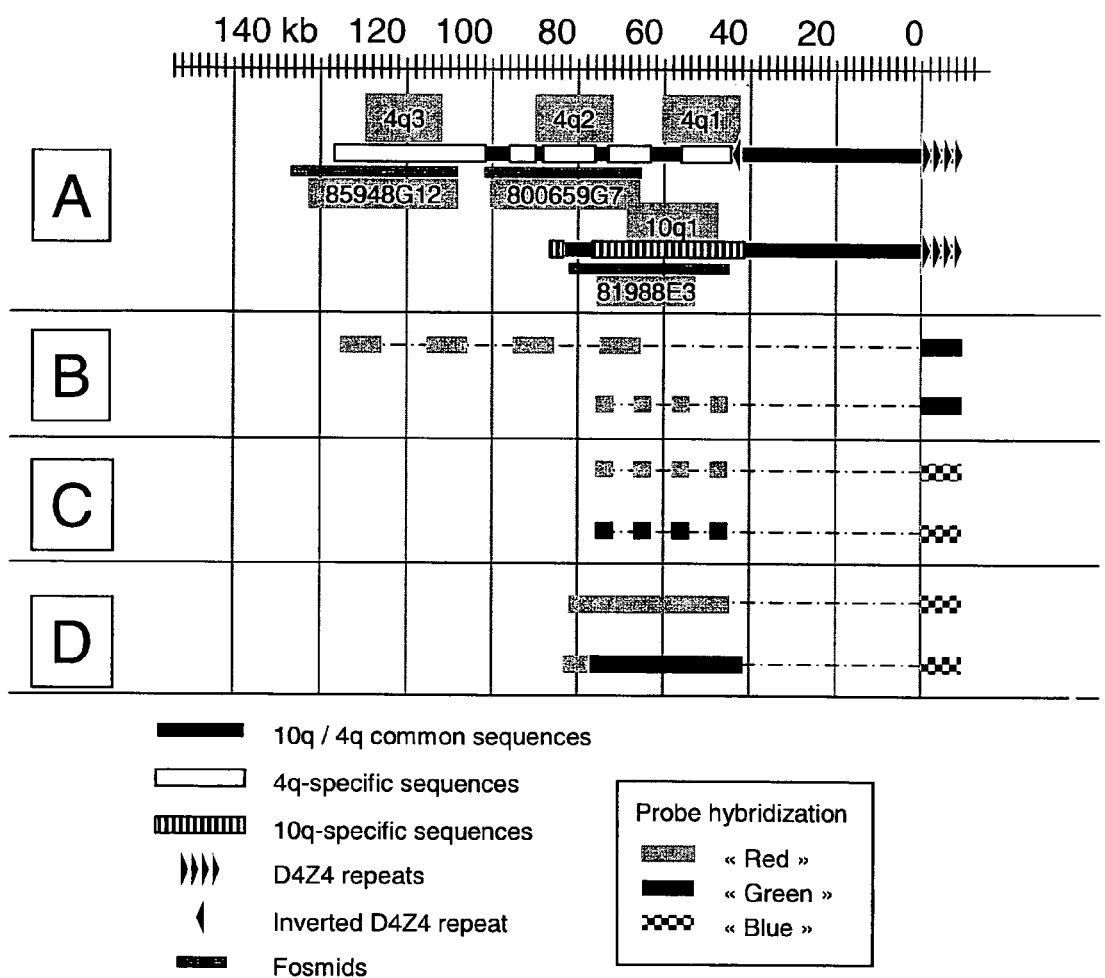

FIGS. 5.(a and b). A. Scheme showing the organization of the different regions which are centromeric to the D4Z4 repeat array on chromosomes 4q and 10q. B-D. Examples of sets of probes that can be used to distinguish chromosome 4 from chromosome 10.

Figure 6A:
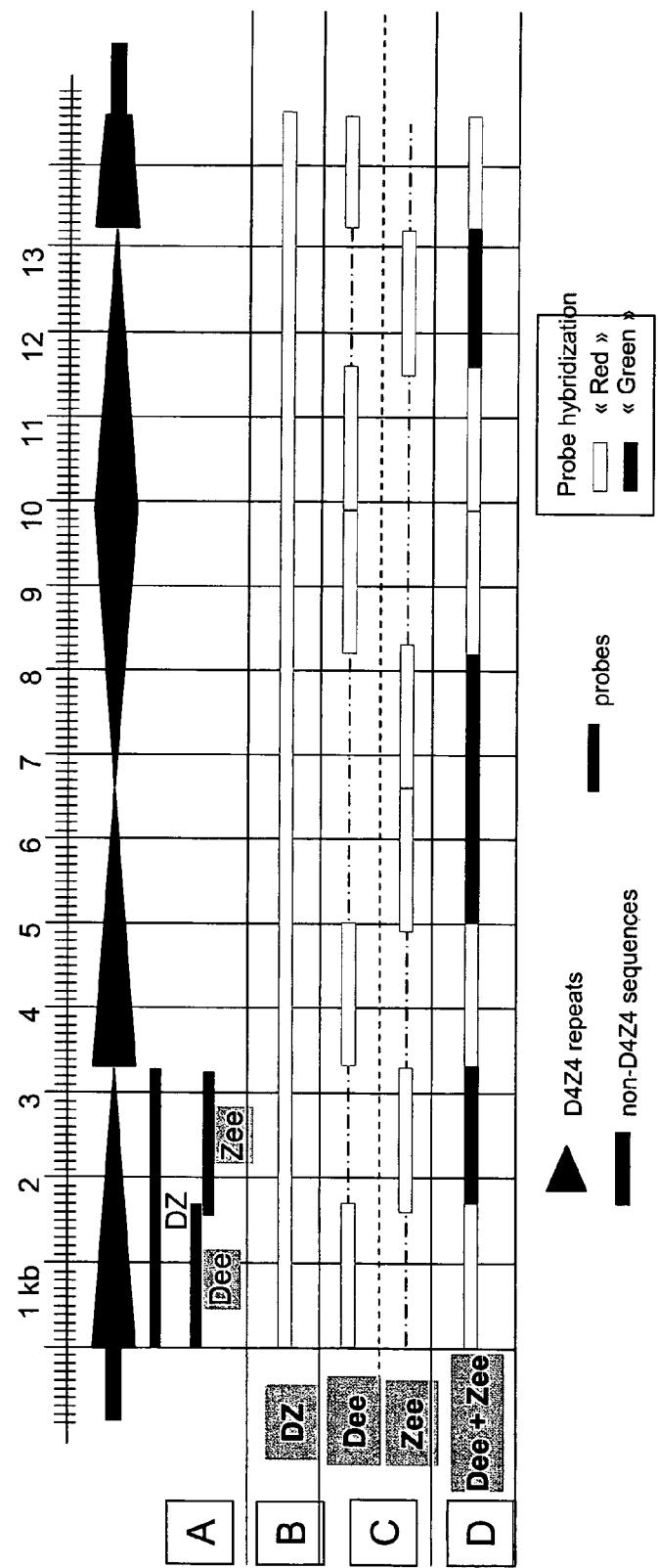
Figure 6B:
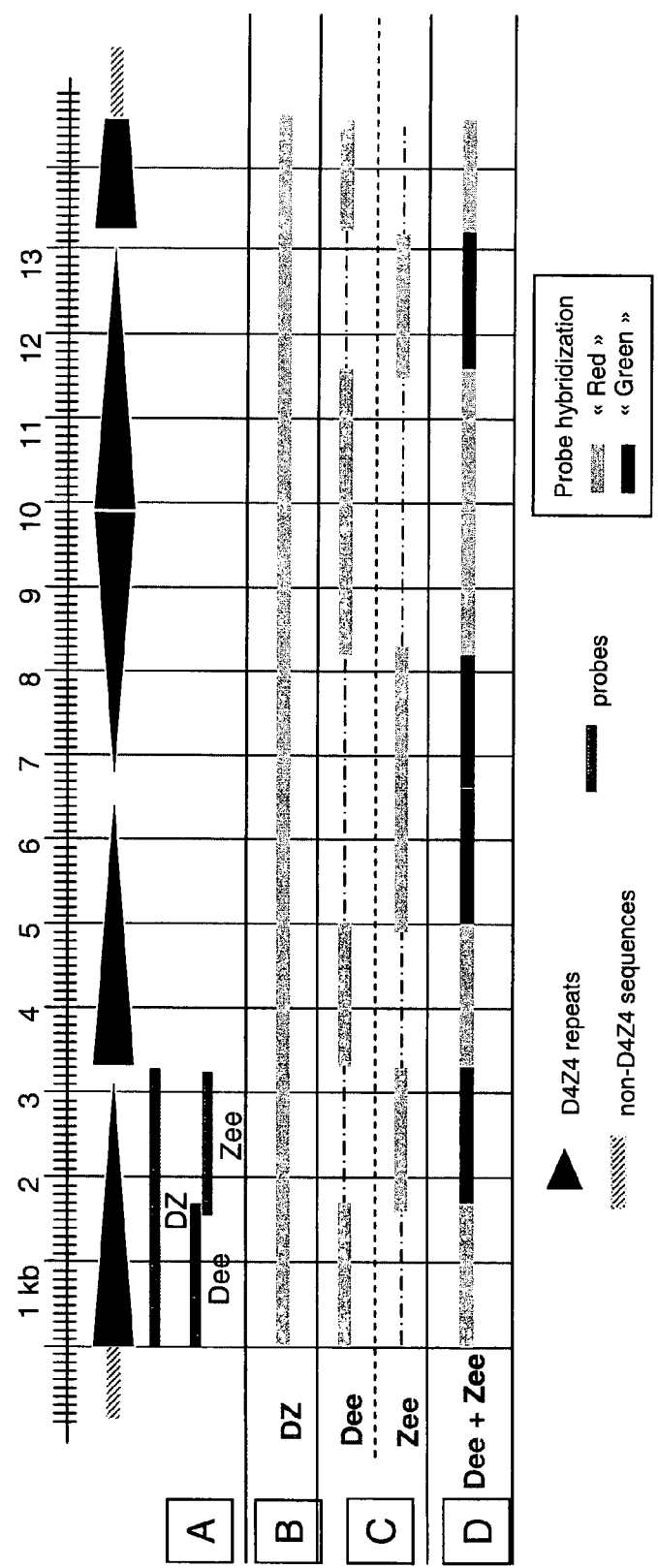

FIGS. 6.(a and b). Use of two different repeat probes for determining the orientation of the D4Z4 repeat units in a D4Z4 repeat array. The two repeat probes used hybridize with about one half of the D4Z4 repeat unit (Dee and Zee hybridize respectively with the centrometic half and the telomeric half of the D4Z4 repeat unit). In addition, they slightly overlap over 100 bp and are labelled with a different label. Panel A shows a hypothetical organization of the repeat array, with one inverted repeat (the third starting from the centromere). Panel C shows the expected hybridization patterns for both probes, used one at at time. Panel D shows the expected hybridization pattern for both probes used together with different labels.

Figure 7:
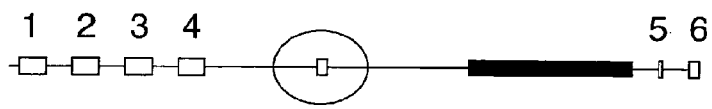
Figure 7:
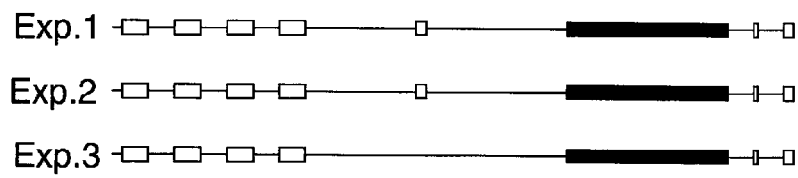
Figure 7:
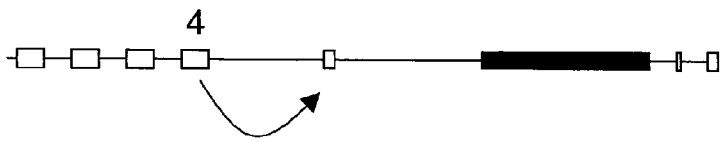

FIG. 7. Use of a combinatorial approach to determine the nature of an inserted sequence. In panel A is shown the schematic representation of hybridization signals detected in a hypothetical case. The 6 numbered probes, detected in red (non circled white boxes), are in their expected location, as well as the repeat probe detected in green (black boxe). The presence of an unexpected hybridization signal (circled) is indicative of the insertion of sequences in the gap between the hybridization signal corresponding to probe number 4 and the hybridization signal corresponding to the repeat probe, these inserted sequences being present in one of the red probes. In order to assess which probe hybridizes in this location, one can perform the same hybridization experience while omitting one or several probes choosen among probes 1-6. In panel B is an optimal scheme of probes to identify the duplicated probe: in the three experiments described, the probes with an X should be included, those with a dash omitted. Depending on when the unexpected signal appears or not, the duplicated probe may be uniquely identified. For example, if the results of the experiments are as depicted in panel C, the inserted sequences originated from probe number 4 (panel D). The size of the unexpected signal is indicative of the portion of the probe that was duplicated.

EXAMPLES

1. Design of the Probes

We designed probe sets to measure the D4Z4 repeat arrays, assess their location on 4q or 10q chromosomes and distinguish the two 4q haplotypes (qA and qB) (see FIG. 1) and methods to analyze the data generated.

The probe designed to measure the repeat array is the whole sequence (3.3 kb) of a single D4Z4 repeat.

The probes designed to distinguish arrays on 4q versus 10q chromosomes are located centromeric to the repeat array, about 50 kb upstream, i.e. as close as possible in the region that is distinct between 4q and 10q. One set of probes hybridizes on 4q as four signals separated by 10 kb gaps, the closest probe being ~65 kb upstream of the repeat array. The three probes closest to the repeat array generate a 10 kb-signal, the most distant one a 7.5 kb-signal. The other set hybridizes on 10q as four 5 kb signals separated by 5 kb gaps, the closest probe being ~45 kb upstream of the repeat array The probes designed to distinguish qA and qB haplotypes are located in the short sequences unique to either haplotype, namely a 5 kb sequence specific to qB immediately downstream of the repeat array and two sequences specific to qA, 801 bp and 1950 bp long, located respectively about 2.5 kb and 8.5 kb downstream of the telomeric end of the beta-satellite repeat array on the long arm of chromosome 4qA, which means located approximately—the length of a D4Z4 repeat array being variable—8 kb and 13.5 kb respectively downstream of the telomeric end of the D4Z4 repeat array.

One choice governing this design of probes was to keep a fully interpretable code with only two fluorochromes, in order to allow fast and simple image acquisition. Since the length of the repeat array is highly variable, the fluorochrome associated with the repeat probe is its only constant characteristic. In order to include all possible measurements of the arrays in the analysis (discussed below), it is necessary to unambiguously recognize the repeat probe independently of its context. Therefore, one specific fluorochrome was dedicated for this probe, leaving only one other fluorochrome for all the other probes. Thus, the location probes (the probes designed to distinguish chromosome 4 from chromosome 10 and the qA haplotype from the qB haplotype) were made distinguishable by their length, spacing, and position relative to the array. The redundant differences allow for high robustness relatively to sequence variants (e.g. deletion of sequences upstream of the repeat array), and to breaks in the DNA molecules during the Molecular Combing process that may occur within the motif.

In order to test for FSHD, this whole set of probes is hybridized on combed genomic DNA, the D4Z4 probe being detected with one color, usually green (fluorochromes: FITC and A488) and the location probes with another, usually red (fluorochromes: A594 and Texas Red). For the analysis, all the signals containing at least one green segment are included. All segments in one signal were measured, and where the succession of probes allows unambiguous distinction, the signal was manually classified as 4q or 10q and/or qA or qB.

2. Analysis of the Generated Data

The most direct method to assess the size of the repeat arrays would be to plot the histogram of the lengths of green probes for the selected signals, i.e. those which have been fully characterized (chromosome and haplotype). On a histogram of 4qA signals, for example, zero, one or two peaks are expected for a homozygous 4qB/4qB, heterozygous 4qA/4qB or homozygous 4qA/4qA individual respectively. In the case of a mosaic, a supplementary peak would appear. The size of the arrays on 4qA chromosomes are determined by measuring the mean of the lengths for the green segments in the detected peak(s) of the histogram. The number of repeat units can be deduced from the length and the length/(size of one repeat) ratio.

However, given the significant probability for a break to occur within the motif of probes and/or for a probe to go undetected (especially the shorter probes), excluding all incomplete or ambiguous signals from the measurements reduces considerably the number of repeat segments actually considered for the calculation of the mean, thus reducing the precision of this calculation. Therefore, we decided to plot a histogram of all the measurements of repeat arrays, localized or not (unsorted data, see an example in FIG. 3, panel A). Several peaks appear, corresponding to the two 4q chromosomes, the two 10q chromosomes, and in male individuals the Y chromosome (where a repeat array with a highly similar sequence is located, the example depicted in FIG. 3 is from a female individual). The peaks are characterized by plotting separately the histograms for arrays located on 4q, 10q, qA or qB (location-specific histograms, see FIG. 3 panels B-E).

Provided there is sufficient difference in size between repeat arrays to distinguish the peaks in the unsorted data, the mean length is measured within each peak on this entire set. This maximizes the number of determinations of the length for each peak. However, in a case where two distinctly located arrays (as shown on location-specific histograms) have similar lengths, the length of each array should be determined using only the measurements of arrays whose location could be discriminated. In the example depicted in FIG. 3, the two shorter peaks and the two longer ones are overlapping (FIG. 3, panel A). Therefore, average lengths were measured on the 4q-specific and 10q-specific data sets, in which the two peaks for each chromosome are clearly distinguishable (FIG. 3, panels B and C).

One important tunable parameter of the test is the number of signals used in the analysis. Indeed, this number can be virtually unlimitedly increased by increasing the number of slides used. If after a first analysis, the number of signals is for some reason deemed insufficient, it is straightforward to hybridize and analyze additional slides. Some possible reasons for this are the will to enhance the précision of the measurement or to take in account a possible mosaicism.

Indeed, the precision of the calculation of the mean is linked to the number of signals used in this calculation (more specifically, it is proportional to 1/(square root(n)) where n is the number of signals). The maximum error on the number of repeat units is the integer immediately above the (maximum error on mean size)/(size of one repeat) ratio. In some cases, one may tolerate an uncertainty on the number of repeat units. However, in other cases, e.g. when an array with a borderline number of repeat has been detected, especially on a 4qA chromosome) it may be necessary to determine reliably the exact number of repeat units. In this case, signal acquisition and analysis may be repeated until the number of signals is sufficient for the maximum error on the calculated mean to be less than the size of one repeat.

Increasing the number of signals may also be necessary when a case of mosaicism is suspected. Indications for the existence of a mosaic may be given either by clinical and familial data, or by one of the histograms, whether of unsorted or location-specific data. In the latter case, the indications include an un expected number of peaks.

3. Experimental Procedures 3.1 DNA Preparation and Molecular Combing

Human lymphoblastoid cell lines GM17724 and GM17939 were obtained from the Coriell Cell Repository (ccr.coriell.org) and cultivated according to provider's instructions. Human normal and FSHD blood samples were collected at the hospital La Timone-enfants (Assistance Publique/Hopitaux de Marseille). Written consent was obtained from patients to participate in this study. Peripheral blood monocytic cells were purified using standard procedures, by red blood cell lysis.

DNA was extracted by the standard procedure described in Lebofsky and Bensimon, 2006. Briefly, cells were resuspended in PBS at a concentration of 107 cells/mL. The cell suspension was mixed thoroughly at a 1:1 ratio with a 1% w/v solution of low-melting point agarose (Nusieve GTG, ref. 50081, Cambrex) prepared in PBS, at 50° C. 100 µL of the cell/agarose mix was poured in a plug-forming well (BioRad, ref. 170-3713) and left to cool at least 30 mini at 4° C. Agarose plugs were incubated overnight at 50° C. in 250 µL of a 0.5M EDTA (pH 8), 1% Sarkosyl, 250 µg/mL proteinase K (Eurobio, code: GEXPRK01) solution, then washed twice in a Tris 10 mM, EDTA 1 mM solution for 30 in at room temperature. Plugs were then melted at 68° C. in a MES 0.5 M (pH 6) solution for 20 min, and 2 units of beta-agarase (New England Biolabs, ref. M0392S) was added and left to incubate overnight at 42° C. The DNA solution was then poured in a Teflon reservoir and Molecular Combing was performed using the Molecular Combing System (Genomic Vision S.A., Paris, France) and Molecular Combing coverslips (20 mm×20 mm, Genomic Vision S.A., Paris, France). The combed surfaces were dried for 6 hours at 60° C.

3.2 Hybridization, Detection and Analysis

Subsequent steps were also performed essentially as previously described in Lebofsky and Bensimon, 2006. Briefly, a mix of labelled probes (250 ng of each probe, see below for details regarding probe synthesis and labelling) were ethanol-precipitated together with 10 µg herring sperm DNA and 2.5 µg Human Cot-1 DNA (Invitrogen, ref. 15279-011), ressuspended in 20 µL of hybridization buffer (50% formamide, 2×SSC, 0.5% SDS, 0.5% Sarcosyl, 10 mM NaCl, 30% Block-aid (Invitrogen, ref. B-10710)). The probe solution and probes were heat-denatured together on the Hybridizer (Dako, ref. S2451) at 90° C. for 5 min and hybridization was left to proceed on the Hybridizer overnight at 37° C. Slides were washed 3 times in 50% formamide, 2×SSC and 3 times in 2×SSC solutions, for 5 min at room temperature. Detection antibody layers are described in tables 1 and 2. Antibodies were diluted in Block-Aid as indicated in the table. For each layer, 20 μL of the antibody solution was added on the slide and covered with a coverslip and the slide was incubated in humid atmosphere at 37° C. for 20 min. The slides were washed 3 times in a 2×SSC, 1% Tween20 solution for 3 min at room temperature between each layer and after the last layer. The slide was dried in successive 70%, 90% and 100% ethanol solutions prior to mounting with Vectashield (Abcys, code: H-1000). Slides were then observed using conventional epifluorescence microscopes, all signals of interest were digitalized using a CCD camera (CoolSNAP HQ, Roper Scientific), and measurements of distances were performed manually using ImageJ [rsbweb.nih.gov/ij/] or JMeasure (Genomic Vision S.A., Paris, France) software. The type of locus (chromosome and haplotype) was assessed manually by comparing the observed motif with the predicted motifs and all the information (measurements and manual assessment of locus type) was recorded in a Microsoft Excel® file for further analysis. The analysis is described in detail elsewhere in this document.

TABLE 1

List of antibodies and other hapten-binding molecules used for the detection of probes.

| Description | Abbreviation | Supplier |
|---|---|---|
| Streptavidin, coupled to Alexa Fluor 488 | Strep/A488 | Invitrogen |
| Rabbit anti-streptavidin Coupled to biotin | Rb anti-strep/biotin | Rockland |
| Streptavidin, coupled to Alexa Fluor 594 | Strep/A594 | Invitrogen |
| Mouse anti-dig Coupled to Texas Red | M anti-DIG/TR | Jackson Immuno Research |
| Goat anti-mouse Coupled to A594 | G anti-M/A594 | Invitrogen |
| Rabbit Anti-A488 | Rb anti-A488 | Invitrogen |
| Mouse anti-DIG Coupled to AMCA | M anti-DIG/AMCA | Jackson Immuno Research |
| Rat anti-Mouse Coupled to AMCA | Rt anti-M/AMCA | Jackson ImmunoResearch |
| Goat anti-Rat Coupled to A350 | G anti-Rt/A350 | Jackson ImmunoResearch |
| Goat anti-Rabbit Coupled to A488 | G anti-Rb/A488 | Invitrogen |
| Goat anti-streptavidin Coupled to biotin | G anti-strep/biotin | Jackson ImmunoResearch |

3.3 Synthesis and Labelling of Probes

The coordinates of all the probes (relative to the NCBI build 36.1 Human reference sequence where possible, or to a Genbank sequence) are listed in table 3.

The Dee and Zee probes, containing each half of the D4Z4 repeat sequence (see description) were obtained by de novo synthesis and inserted in pJ56 plasmid (DNA2.0 Inc., Menlo Park, Calif., USA). Two point mutations were introduced relative to the reference sequence in the overlap of the two probes (G>A and C>G at positions 1659 and 1582 of the Dee probe and at the corresponding positions in the Zee probe) in order to allow for the reconstitution of the whole repeat sequence by introducing unique EcoRI and NotI sites. The whole repeat sequence ("repeat probe") was obtained by excision of the Zee sequence from its plasmid and ligation in the Dee-carrying plasmid. Given the high GV content, the Dee, Zee and repeat probes were labelled only with modified dCTP (dCTP-biotin and/or dCTP-A488).

TABLE 2

Composition of the 3 layers for the detection of probes by fluorescence. The dilution for each detection agent is indicated in brackets. The abbreviations refer to table A.

| | $1^{st}$ layer | $2^{nd}$ layer | $3^{rd}$ layer |
|---|---|---|---|
| 2-color scheme | | | |
| Biotin/green | strep/A488 (1/25) | Rb anti-strep/biotin (1/50) | strep/A488 (1/25) |
| Dig/red | M anti-DIG/TR (1/25) | G anti-M/A594 (1/25) | — |
| 3-color scheme | | | |
| Dig/blue | M anti-DIG/AMCA (1/25) | Rt anti-M/AMCA (1/25) | G anti-Rt/A350 (1/25) |
| A488/green | Rb anti-A488 (1/25) | G anti-Rb/A488 (1/25) | |
| Biotin/red | strep/A594 (1/25) | G anti-strep/biotin (1/25) | strep/A594 (1/25) |

The 4q- and 10q-chromosome specific probes were produced by long-range PCR using LR Taq DNA polymerase (Roche, kit code: 11681842001) using the primers listed in table 4 and the fosmids listed in table 3 as template DNA. PCR products, each approximately 2.5 kb long, were ligated in the pNEB193 plasmid (New England Biolabs Inc., Beverly, Mass., USA). The two extremities of each probe were sequenced for verification purpose. The apparent 5 kb (10q1-4), 7.5 kb (4q1) and 10 kb 54q2-4) probes are mixes of two, three or four adjacent 2.5 kb probes.

The beta-satellite probe is a plasmid containing ten repeats of the 68-bp satellite sequence.

TABLE 3

Coordinates of the designed probes. The reference for coordinates is indicated above the corresponding probes. For chromosomes 4 and 10, coordinates refer to build 36.1 of the NCBI Human reference sequence. For probes where this was not possible (qA regions do not belong to the reference sequence) or could be ambiguous, the Genbank accession number for the reference sequence is indicated.

| Probe | start | end |
|---|---|---|
| ref.: Chr. 4 | | |
| 4q1 | 191089412 | 191096843 |
| 4q2 | 191106888 | 191116775 |
| 4q3 | 191128570 | 191138567 |
| 4q4 | 191148576 | 191158554 |
| qB1-3 | 191252023 | 191253372 |
| qB1-4 | 191248879 | 191252040 |
| Ref.: U74496.1 | | |
| qA1 | 2756 | 3556 |
| qA2 | 8723 | 10672 |
| Ref.: U85056.1 | | |
| Deezee | 24213 | 27507 |
| Dee | 24213 | 25948 |
| Zee | 25763 | 27507 |
| ref.: Chr.10 | | |
| 10q1 | 135247926 | 135252909 |
| 10q2 | 135257958 | 135262966 |
| 10q3 | 135267992 | 135272976 |
| 10q4 | 135278058 | 135282988 |

The qA- and qB-specific probes were produced by long-range PCR using the primers listed in table 4 and DNA extracted by conventional methods from a patient blood sample collected at the hospital La Timone as template DNA. PCR products, were ligated in the pNEB193 plasmid (New England Biolabs Inc., Beverly, Mass., USA). The two extremities of each probe were sequenced for verification purpose. The qB probes qB1-3 and qB1-4 are adjacent and hybridize as a single 5 kb-probe due to internal repeats in the sequence.

In control experimens where probes were labelled differently, no significant cross-hybridization of 4q probes with 10q probes or of qA probres with qB probes was observed.

TABLE 4

Primer sequences used for the synthesis of probes by long-range PCR.

| Probe | PCR | Forward Primer | Reverse Primer | Template DNA |
|---|---|---|---|---|
| qA1 | qA1 | CCTTTGTCGCTTCAAACACC | CATTCCGAGACAGAAAGAGGA | Patient DNA |
| qA2 | qA2 | CGTTGATGTCTCCACCTCTG | TCACACAAAGCTATAAGGACTGC | Patient DNA |
| qB1 | qB1-3 | AGTTCCCCAACGGGACAG | GGCAAGGACTTCATGCCTAA | Patient DNA |
|  | qB1-4 | CGCCTGTAATTCCTGCATTT | CTGGGTGGACTCTGCTGTG | Patient DNA |
| 4q1 | 4q1-1 | CCCCACAATATCACCCCTTA | AGGTCTAGCATGGGCATAG | G248P85948G12 |
|  | 4q1-2 | GCCCCATGCTAGACCTACTG | TGAGAGTGATTTCAGCTTGACAG | G248P85948G12 |
|  | 4q1-3 | TGTCAAGCTGAAATCACTCTCAA | TGTGTATTCCCAGGCCTCTC | G248P85948G12 |
| 4q2 | 4q2-1 | GGAGTGCAGTGACATGATCG | TGCTGGGATTACAGGTGTGAG | G248P85948G12 |
|  | 4q2-2 | CTGTAATCCCAGCACTTTGG | CCAGAATTGACTTTTACTCCTTTATAC | G248P85948G12 |
|  | 4q2-3 | GGAGTAAAAGTCAATTCTGGCATC | ATCAAGGTGCATAACACATGGA | G248P85948G12 |
|  | 4q2-4 | TCCATGTGTTATGCACCTTGAT | CACTGGTGCAATGGATAACG | G248P85948G12 |
| 4q3 | 4q3-1 | GTGGTTTCGGTTCCCAACTA | ATTTTCTGTGGCAACCCTGT | G248P800659G7 |
|  | 4q3-2 | ACAGGGTTGCCACAGAAAAT | TTTGTGGACTGTGGTTTGTTAGA | G248P800659G7 |
|  | 4q3-3 | TCTAACAAACCACAGTCCACAAA | TGTGGCATCCAGTATATTCAGTG | G248P800659G7 |
|  | 4q3-4 | CACTGAATATACTGGATGCCACA | GTGCCCATGTATTTCCCAAT | G248P800659G7 |
| 4q4 | 4q4-1 | TCCCACCAACAGTGTAAAAGC | TTTTCTTAGCTGGGGCTGAA | G248P800659G7 |
|  | 4q4-2 | TTCAGCCCCAGCTAAGAAAA | TCCTGAGCCATAGCTCTCAGT | G248P800659G7 |
|  | 4q4-3 | ACTGAGAGCTATGGCTCAGGA | AGTGCCCCATAAGCACAGAC | G248P800659G7 |
|  | 4q4-4 | GTCTGTGCTTATGGGCACT | GGATCAGGCCCAGGATCT | G248P800659G7 |
| 10q1 | 10q1-1 | CCAAAGACAAAAACCACATGAT | TAAATTCCAGACAGCGCAGA | G248P81988E3 |
|  | 10q1-2 | GTCTGCGCTGTCTGGAATTT | GGTGGTCATAGTGGGGGATT | G248P81988E3 |
| 10q2 | 10q2-1 | TTGCCTAATCCATGGTCACA | GAAGACCTGACCAACACAATCA | G248P81988E3 |
|  | 10q2-2 | TGATTGTGTTGGTCAGGTCTTC | AAAAGAAAACCGTCTAAGAGAGAGG | G248P81988E3 |
| 10q3 | 10q3-1 | TAAGGCTTGTGATGCATTGG | GGAAGGCAATATCCATGATGTTA | G248P81988E3 |
|  | 10q3-2 | TAACATCATGGATATTGCCTTCC | ACCCTTTGGCACAGAGCTT | G248P81988E3 |
| 10q4 | 10q4-1 | CATCTTCATCAGAGAAAGCCAAG | TGGGCTAGGCCCAAAGTA | G248P81988E3 |
|  | 10q4-2 | ACTAGGCTCAGCTAAGGTTTTCAC | AGATGCAAACGGCTGTGAG | G248P81988E3 |

The primers contain restriction sites in 5' of the sequence to be amplified for cloning purpose. PCR products hybridizing adjacently and thus constituting the same probe are grouped and named identically except for the number following the dash. For fosmids used as template DNA, the reference name of the fosmid in the UCSC Human Genome Browser database (genome.ucsc.edu) is indicated.

TABLE 5

Mixes used in replacement of the dNTP mix of the random priming kit for labelling with alternative haptens. The concentrations indicated are the final concentration in the labelling reaction. The non-labelled dNTPs and the labelled dNTP were added together in replacement of the provided dNTP mix intended for labelling with dCTP-11-biotin

| Labelling | Non-labelled dNTPs | Labelled dNTP |
|---|---|---|
| dUTP-dig | dATP, dCTP, dGTP 40 μM each dTTP 20 μM | Dig11-dUTP 20 μM |
| dUTP-A488 | dATP, dCTP, dGTP 40 μM each dTTP 20 μM | A488-5-dUTP 20 μM |

Labelling of the probes was performed using conventional random priming protocols. For dCTP-biotin labelling, the Random Priming kit (Invitrogen, code: 18094-011) was used according to the manufacturer's instruction, except the labelling reaction was allowed to proceed overnight. For other labels (dUTP-digoxygenin, dUTP-A488, dCTP-A488), the dNTP mix from the kit was replaced by the mix specified in table 5. 200 ng of each plasmid was labelled in separate reactions. The reaction products were visualized on an agarose gel to verify the synthesis of DNA.

TABLE 5-continued

Mixes used in replacement of the dNTP mix of the random priming kit for labelling with alternative haptens. The concentrations indicated are the final concentration in the labelling reaction. The non-labelled dNTPs and the labelled dNTP were added together in replacement of the provided dNTP mix intended for labelling with dCTP-11-biotin

| Labelling | Non-labelled dNTPs | Labelled dNTP |
|---|---|---|
| dCTP-A488 | dATP, dTTP, dGTP 40 μM each dCTP 20 μM | A488-7-OBEA-dCTP 20 μM |

4. Results

Figure 1:
FIG. 1. Example of D4Z4, 4q, 10q, qA and qB probes that can be used according to the invention. The three hybridization patterns expected on chromosome 4q (qA and qB haplotypes) and chromosome 10q (the telomeric region of which is identical to chromosome 4qA) are shown. The localization probes which form a signature specific for chromosomes 4q/10q or for the qA/qB haplotypes are revealed in red (digoxygenin labelling, white boxes) and the probe which is specific for D4Z4 is revealed in green (biotin labelling, black boxes). The sizes (rounded to the nearest kb) of the localization probes and of the gaps between two consecutive localization probes are indicated respectively below and above each diagram.
Figure 1:
Figure 1:
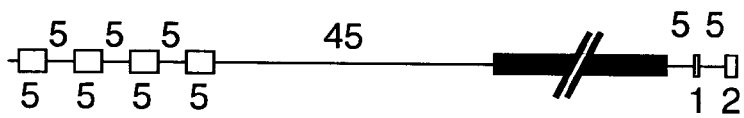
Figure 1:
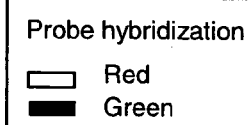
Figure 2:
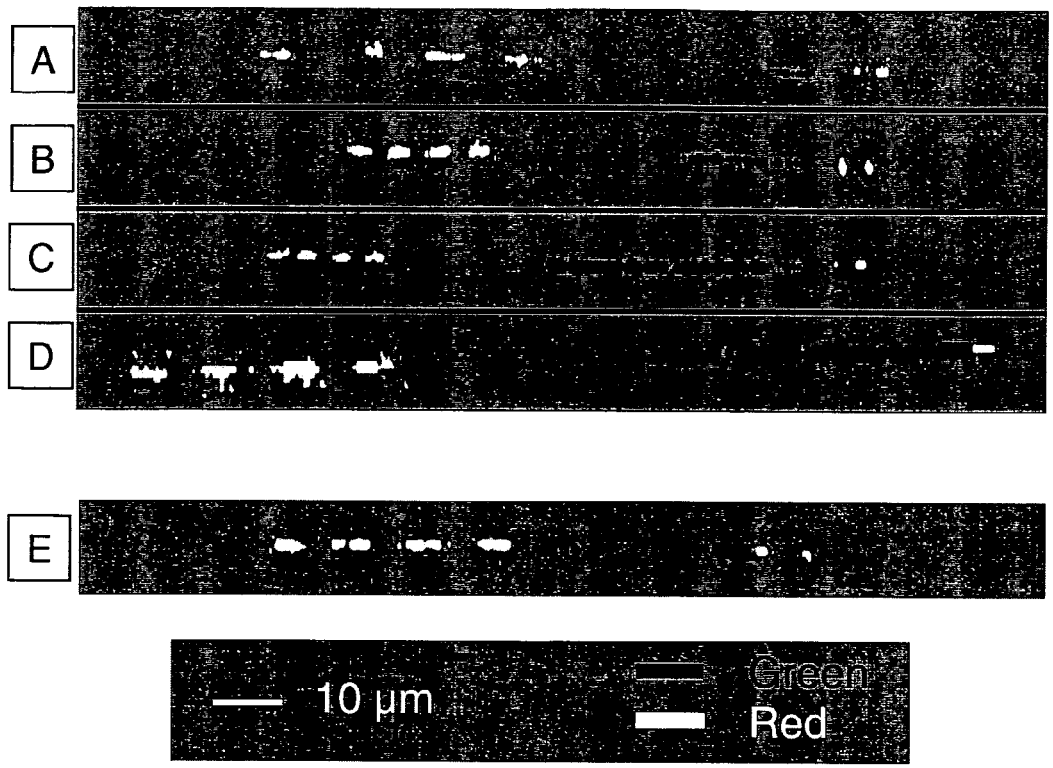
FIG. 2. Hybridization signals observed on sample from Patient 1. For reproduction purposes, contrasts were enhanced, colors were modified (the normally black background from microscope images is gray, the green signals are shown in black and the red signals in white), and the vertical scale was stretched twice (the aspect ratio is thus not conserved, but lengths are unchanged relative to the reference scale presented).

The set of probes used to perform the method of the invention is shown schematically on FIG. 1. Specific details concerning probe position and synthesis is available in the experimental procedures section. The repeat probe was labelled with biotin and detected in green and the location probes were labelled with digoxygenin and detected in red. Typical signals, obtained from the sample of patient 1 (described below) are shown in FIG. 2, panel A-D. The beta-satellite probe was generally not used due to the possible confusion with the qB probe. However, test hybridizations were made with this probe. A typical signal is shown in FIG. 2, panel E, from the same allele as FIG. 2 panel A.

The process for calculating the number of repeat arrays is detailed below for one of the samples analyzed. This sample was from a blood sample of a female FSHD patient, and treated as described in the experimental procedures section. The analysis reported here corresponds to the "relaxed approach—intact signals" as described below.

The length of every detected intact D4Z4 repeat array (i.e. repeat arrays with location probes detected on both sides, thus guaranteeing that there was no break within the array) was measured. The resulting histogram is shown on FIG. 3, panel A. Four modes, i.e., 4 local maximums, clearly appear at the following lengths on this histogram: 14.9 kb, 28.1 kb, 70.1 kb, and 87.5 kb. These modes approximately correspond to the following number of D4Z4 repeat units: 5, 9, 22, and 27 respectively.

Similar histograms were established by compiling the length of every detected D4Z4 repeat array associated with hybridization signals corresponding to the different location probes; among the 114 measures compiled in the histogram of FIG. 3, panel A, the ones which correspond to D4Z4 specific hybridization signal which were associated with a signature specific for chromosome 4q, chromosome 10q, chromosomes of the qA haplotype or chromosomes of the qB haplotype are shown respectively on FIG. 3, panels B to E.

On the histogram corresponding to the D4Z4 repeat arrays located on chromosomes 4q shown in panel B, two modes clearly appear at the following lengths: 14.9 kb, and 87.5 kb. They approximately correspond to the following number of D4Z4 repeat units: 5 and 27 respectively.

On the histogram corresponding to the D4Z4 repeat arrays located on chromosomes 10q shown in panel C, two modes clearly appear at the following lengths: 28.1 kb and 71.0 kb. They approximately correspond to the following number of D4Z4 repeat units: 9 and 22 respectively.

On the histogram corresponding to the D4Z4 repeat arrays located on chromosomes of the qA haplotype shown in panel D, three modes clearly appear at the following lengths: 14.9 kb, 28.1 kb and 71.0 kb. They approximately correspond to the following number of D4Z4 repeat units: 5, 9 and 22 respectively.

On the histogram corresponding to the D4Z4 repeat arrays located on chromosomes of the qB haplotype shown in panel E, a single mode clearly appears, at a length of 87.5 kb. This mode approximately corresponds to 27 D4Z4 repeat units.

The different modes identified on each of the histograms shown on FIG. 3, as well as the corresponding numbers of D4Z4 repeat units are recapitulated in table 6 below.

The following conclusions can be drawn from table 6:
The analyzed genomic DNA contains:
one 4qB allele, which carries 27 D4Z4 repeat units (the corresponding mode is present for both the 4q and the qB hydribization signals);

two 10q alleles, which carry 9 and 22 D4Z4 repeat units respectively (the two corresponding modes are present for both the 10q and qA hydribization signals); and
one 4qA allele, which carries 5 D4Z4 repeat units (the corresponding mode is present for both the 4q and qA hydribization signals).

TABLE 6

Characterization of the different modes identified on the histograms of FIG. 3. For each mode, both the length in kb of the D4Z4 repeat array and the number of repeat units (in brackets) are indicated.

| | | | | |
|---|---|---|---|---|
| D4Z4 | 14.85 (5) | 28.1 (9) | 71.0 (22) | 87.5 (27) |
| 4q | 14.85 (5) | | | 87.5 (27) |
| 10q | | 28.1 (9) | 71.0 (22) | |
| qA | 14.85 (5) | 28.1 (9) | 71.0 (22) | |
| qB | | | | 87.5 (27) |

The above approximations may however be given with more certainty as intervals. It is necessary to estimate the average size of the measures within a peak and standard deviation of measurements in order to do so. For each peak, the standard deviation of the measurements was estimated to be sd=1 kb+0.1 L where L is the length of the considered mode, in accordance with our experience with molecular combing measurements. Virtually all measurements (>95%) for a given allele should fall within the [L−2.sd; L+2.sd] int. Since these intervals do not overlap with any other for the 2 shorter peaks ([9.9-19.8] and [21.8;37.6] respectively), all measurements of intact D4Z4 repeat arrays within one of these intervals were considered to belong to these alleles, even if their precise location could not be ascertained from the location probes. The third and fourth peaks, however, have overlapping intervals ([54.8-87.1] and [68.0;106.9] respectively), so the same method could not be applied. However, since one of these peaks is a 4q allele and the other a 10q allele, all intact measurements of D4Z4 repeat arrays identified as belonging to chromosome 10 in the [54.8-87.1] interval (respectively belonging to chromosome 4 in the [68.0;106.9] interval) were considered to belong to the long 10q and the long 4q allele, respectively. The same separation could have been obtained by using qA and qB information, or both haplotype and chromosome information, with little difference in the result The number of measurements using these criteria and the resulting average lengths are summarized in table 7.

TABLE 7

Allele size determination for the 4 alleles of patient 1. Indicated are the average size in kb, the number n of measurements used for the calculation of the average, the 95% confidence interval (CI) for the size in kb and the confidence interval (>95%) for the repeat number.

| Allele | Average size (kb) | n | 95% CI for size (kb) | CI for repeat number |
|---|---|---|---|---|
| 4qA | 14.9 | 90 | [14.4; 15.5] | 4-5 |
| 10q - short | 29.44 | 134 | [28.8; 30.1] | 8-10 |
| 10q - long | 67.01 | 54 | [64.9; 69.1] | 19-21 |
| 4qB | 84.59 | 54 | [82.0; 87.1] | 24-27 |

The maximum error on the average length computed this way may be defined as $2.sd/\sqrt{n}$, where n is the number of measurements considered. There is a 95% probability that the actual repeat array lengths falls within this interval. Resulting 95% confidence intervals are summarized in table 7. The repeat number is estimated by L/3.3, where L is the computed average length. The minimum and maximum number of repeat arrays was chosen by rounding to the integer immediately below the minimum average length/3.3 and above the maximum average length, respectively. Given that this broadens the confidence interval, the probability for the actual repeat number to fall within this interval is greater than 95%. Confidence intervals are summarized in table 7.

TABLE 8

Results from the described method and from other methods for patient blood samples and reference cell lines. qA/qB haplotypes were only determined by molecular combing. For patients samples, a dash indicates an allele longer than 50 kb, for which the number of repeats could not be established. The question mark for patient 4 indicates an allele that could not be detected by southern blotting.

| Patient | Allele | Molecular Combing Repeats | Southern Blot Repeats |
|---|---|---|---|
| 1 | 4qA | 4-5 | 4-5 |
|   | 4qB | 24-27 | — |
|   | 10q | 8-10 | 8-9 |
|   | 10q | 19-21 | — |
| 2 | 4qA | 6-8 | 8 |
|   | 4qA | 31-34 | — |
|   | 10q | 10-12 | 12 |
|   | 10q | 23-26 | — |
| 3 | 4qA | 2-4 | 4 |
|   | 4q ? | 85-91 | — |
|   | 10q | 17-21 | — |
|   | 10q | 24-27 | — |
| 4 | 4qA | 8-10 | 8 |
|   | 4qA | 21-27 | — |
|   | 10q | 6-8 | ? |
|   | 10q | 17-21 | — |

| Cell Line | Allele | Molecular Combing Repeats | CCR repeats |
|---|---|---|---|
| GM17724 | 4qA | 7-9 | 6 |
|   | 4qB | 18-20 | 18 |
|   | 10q | 17-19 | 16 |
|   | 10q | 25-28 | 25 |
| GM17939 | 4qA | 4-6 | 3 |
|   | 4qA | 30-34 | 33 |
|   | 10q | 14-16 | 15 |
|   | 10q | 25-30 | 26 |

The same procedure was performed for several other samples: two cell lines from the Coriell Cell Repository (CCR): GM17724 and GM17939, carrying FSHD alleles and four patients. Results are given in table 8. As a comparison, results obtained from other methods are also listed in table 8 (last column). For the CCR cell lines, results show the determination of number of repeats for chromosomes 4 and 10 published by the CCR. For the patient samples, results from conventional southern blotting procedures are given. In the latter case, alleles longer than 50 kb (approx. 15 repeat units) could not be separated and their size was not estimated.

As is obvious from table 8, our results are in good agreement with otherwise established measurements of the number and type of D4Z4 repeats. In the case of the CCR, it should be noted that most often the assessment by the CCR does not fall within our confidence interval. This is probably due to a difference in references, such as a variant repeat that is not counted by the CCR assessment but that we detect as a repeat unit. Accordingly, the deviation between both our results are always oriented the same way (the CCR underestimates the number of repeats compared to our results). It should also be mentioned that for the GM17939 cell line, the only sample in our results corresponding to a male individual, a supplementary peak was observed around 35 kb, which was never associated with location probes and thus was assumed to correspond to a repeat array on chromosome Y. This repeat array is not mentioned in the CCR documentation.

5. Possible Extensions or Variations
5.1 Location Probe Design
5.1.1 General Rules The set of probes we designed can be replaced by any set of probes which allows to distinguish 4q and 10q chromosomes and 4qA and 4qB haplotypes. Infinite combinations are possible, provided they obey certain principles:

1) Probes must either be or have position specificity. The term "location-specific" designates herein probes that, in the specific experimental conditions used, will hybridize with one of the chromosomes (e.g. chromosome 4 or 10) or with one of the haplotypes (e.g. the qA or qB haplotype) and not with the other one. The term "position specificity" designates herein probes that hybridize with both chromosomes (e.g. chromosomes 4 and 10) or both haplotypes (e.g. both the qA and the qB haplotypes), albeit in different positions relative to the repeat array or relative to another probe.

2) Each chromosome or haplotype must carry a specific signature, ie a succession of probes in which the length and "color" of probes and relative position of probes are unique and distinguishable from the succession of probes on the other chromosome or haplotype, in the experimental conditions used (e.g. distances must be distinguished at the resolution of the measurement method used).

3) In a technique where the integrity of the locus is not fully controllable and breaks occur at random locations, such as Molecular Combing, it is important to keep the probes as close as possible to the repeat array in order to increase the probability for each copy of the locus in one analysis to be complete.

4) Robustness of the method regarding experimental conditions (which may influence sequence specificity of the hybridization, resolution, etc) and genetic variations in the population (e.g. non-pathogenic rearrangements or sequence variations in the vicinity of the FSHD locus) will increase if there is redundancy in the signatures, i.e. if one chromosome or haplotype may carry several specific signatures.

Following these rules, the man skilled in the art may design probe sets which are suitable for the specific technique he uses, taking into account parameters such as precision of the measurements, sequence specificity of the hybridization, number of different labels (e.g. fluorophores or haptens detected by fluorescence) affixable to the probes, etc. Some examples of alternative designs follow. It should be noted that the strategies described rely on the most generally accepted published sequences for the regions involved. If more complete or more exact data should become available, the man skilled in the art may very well take profit of the new data to adapt the probe design by following the principles described above and exemplified below.

5.1.2 4qA/4qB (FIG. 4)

The sequence differences between these haplotypes, as can be inferred from the published sequences of these haplotypes, are the following (see FIG. 4, panel A):

on the qA haplotype, a repeat array of a 68 base pair beta-satellite sequence is located immediately downstream of the D4Z4 repeat array (see below for a description of the termination of the repeat array in qA versus qB). The total length of this beta-satellite repeat array is not known precisely. According to our observations, it extends over a region of about 5 kb. However, some authors report it as being 8 kb long (Lemmers et al., 2002). This beta-satellite repeat array is followed by a repeat array of about 1 kb of telomeric (TTAGGG)$_n$ repeat units. These two repeat arrays are not present on the qB haplotype in the immediate vicinity of D4Z4;

on the qB haplotype, a sequence of about 6 kb is present immediately downstream of the D4Z4 repeat array. This sequence, termed qB1 is not present on the qA haplotype in the vicinity of the D4Z4 repeat array. However, one 300 bp-stretch within this sequence is present on both qB (500 bp downstream of the telomeric end of the D4Z4 repeat array) and on qA in the inverse orientation (at two loci, respectively about 1.5 kb and about 10 kb downstream of the telomeric end of the beta-satellite repeat array. Besides, the qB1 sequence comprises internal inverted repeat units: bases 1-1500 of qB1 correspond to the inverted copy of bases 3800-5000, with the insertion of the 300 bp-stretch mentioned above (see FIG. 4);

on the qA haplotype, two sequences of approximately 750 bp and 1900 bp are located respectively 2.5 kb and 8.5 kb downstream of the telomeric end of the beta-satellite repeat array. These sequences, termed qA1 and qA2 respectively are not present on the qB haplotype, except from the aforementioned 300 bp-stretch, which is found within the qA2 sequence and in inverse orientation in the qB-specific sequence;

it should also be noted that the repeat array is terminated differently in the qA and qB haplotypes, according to the published sequences. Indeed, the last repeat in the repeat array on the qA haplotypes is a variant D4Z4 repeat, termed pLAM (van Deutekom et al., 1993). The published sequence for pLAM (van Geel et al., 2002, genbank accession #U74497.1) shows a partial D4Z4 repeat extending over 1.9 kb, followed by a few short (<80 bp) repeat elements from the D4Z4 sequence separated by a few tens of base pairs of specific sequence, before the beginning of the beta-satellite repeat array additionally, if the hypothesis according to which the telomeric sequences on chromosomes of the 4qA haplotype are identical to those on chromosome 10 is true, the comparison of 4qB and 10 sequences shows an additional 10q- (and therefore 4qA-) specific sequence, which has no similarity with the 4qB telomeric end. This sequence, ~11 kb long, is in fact the prolongation of qA2. We term this sequence qA3.

5.1.2.a One-Color Designs (FIG. 4, Panels B and C)

If it is deemed preferable to keep only one label for all the location probes, only the lengths and relative positions of the localization probes can allow to distinguish two different signatures for the qA and qB haplotypes.

Molecular Combing along with our hybridization procedure allows detecting probes as small as a few hundred base pairs. However, below a few kb (~5 kb), the detection efficiency (ie the ratio of the number of actually detected probes/number of relevant loci present on the slide) drops significantly. Gaps between probes should be at least 4 kb wide to actually identify them as gaps. The standard deviation of the size measurement can be considered as the sum of a constant factor, in the order of magnitude of 1 kb, and a relative factor, approximately 0.1× (size of measured probe). Therefore, probes smaller than 2 kb can hardly be distinguished by their size, but a 2 kb- (sd=1.2 kb) and a 5 kb-probe (sd=1.5 kb) will appear as different in a majority of measurements.

The qB1 region is the only qB-specific region, so it is important to maintain at least one probe with high enough detection efficiency, ie greater than 5 kb. Therefore, covering the qB1 region with one probe seems a necessary common feature of any qA/qB probe design for Molecular Combing with the hybridization procedure described (FIG. 4, panel B). With the internal repeats of qB1, however, this does not necessarily require to use the whole qB1 region as the template for probes, as omitting bases 4000-6000 would still allow the probe to hybridize on 5 kb of the sequence (bottom option for qB in FIG. 4, panel B). Omitting bases 1-1500 of this region of about 6 kb would allow the probe to hybridize over the whole sequence except for the 300 bp stretch described above. This latter solution will allow hybridization of the probe over the 6 kb qB1 region, with an internal 300 bp-gap that will not impair detection or identification of the signal as a 6 kb-probe given its small size, and with no cross-hybridization on qA.

A probe covering the repeated beta-satellite sequence would necessarily hybridize over the whole beta-satellite repeat array, thus appearing as a ~5 kb probe, with significant variation in the population. Thus, it would hardly be distinguishable from a 6 kb qB1 probe if labelled with the same label, since both hybridize immediately downstream of the D4Z4 repeat array. Therefore, in a single-color scheme, it appears the only usable sequences specific of 4qA are qA1 and qA2. Given that their size, 800 bp and 1900 bp is not distinguishable with the procedure described, and that their detection efficiency is already impaired by their small size, it is preferable to optimize detection efficiency by covering the whole sequence for each probe (FIG. 4, panel B). It is obviously possible to use only one of the two probes instead of both probes, as this would generate a short (<2 kb) signal about 10-15 kb downstream from the telomeric end of the D4Z4 repeat array, easily distinguishable from the 6 kb-signal adjacent to the D4Z4 repeat array on qB. However, since detection efficiency is not 100% for these probes, the probability of detection at least one—which is sufficient to distinguish qA from qB—is higher when both probes are used.

Additionally, if the 10q published sequence is shown to reliably represent the 4qA sequence, the qA3 stretch may also be used. Any size of probe above 5 kb is detected efficiently, and the location of such a probe, at least 10 kb downstream of the D4Z4 repeat, will allow to distinguish it from the qB1 probe. For example, one may use a probe extending over 5 kb from the end of the 4qA/4qB shared sequences. This probe could be used along with or instead of the qA1 and qA2 probes.

If adaptations of the Molecular Combing technology, or related technologies where several physical distances can be measured on single molecules, have different characteristics in terms of detection efficiency, precision of measurement, resolution of probes, etc, the design of the localization probes may be significantly different.

For example, if a succession of three 1 kb-probes separated by 1 kb-gaps were readily distinguishable from a 5 kb-probe, it would be advisable to cover the qB1 region with such a succession of probes, and to use the beta-satellite repeat region on qA as its specific signature—potentially along with the qA1 and qA2 regions (FIG. 4, panel C).

Another option, if the detection efficiency of a 300 bp-probe is not an issue, would be to use the 300 bp sequence mentioned above as a single probe to distinguish qA from qB: indeed, this probe hybridizes about 500 bp from the telomeric end of the D4Z4 repeat array on qB, and about 1.5 kb downstream from the telomeric end of beta-satellite repeat array, or more than 6 kb downstream from the telomeric end of the D4Z4 repeat array, so its position relative to the D4Z4 repeat array could suffice to allow the distinction.

5.1.2.b Several-Color Designs

If several different labels may be used for the location probes, other options are possible to distinguish qA and qB. Obviously, using two colors would allow to use one or several probe(s) hybridizing with the beta-satellite repeat array on qA and one or several probe(s) hybridizing with the qB1 region together, provided the corresponding probes are labelled differently (and also differently from the repeat probe, see FIG. 4, panel D). These two probes would actually suffice to make the distinction between the qA and qB haplotypes, although it remains possible to use them along with qA1 and/or qA2. Naturally, other schemes are possible, and numerous valid options will arise if more colors are used. Inspired by the reasoning above, the man skilled in the art will easily achieve a design that optimizes the use of these colors.

It is also possible to achieve a close result by using only two labels, but allowing a combination of these two labels for the probes. For example, in our technique the labels used are biotin and digoxygenin, principally. It is possible, when labelling the probes by random priming or the like, to incorporate both labels. Alternatively, two separate reactions may be performed, followed by the mixing of digoxygenin- and biotin-labelled probes. Since several fragments, each typically a few hundred base pairs long, hybridize with large (>a few kb) target regions, it is possible to achieve the labelling of one region with two labels, which will appear as a superposition of colors after detection. This may be considered a "third" color as compared with the two "pure" colors.

In the example above, it would be possible to label for example the beta-satellite region with two colors, thus allowing the distinction between the single-label (e.g. biotin) repeat probe and the single-label (e.g. digoxygenin) qB1 probe. In this case, the length of the repeat array on a qA chromosome is determined as the difference between the biotin-labelled segment (representing the D4Z4 repeat array and the adjacent beta-satellites) and the digoxygenin-labelled segment (representing the beta-satellite repeat array alone). This indirect measurement of the repeat array length may however hinder the precision of this measurement.

5.1.3 4q/10q (FIG. 5)

Globally, according to the published data, the 4q and 10q telomeric regions are identical over a region comprising the D4Z4 repeat array, the downstream sequences (which are reportedly identical in 10q and in the 4qA haplotype), and upstream sequences over 45 kb (FIG. 5, panel A).

On the 10q chromosome, upstream of the common 4q/10q sequence is a stretch of 35 kb of sequences specific to 10q (ie not found on 4q in the region of about 100 kb upstream of the centromeric end of the D4Z4 repeat array), termed 10q1. Upstream of the 10q1 sequence is a stretch of about 7 kb which has multiple copies or inverted copies on the 4q chromosome.

On the 4q chromosome, upstream of the common 4q/10q sequence are, ordered from telomeric to the centromeric region, an inverted D4Z4 repeat, a specific region of about 10 kb (termed 4q1), a region of about 20 kb with copies or inverted copies of sequences also found on 10q (upstream of the 10q1 sequence), a specific sequence of about 20 kb (termed 4q2), a sequence of about 7 kb which is a copy of a sequence found on 10q upstream of 10q1 and a specific sequence of about 35 kb (termed 4q3). Upstream of the sequences described here are essentially sequence specific for each chromosome.

5.1.3.a One-Color Designs

Given the wide regions that are chromosome-specific, there are multiple possible designs for probes that should allow robust distinction between 4q- and 10q-located repeat arrays.

Among the options is the possibility to take profit of all four specific regions described above (4q1, 4q2, 4q3, 10q1). However, this design has two flaws: 1) in the case where a 10q locus is broken during the Molecular Combing process in the 10q1 region, leaving only ~10 kb of the 10q1 sequence, the signal will appear undistinguishable from a 4q locus broken between the 4q1 and 4q2 sequences, i.e. one 10 kb-probe separated by a ~45 kb-gap from the D4Z4 repeat array; and 2) the 10q1 and 4q3 probes have the same length. Thus, if in a rearrangement the 4q2 and 4q1 probes are lost, 10q and 4q chromosomes will display identical signals.

Single-color options we believe have the best predictable robustness are options where no probe on one chromosome matches—in size—a probe from the other chromosome. For reasons already mentioned, it is advisable to have several probes on each chromosome. In order to keep the code as compact as possible, we chose the minimum sizes that are both efficiently detected and easily distinguished, i.e. 5 and 10 kb. Gaps should follow the same rule, and accordingly we also chose gaps of 5 and 10 kb (FIG. 5, panel B).

For technical reasons, namely the difficulty to amplify part of the 4q-specific region by PCR, we eventually replaced the 10 kb-probe closest to the centromere on 4q by a 7.5 kb probe; the gap between this and the neighbouring probe was however kept at 10 kb. This illustrates the fact that variations on the described codes are possible and do not significantly modify the concept.

It would be possible to associate 5 kb probes with 10 kb gaps and 10 kb probes with 5 kb gaps. However, in this case, if for example one of the 10 kb probes is hybridized incompletely, over only 6 kb, the corresponding gap would extend to 9 kb, thus appearing like a 6 kb probe and a 9 kb gap, which could possibly be confused with the 5 kb probe/10 kb gap association. In a scheme where 5 kb probes and gaps are associated, as well as 10 kb probes and gaps, this is not likely to occur.

The "main" gap between the chromosome-specific probes and the D4Z4 repeat array is at least 42 kb long on chromosome 10q and 45 kb on chromosome 4q (due to the inverted D4Z4 repeat). Locating the probes immediately upstream of this gap would allow for the most compact code. However, the size of this "main" gap may also be used to distinguish 4q- and 10q-probes, for example if the fiber is broken and only the most proximal probe remains. Thus, we chose to keep a 45 kb gap on chromosome 10 but to set a ~65 kb gap on chromosome 4.

Naturally, even with one color there are infinite valid designs, which may be more suitable for other technologies or other experimental conditions if the technical specifications of the technology differ significantly from our implementation of Molecular Combing. By following the reasoning described above, it is easy to find a valid design.

Importantly, we have considered only regions where sequences are sufficiently divergent to obtain hybridization specificity of the probes. If it is possible to distinguish more subtle sequence divergences by the hybridization of probes, it is advisable to consider the region closer to the D4Z4 repeat arrays where subtle differences between 4q and 10q chromosomes exist as targets for designing probes, thus allowing for a more compact code.

5.1.3.b Several-Color Designs

If additional colors are available for the detection of probes, the possibilities are more numerous yet. One straightforward use of a third color would be to design one probe set with one color for one chromosome (e.g. red for 4q), another color for the other chromosome (e.g. green for 10q), while keeping one color for the repeat array (e.g. blue). It would then be best to keep a pattern of probes (e.g. four 5 kb probes separated by 5 kb gaps) in order to maintain robustness relative to non-specific hybridization and unexpected rearrangements (FIG. 5, panel C), but another option is to design one single probe on each of the chromosomes within the specific regions described above (FIG. 5, panel D). With this type of probe design, where the color alone is sufficient to distinguish the two chromosomes, it is possible to use DNA testing techniques where precise sequence length measurements are not possible.

5.2 D4Z4 Probes and Assessment of Repeat Copy Number (FIG. 6)

5.2.1 "Plain" Design (FIG. 6, Panel B)

The most straightforward approach to estimating the number of D4Z4 repeat units in a repeat array is to design a probe covering the whole sequence of a D4Z4 repeat unit (FIG. 6, panel A: "DZ" probe). This probe will hybridize as one segment covering the whole repeat array. If the (physical length)/(sequence length) ratio is known, which is the case with the Molecular Combing technique, the measurement of this segment will provide the length in kb of the repeat array, and dividing by 3.3 kb (the length of one repeat), the number of repeat units.

Some corrections may be factored in to add precision to this method of quantification of the repeat units. Indeed, as stated above, it is possible to have a non-integer number of repeat units. If one relies on the published data and the haplotype is determined, the length of the last, incomplete, repeat may be subtracted before the conversion from kb to number of repeat units. For example, a repeat array segment identified as being on a haplotype qA chromosome will contain (measured length of segment in kb−2 kb)/3.3 kb entire repeat units in addition to the pLAM sequence, since the D4Z4 probe will hybridize on ~2 kb of the pLAM sequence.

5.2.2 "One-Half" Design (FIG. 6, Panel C)

Some enhancements of the previous approach may be found in order to make the determination of the number of repeat units easier, more precise and/or more robust. In addition to these advantages, the approaches described below may also provide an insight on the physical organization of the repeat array, e.g. reveal the existence of inversely oriented repeat units. Besides, the direct counting technique described herein could also apply to other DNA testing techniques where the topology of the sequences is conserved over the region of interest but where precise sequence length measurements are not possible.

In the two alternatives and their variants described below, we have chosen to cover the D4Z4 sequence with two probes, termed Dee and Zee, covering respectively the centromeric and the telomeric region, over 1.7 kb (the probes have a slight sequence overlap over 100 bp in the center of the D4Z4 sequence).

In a first step, if only one color is kept to label the repeat array, it is possible to use only one of the probes, either Dee or Zee in the hybridization. This leads to the repeat array being detected as a succession of short 1.7 kb probes separated by 1.5 kb gaps. Assessment of the repeat copy number may be achieved by counting the number of probes. Alternatively, or as a control, the physical length of the array may be measured by measuring the distance between the beginning of the first probe to the end of the last one. As in the previous setup, the number of repeat units may be deduced from this measurement. Also as previously underlined, some correction factors may be computed. For example, the Zee probe would not hybridize on the 1.5 kb at the centromeric end of the repeat, and would end before the pLAM sequence.

This direct counting technique may also provide some information on the physical organization of the repeat array: a succession of two differently oriented repeat units within the array would appear either as a 3.4 kb probe or as a 3 kb gap, provided the precision of measurement of the technique is sufficient to distinguish those from 1.7 kb probes or 1.5 kb gaps. The orientation of every repeat unit in the array is then deduced from the positions of the successive inversions. It should however be emphasized that this approach may not allow to distinguish an inversion in the sequence from a deletion of a fraction of a repeat or the insertion of unrelated sequences.

5.2.3 "Two-Halves" Design (FIG. 6, Panel D)

In a second step, the two halves of the D4Z4 sequence may be covered by one probe each, with different colors, e.g. Dee detected in red and Zee in green. In this setup, the repeat array will appear as a succession of red and green 1.7 kb probes, with a slight overlap over 100 bp (see FIG. 6). In a similar fashion to the previous setup, the repeat units may be directly counted by counting the number of red-green motifs, and/or by measuring the total length of the repeat array. Also, inversions of repeat units will be detected as 3.4 kb red or green segments. Here, there is some added robustness as compared to the previous setup towards events such as internal deletions or insertion of unrelated sequences, since these would appear as inconsistencies in the count and orientation of the repeat units or gaps, respectively. Also, compared to the "plain" design where one probe covers all the sequence, there is added robustness towards non-specific hybridization, since the repeat array motif is more specific.

5.2.4 Variations of the Repeat Probe Design

Variations on the designs described above may include either choosing probes of different sizes, or varying the overlap size (up to the repeat length and down to zero), introducing a gap between the two probes, or splitting the D4Z4 sequence differently (i.e. choosing another "starting base" for D4Z4). This would not bring major changes to the concept. Care should be taken not to design probe too small for efficient detection and also not to include internal repeat units within the D4Z4 sequence in two different probes to avoid cross-hybridization. In our design, the main internal repeat units are all included in the Dee probe.

Further detailing of the D4Z4 sequence would probably prove difficult to implement with the technical characteristics of the Molecular Combing technique in our experimental conditions, since probes would be smaller than 1.7 kb, thus detected less efficiently and would probably become difficult to resolve. However, with higher resolution techniques or implementations of Molecular Combing that would enhance resolution and detection of small probes, the man skilled in the art would easily adapt this design to take maximum profit of the technical characteristics of the technique. In this case, if more than two segments are used to cover the D4Z4 repeat unit, it is advisable to use more than two different colors (or mixes of colors) to label the segments.

Whether one or two—or more—colors are used to label the D4Z4 repeat array, it is advisable not to use these colors for any of the location probes, in order to exclude any misleading interpretation e.g. in the event of an unexpected rearrangement. If only two colors overall are to be used, the one-color designs for the location probes and the plain design or one-half design for the repeat probe in another color seems the best alternative. If three colors (or two colors and a mix of the two colors) are used, one may chose to either keep two colors for the location probes for the reasons stated above or to keep the one-color designs for the location probes and to adopt the two-halves design for the repeat array. If information provided from both methods are necessary, it is obviously possible to gather data from two separate hybridizations with different designs. With four colors, it is possible to implement both the two-color designs for the location probes and the two-halves design, thus reaching an optimal level of detail with our experimental conditions.

5.3 Analysis of Results

For optimal analysis of the results, it is necessary to determine the standard deviation (sd) of the measurements for the technique used. In the examples below, we will consider the sd for the measurement of a segment of length L to be 1 kb+0.1.L. These values, in agreement with our experience with Molecular Combing, should be adapted to the specific experimental conditions used. As stated above, the number of repeat units may be determined by measuring the repeat array and, provided the location probes are present, this number of repeat units may be linked to a chromosome and a haplotype. However, the precision of a single measurement is insufficient to assess the number of repeat units with certainty.

For example, the error on one measurement may reach 8.6 kb (2.sd) on a 33 kb (10 repeat) -long repeat array. Thus, if only one measurement was made, results should be indicated as 7-13 repeat units [24.4; 41.6 kb]. In the optics of diagnostics, where the threshold between healthy individuals and carriers of the disease is believed to be 10 repeat units, this would lead to a diagnostic uncertainty. The precision of measurement may be dramatically improved by considering several measurements of the same allele. In the previous example, if 28 measurements are made and the average is 33 kb, the confidence interval is brought down to [31.4;34.6 kb] (2.sd/√28=1.6), and thus the number of repeat units may be reported to be 10 with relative certainty. Several approaches may be found to compute the average size with a sufficient number of measurements.

5.3.1 Stringent Approach

In the simplest approach, only signals assigned unambiguously to a chromosome and haplotype are considered. In a simple case, only one allele exists for one specific chromosome and haplotype. In an individual heterozygous for the 4q haplotype (4qA/4qB), for example, only one allele exists for 4qA. All the repeat arrays assigned to 4qA may then be measured and the measured average is taken as the size determination for the 4qA allele. The presence of probes on both sides (centromeric and telomeric) of the repeat array proves that the DNA molecules were not broken within the repeat array and the measurements may be hypothesized to follow a Gaussian distribution. The half-width of the confidence interval in this case may be estimated as 2.sd/√n, where n is the number of measurements for this allele. In the optics of diagnostics, the number of measurements is deemed sufficient when the confidence interval for the number of repeat units is completely within the "healthy" or within the "pathological" range. If additional benefits may be drawn from a more precise assessment (e.g. if the precise number of repeat units in the pathological range allow to predict the severity of the disease), additional measurements may be added until the confidence interval is narrow enough for the most precise interpretation possible.

In a more complex situation, two alleles may share the same chromosome and haplotype assignment. This is the case for a homozygous 4qA/4qA individual, or on chromosome 10 if both 10q chromosomes have the expected qA haplotype. In this case, a first step in the interpretation should be the analysis of the distribution of measurements, for example by visualizing the histogram of repeat array sizes. In the cases considered, if the two alleles have "sufficiently different" sizes, two distinct peaks (two modes) are expected to appear on the histogram. The two modes may then be considered as the sizes of the two alleles. Alternatively, the average of the values "within one peak"— as defined below—may be preferred as the best assumption for the size of each allele. To compute the half-width of the confidence interval as above, it is necessary to consider the number of measurements within each peak. One may consider, for example, all the measurements within the interval [mode−2.sd;mode+2.sd] as belonging to one allele, provided the intervals for the two alleles do not overlap.

In cases where the lengths of the two alleles are not sufficiently different for the two peaks to be clearly separated, one possible solution is to find the superposition of two Gaussian distributions that will best fit the observed distribution. The parameters for the two distributions to be fitted are the average size, the standard deviation, and the size of the sample within each allele (number of observations corresponding to each allele). The observed distribution will provide approximate values for the distributions to be fitted and the average sizes for the fitted distributions are discrete since they correspond to an integer number of repeat units. The standard deviation may be assumed from knowledge of the technique. The sample sizes are linked by n1+n2=n where n1 and n2 are the sample sizes from each allele and n is the total number of observations for this chromosome and haplotype. Besides, n1 and n2 may be assumed to be roughly equal. The combinations of parameters are thus in finite number, and this approach is relatively easy to implement. Although all these steps may be performed manually by the man skilled in the art, it is also possible to use appropriate, e.g. statistical analysis, software.

5.3.2 Relaxed Approaches: Intact, Non-Located Signals

The main drawback to the "stringent approach" is that it requires a potentially high number of measurements for every allele. With our implementation of Molecular Combing, the number of signals resulting from the analysis of a whole hybridized surface (22×22 mm) ranges from 100 to 400. Thus, 25 to 100 copies of each allele are expected, but only a fraction of these contain the intact FSHD locus with the repeat array and its surrounding probes. This may decrease the number of measurements assigned specifically to a locus and with an intact repeat array to as few as 5 signals or less for one allele. In this context, gathering the number of signals suitable for an unambiguous determination would require high amounts of time and high costs. In order to achieve such a result with less resource, it is possible to lower the stringency of the criteria for the inclusion of measurements in the analysis.

In a first step towards relaxing criteria, one may wish to include data for which the repeat array is surrounded by probes, and can thus safely be considered as intact, but where the exact chromosome and/or haplotype are not known with certainty. For example, if only the most proximal probe of the four-probe motif for the chromosomal location remains, due to DNA molecule breakage, unambiguous assignation to chromosome 4 or 10 may not be possible. All the intact measurements may be plotted on one histogram. It is expected to display four peaks in a normal individual, corresponding to the two alleles on each of the 4q and 10q chromosomes. The size of each allele and the number of individual measurements within each peak (and, thus, the confidence interval) may be assessed by methods similar to those described above.

Some of the measurements within each peak should be unambiguously assigned to a chromosome and haplotype. If the peaks are distinct, only one "species" of measurements will be found in one peak, and thus the size and confidence interval may be assigned to a chromosome and haplotype. This remains possible if no measurement in the peak may be assigned unambiguously to a given chromosome and haplotype, as long as exists within the peak at least one measurement unambiguously assigned to a given chromosome and one to a given haplotype. If two peaks with identical chromosome and haplotype assignation overlap, the interpretation method is similar to that described above for the stringent approach with overlapping peaks. If two peaks overlap and at least one characteristic (chromosome or haplotype) allows distinguishing two populations within the peaks, the preferred method is to plot separately the histograms for the two possible values of this characteristic. Thus, only one of the two peaks should remain in each histogram, and the same reasoning as above may be applied.

In this setup, only the intact signals are considered and it is thus important in itself to test whether a repeat array is intact, independently from the assignment to a chromosome and/or haplotype. Considering this, one may wish to design additional probes to the ones described above for this sole purpose. A probe covering the region common to 4q and 10q, for example, which would hybridize close to the repeat array on its centromeric side, would allow to tell the array was not broken at the centromeric end even if the molecule was broken further upstream, precluding detection of the chromosome-specific probes. This reasoning may also be adapted to the telomeric sequences, where sequences common to qA and qB haplotypes exist and may be used.

5.3.3 Relaxed Approach: Non-Intact, Non-Located Signals

One may wish to further relax criteria for the inclusion of measurements, leading to yet bigger sample sizes. For example, one may accept as valid a measurement of a repeat array with probes only on one side. In this case, the repeat array may be interrupted by a break in the DNA molecule and the measurement may not correspond to the whole length of the repeat array. The main drawback in this case is the existence of measurements representing only fractions of repeat arrays, which may be included when computing the average size, and thus lead to an underestimation of the repeat array size.

This approach may still give satisfactory results, however, if the fraction of broken repeat arrays in the considered data is not too high. In our one-color design for probes, for example, with qA being detected as two short probes, detection efficiency is not 100%. Thus, intact repeat arrays may appear with only the centromeric location probes. Additionally, the distance between the centromeric probes and the repeat array (~50 kb) makes a breakage of the DNA molecule in this gap a likely event. Thus, intact repeat arrays may appear with only the telomeric probes, or no location probe at all if the molecule is broken and the qA probes not detected. We therefore believe that the fraction of intact repeat arrays in the measurements that could not be proven as intact is high, and that is makes sense to factor these measurements in our computation of the average size with our setup.

Importantly, these approaches may be combined and/or may be adopted depending on the required precision of the measurements. For example, a relaxed approach may be adopted in a first run, leading to an estimation of the allele sizes, and allowing the detection of a potentially pathogenic 4qA allele. If the existence of such an allele may be excluded from this first fast analysis, and if this is the only reason for performing the test, it is not necessary to continue further. If a 4qA allele with a size that may be in the pathogenic range appears, further analysis (i.e. collection of a larger number of signals) may be performed to gather specific and precise data.

Since one parameter in the time and costs required for an analysis is the number of fluorochrome used (with a higher number of fluorochromes, longer acquisition times will be necessary, and the digitalization of a given surface will be slower), it is possible to vary the hybridization and/or acquisition parameters to meet the approach adopted. Indeed, in the relaxed approach only the size of the repeat array is used on every signal. The location probes are used solely to assign the peaks to one given chromosome and haplotype combination and this requires only a few signals for every allele. One could consider digitalizing only the surface necessary to collect these few signals with several colors, and collecting quickly a high number of measurements by digitalizing further using only the color required for the repeat array.

5.3.4 Mosaicism

Since it is suspected that many individuals bear somatic mosaicism for the FSHD locus, special attention must be given to the detection of such an event. The ability to detect a mosaic allele (i.e. an allele present in only a fraction of cells) depends on a number of factors, principally the fraction of cells bearing this allele in the analyzed sample and the size of the mosaic allele relative to the size of other alleles. It is therefore impossible to design the test in such a way that it will always detect the existence of a mosaic allele. However, it is possible to perform the test in such a way that the detection of such an allele is made highly probable (with an arbitrary probability), provided some assumptions are made. This requires to adapt the below reasoning in every specific case and with the requirements dictated by the application.

For example, in a diagnostic setup, a clinician might consider the existence of a 4qA mosaic allele bore by at least 10% of cells and with 10 repeat units or less as an event that should be detected by at least a 95% probability. If in a first run of the test, using the stringent approach described above, the only 4qA allele is estimated at 17 repeat units (56.1 kb, sd=6.6 kb), the minimum number of signals to analyze to insure 95% probability of detection of a mosaic allele may be calculated based on the "worst case" scenario. The most difficult case to detect would be a 10 repeat unit-allele (33 kb, sd=4.3 kb) in 10% of cells. A signal from the major allele has less than 2.5% probability to be measured below 42 kb (56.1−2×6.6=42.9). Therefore, if two measurements are found below this value, the analysis will conclude correctly that a smaller allele exists. If one of ten 4qA signals is from the mosaic allele and 80 4qA signals are measured, there is more than 96% probability that the mosaic allele will appear at least twice, and the signals have a 97.5% probability each to be measured below 42 kb (33+2×4.3=41.6), so there is overall more than 95% probability of detecting two signals below 42 kb and thus to correctly detect a mosaic allele. In this case, to meet the clinician's criteria, it is necessary to keep analyzing data until 80 4qA signals are detected.

It should be pointed that this would probably not be sufficient for a correct assessment of the size of the mosaic allele, so it may be necessary, when a mosaic allele is detected, to analyze a greater number of signals. Also, when a sufficient number of signals has been analyzed, the estimation of the fraction of cells carrying the mosaic allele is made possible by comparing the number of measurements in the "mosaic" peak relative to a homogenous (non-mosaic) peak. A confidence interval for this fraction may be computed using conventional statistics.

5.3.5 Non-Canonical Locus

The above described methods to analyze the data assume that the detected signals may be assigned to one of the expected motifs in the probe scheme that was chosen, or to part of a motif. If a signal appears to diverge from the expected ("canonical") motifs, extra care should be taken in the interpretation. It is first necessary to make sure the non-canonical motif is not an experimental artefact. Such artefacts include mainly the probability that two distinct DNA molecules covering part of the targeted loci are aligned by chance on a combed surface. If the motif (or a part thereof diverging from the canonical motifs) is found several times in one analysis, it may be safely concluded that it is not the result of an artefact.

In order to interpret the precise nature of the rearrangement responsible for the non-canonical motif, one may perform supplementary molecular combing experiments and/or use other molecular biology techniques (including PCR, sequencing, southern bloting, CGH or array-based CGH, etc). Most techniques require some hypothesis on the rearrangement, globally equating to a description of the rearrangement with a few kb resolution. Therefore, such a description may first be sought by supplementary molecular combing experiments.

For example, if a hybridization signal appears where no signal was expected, corresponding to the insertion of sequences found in one of the probes, it probably is best to first identify the nature of said signal (i.e. the probe responsible for the signal), if this is not immediately deducible from the label of the unexpected signal. This may be achieved by hybridizations where one or several probes are omitted. If one probe is omitted at a time, the number of different hybridizations to be performed is equal to the number of probes sharing the same label as the inserted sequence. If this number is too large, a combinatorial approach may be adopted, exemplified in FIG. 7, where several probes may be omitted in one experiment. $2^n$ possible probes may be distinguished out of n hybridization experiments by such an approach. It is also possible to use other labels instead of or in addition to omitting probes. If x different labels are used (in this number, the possibility of omitting a probe must be considered one label), $x^n$ possible probes may be distinguished out of n hybridization experiments. Hybridizing parts of the signal-generating probe may allow to further precise the portion of the probe that was inserted if this is necessary As an other example, in the case of a shorter than expected distance between two probes, corresponding to the deletion of sequences between the two probes, additional hybridizations may be performed with probes selected within the region separating the two probes, in order to identify which portion of this region was deleted.

Once the breakpoint of the observed event is located with a few kb resolution, one possible approach is to design primers on both sides of the breakpoint, in order to amplify a fragment containing the breakpoint by PCR or long-range PCR, followed by restriction analysis and/or sequencing and/or other analysis techniques to further detail the rearrangement.

Conclusions on the effect of the rearrangement observed may be drawn by the man skilled in the art by comparing this and other rearrangements published in the scientific literature. If no corresponding case is published, the current physiopathological description of the FSHD disease may be used as a guide to predict phenotypic outcome, but this should obviously not be used as a definitive diagnostic conclusion.

6. Applications

Applications of the herein described method for assessing the D4Z4 repeat number on 4q and 10q chromosomes, the qA/qB haplotypes of said chromosomes and potentially structural variants of these loci are mainly intended as research-oriented or as diagnostics-oriented.

6.1 Clinical Research

Uses as a research tool include applications such as researching physiopathological mechanisms involved in FSHD. In this view, it is particularly indicated to describe in more exact detail cases that are considered complex with other techniques, such as translocations between 4q and 10q chromosomes, somatic mosaicism etc. By linking clinical observations to this more detailed description of the molecular features of these cases, one may find e.g. common attributes of genotypes associated with low- or high-penetrance, mild or severe phenotype etc. The research for drug targets, or gene therapy techniques, or other therapeutic approaches may benefit from this enhanced physiopathological description of the disease.

Also, much like what is described below for diagnostics setups, it may be useful to use the more precise information of the genetic features of individuals provided by the herein described test in therapeutic clinical studies. It may be, indeed, that some parameters accessible through this test dictate not only the presence and/or severity of the disease, but also the response to a specific therapy, or the design of individual therapies (e.g. gene therapies). Identification of such parameters would probably require the test to be performed within a clinical study using techniques conventional for pharmacogenomics studies.

Since it has been suggested that epigenetic features such as CpG methylation may play a role in the physiopathology of FSHD, it is also conceivable to study the methylation in this locus in Molecular Combing experiments. The detection of probes may for example be coupled with the detection of methylcytosine (metC)-rich regions using anti-metC antibodies and the conventional technique to detect probes, or an adaptation of the latter. It may be necessary to reduce the number of colors to allow detection of metC. This may be done for example by removing the repeat probe from the hybridization, while in parallel the length of the repeat arrays may be assessed independently from the detection of metC.

Since regions containing repeats are known to have potential effect on DNA replication and since this may be linked to the physiopathology of FSHD and/or to the transmission of the disease and/or its de novo appearance in individuals, it may also be interesting to investigate DNA replication in the regions containing D4Z4 repeat arrays. This may be done essentially by following the procedures described in Lebofsky and Bensimon, 2006, In these procedures, either one or two fluorochromes are available for the detection of probes, and thus the one-color scheme for location probes, along with the repeat probe, may be detected simultaneously with nucleotides incorporated during DNA replication. Alternatively, in a sample where the physical organization of the regions containing the repeat arrays has already been determined by previous experiments, the repeat probe may be omitted and thus two colors may be available for the detection of location probes. The kinetic parameters of DNA replication within these loci may help to understand the physiopathology of FSHD. They may also be used as additional parameters in diagnostics or pharmacological studies.

6.2 Diagnostics

As a diagnostics tool, the most straightforward application is to assess the number of repeat units using the most simple probe designs described, and to conclude using the scientific consensus linking the number of repeat units on 4qA alleles to the presence of the disease. If this is the chosen approach, some care should be taken when setting the threshold, i.e. the repeat array length (or the repeat unit number) that distinguished healthy from FSHD individuals. There is indeed some divergence in the literature as to which threshold to use. For a part, this may be due to the variations in the implementation to measure the repeat array sizes using conventional methods. To reduce this effect, it is probably best to calibrate the threshold using a set of patient sample that were previously assessed for the repeat number using conventional methods. This set of samples may be tested using the protocol described herein, and the conversion factor from physical length to number of repeat units deduced from the comparison with the initial assessment (e.g. by a linear regression, when plotting the measured length as a function of the previously estimated number of repeat units). The threshold may then be set to the same value of number of repeat units that was used in the initial diagnostics for these samples.

Alternatively, if another technique is available that lacks some of the advantages of the technique described herein but has its own advantages, a combination of the two techniques may be used. For example, if a cheap and convenient technique is available that has good sensitivity (i.e. it very rarely diagnoses FSHD carriers as healthy) but lacks specificity (i.e. it too often diagnoses healthy individuals as carriers of FSHD), it may be used as a first sorting of patients, and the technique described herein as a control when a patient is diagnosed as sick by this first technique.

By performing the test in the way described above, the performances of the test will be limited by the knowledge available through other techniques. To overcome this limitation, it may be necessary to perform clinical studies in order to reach a potentially more exact description of the genetic parameters involved in the phenotype of FSHD (healthy or carrier, severity, penetrance, etc.). Parameters that may be assessed and compared to clinical outcome to find the relevant ones—using conventional techniques for statistical correlation—include: the number of repeat units on 4qA alleles, the presence of other short alleles along with a short 4qA allele, the presence of long alleles along with a short 4qA allele, the presence of unexpected motifs (chromosome 10q with a qB haplotype, non-canonical gap between chromosome-specific probes and the repeat probe, alternative non-qA non-qB haplotypes, etc), the presence of a mosaic and the fraction of cells bearing it, the presence of inversions within the repeat array, insertion of unrelated sequences within the repeat array, etc.

The result of a diagnostic test using this technique may be used for several reasons. For one thing, in a muscular dystrophy-bearing patient, molecular diagnostics of FSHD may rule out a possible confusion with a similar dystrophy, and/or assist in the choice of a relevant therapy. As stated above, it may also be possible to predict therapy response or to design specifically a tailored therapy in application of the results of the test. In a prenatal diagnostic setup, it may allow to detect early during development the presence of the disease and to correctly predict the expected clinical outcome, in order for the parents to make an informed decision. If technical evolutions make possible the use of a DNA-stretching technique on a very limited number of cells (1-2 cells), this test may also be used for preimplantation diagnostics. In a genetic counseling application, the correct assessment of the genetic features for parents should allow to correctly predict the probability of transmitting the disease, especially if the fraction of a mosaic allele may be determined, as well as the penetrance of a given allele.

REFERENCES

Berlemont, S. and Bensimon, A. and Olivo-Marin, J.-C (2007). "Feature-Adapted Fast Slant Stack", IEEE International Conference on Image Processing; vol. 4:57-60. September 2007

Berlemont, S. and Bensimon, A. and Olivo-Marin, J.-C (2007a). "Detection of Curvilinear Objects in Noisy Image using Feature-Adapted Beamlet Transform", IEEE International Conference on Acoustic, Speech and Signal Processing. April 2007

Berlemont, S. and Bensimon, A. and Olivo-Marin, J.-C (2007b). "Detection of Linear Structures in Biological Images", Asilomar Conference on Signals, Systems, and Computers. November 2007

Berlemont, S. and Bensimon, A. and Olivo-Marin, J.-C. (2007c). "Detection of Curvilinear objects in Biological Noisy Image using Feature-Adapted Fast Slant Stack", SPIE conference Wavelets XII, Special Session on Wavelet in Bioimaging. August 2007

Cacurri S, Piazzo N, Deidda G, Vigneti E, Galluzzi G, Colantoni L, Merico B, Ricci E, Felicetti L (1998). "Sequence homology between 4qter and 10qter loci facilitates the instability of subtelomeric KpnI repeat units implicated in facioscapulohumeral muscular dystrophy." Am J Hum Genet.; 63(1):181-90.

Conti C, Caburet S, Schurra C, Bensimon A (2001). "Molecular combing", Curr Protoc Cytom.; Chapter 8:Unit 8.10.

Deak K L, Lemmers R J, Stajich J M, Klooster R, Tawil R, Frants R R, Speer M C, van der Maarel S M, Gilbert J R (2007). "Genotype-phenotype study in an FSHD family with a proximal deletion encompassing p13E-11 and D4Z4." Neurology; 68(8):578-82.

Dimalanta E T, Lim A, Runnheim R, Lamers C, Churas C, Forrest D K, de Pablo J J, Graham M D, Coppersmith S N, Goldstein S, Schwartz D C (2004). "A microfluidic system for large DNA molecule arrays." Anal Chem. 2004 Sep. 15; 76(18):5293-301.

Ehrlich M, Jackson K, Tsumagari K, Camaño P, Lemmers R J (2007). "Hybridization analysis of D4Z4 repeat arrays linked to FSHD." Chromosoma.; 116(2):107-16.

Florijn R J, Bonden L A, Vrolijk H, Wiegant J, Vaandrager J W, Baas F, den Dunnen J T, Tanke H J, van Ommen G J, Raap A K (1995). "High-resolution DNA Fiber-FISH for genomic DNA mapping and colour bar-coding of large genes." Hum Mol Genet. 1995 May; 4(5):831-6.

Fransz P F, Alonso-Blanco C, Liharska T B, Peeters A J, Zabel P, de Jong J H (1996). "High-resolution physical mapping in *Arabidopsis thaliana* and tomato by fluorescence in situ hybridization to extended DNA fibres." Plant J. 1996 March; 9(3):421-30.

Gad S, Aurias A, Puget N, Mairal A, Schurra C, Montagna M, Pages S, Caux V, Mazoyer S, Bensimon A, Stoppa-Lyonnet D (2001). "Color bar coding the BRCA1 gene on combed DNA: a useful strategy for detecting large gene rearrangements." Genes Chromosomes Cancer.; 31(1): 75-84.

Goto K, Nishino I, Hayashi Y K (2006). "Rapid and accurate diagnosis of facioscapulohumeral muscular dystrophy." Neuromuscul Disord.; 16(4):256-61.

Haaf T, Ward D C (1994). "Structural analysis of alpha-satellite DNA and centromere proteins using extended chromatin and chromosomes." Hum Mol Genet. 1994 May; 3(5):697-709.

Heiskanen M, Kallioniemi O, Palotie A (1996). "Fiber-FISH: experiences and a refined protocol." Genet Anal. 1996 March; 12(5-6):179-84.

Heiskanen M, Karhu R, Helisten E, Peltonen L, Kallioniemi O P, Palotie A (1994). "High resolution mapping using fluorescence in situ hybridization to extended DNA fibers prepared from agarose-embedded cells." Biotechniques. 1994 November; 17(5):928-9, 932-3.

Heng H H, Squire J, Tsui L C (1992). "High-resolution mapping of mammalian genes by in situ hybridization to free chromatin." Proc Natl Acad Sci USA. 1992 Oct. 15; 89(20):9509-13.

Herrick J, Michalet X, Conti C, Schurra C, Bensimon A (2000). "Quantifying single gene copy number by measuring fluorescent probe lengths on combed genomic DNA." Proc Natl Acad Sci USA.; 97(1):222-7. Erratum in: Proc Natl Acad Sci USA.; 97(8):4410.

Hewitt J E, Lyle R, Clark L N, Valleley E M, Wright T J, Wijmenga C, van Deutekom J C, Francis F, Sharpe P T, Hofker M, et al (1994). "Analysis of the tandem repeat locus D4Z4 associated with facioscapulohumeral muscular dystrophy." Hum Mol Genet.; 3(8):1287-95.

Jing J, Reed J, Huang J, Hu X, Clarke V, Edington J, Housman D, Anantharaman T S, Huff E J, Mishra B, Porter B, Shenker A, Wolfson E, Hiort C, Kantor R, Aston C, Schwartz D C (1998). "Automated high resolution optical mapping using arrayed, fluid-fixed DNA molecules." Proc Natl Acad Sci USA. 1998 Jul. 7; 95(14): 8046-51.

Kekou K, Fryssira H, Sophocleous C, Mavrou A, Manta P, Metaxotou C (2005). "Facioscapulohumeral muscular dystrophy molecular testing using a non radioactive protocol." Mol Cell Probes.; 19(6):422-4.

Larson J W, Yantz G R, Zhong Q, Charnas R, D'Antoni C M, Gallo M V, Gillis K A, Neely L A, Phillips K M, Wong G G, Gullans S R, Gilmanshin R (2006). "Single DNA molecule stretching in sudden mixed shear and elongational microflows." Lab Chip. 2006 September; 6(9): 1187-99. Epub 2006 Jul. 7.

Lebofsky R, Bensimon A (2005). "DNA replication origin plasticity and perturbed fork progression in human inverted repeats." Mol Cell Biol.; 25(15):6789-97.

Lebofsky R, Bensimon A, (2006). "Fluorescent Visualization of Genomic Structure and DNA replication at the Single Molecule Level." in "Cell Biology, a Laboratory Handbook", 3$^{rd}$ Ed., Vol. 3, chapter 45; Elsevier Academic Press, 2006

Lebofsky R, Heilig R, Sonnleitner M, Weissenbach J, Bensimon A (2006). "DNA replication origin interference increases the spacing between initiation events in human cells." Mol Biol Cell.; 17(12):5337-45.

Lemmers R J, Wohlgemuth M, van der Gaag K J, van der Vliet P J, van Teijlingen C M, de Knijff P, Padberg G W, Frants R R, van der Maarel S M (2007). "Specific sequence variations within the 4q35 region are associated with facioscapulohumeral muscular dystrophy." Am J Hum Genet.; 81(5):884-94.

Lemmers R J, van der Wielen M J, Bakker E, Frants R R, van der Maarel S M (2006). "Rapid and accurate diagnosis of facioscapulohumeral muscular dystrophy." Neuromuscul Disord.; 16(9-10):615-7.

Lemmers R J, Osborn M, Haaf T, Rogers M, Frants R R, Padberg G W, Cooper D N, van der Maarel S M, Upadhyaya M (2003). "D4F104S1 deletion in facioscapulohumeral muscular dystrophy: phenotype, size, and detection." Neurology.; 61(2):178-83.

Lemmers R J, de Kievit P, Sandkuijl L, Padberg G W, van Ommen G J, Frants R R, van der Maarel S M (2002). "Facioscapulohumeral muscular dystrophy is uniquely associated with one of the two variants of the 4q subtelomere." Nat Genet.; 32(2):235-6.

Lemmers R J, van der Maarel S M, van Deutekom J C, van der Wielen M J, Deidda G, Dauwerse H G, Hewitt J, Hofker M, Bakker E, Padberg G W, Frants R R (1998). "Inter- and intrachromosomal sub-telomeric rearrangements on 4q35: implications for facioscapulohumeral muscular dystrophy (FSHD) aetiology and diagnosis." Hum Mol Genet.; 7(8):1207-14.

Mann S M, Burkin D J, Grin D K, Ferguson-Smith M A (1997). "A fast, novel approach for DNA fibre-fluorescence in situ hybridization analysis." Chromosome Res. 1997 April; 5(2):145-7.

Michalet X, Ekong R, Fougerousse F, Rousseaux S, Schurra C, Hornigold N, van Slegtenhorst M, Wolfe J, Povey S, Beckmann J S, Bensimon A (1997). "Dynamic molecular combing: stretching the whole human genome for high-resolution studies." Science.; 277(5331):1518-23.

Palotie A, Heiskanen M, Laan M, Horelli-Kuitunen N (1996). "High-resolution fluorescence in situ hybridization: a new approach in genome mapping." Ann Med. 1996 April; 28(2):101-6.

Parra I, Windle B (1993). "High resolution visual mapping of stretched DNA by fluorescent hybridization." Nat Genet. 1993 September; 5(1):17-21.

Raap A K (1998). "Advances in fluorescence in situ hybridization." Mutat Res. 1998 May 25; 400(1-2):287-98.

Samad A, Huff E F, Cai W, Schwartz D C (1995). "Optical mapping: a novel, single-molecule approach to genomic analysis." Genome Res. 1995 August; 5(1):1-4.

Schwartz D C, Li X, Hernandez L I, Ramnarain S P, Huff E J, Wang Y K (1996). "Ordered restriction maps of Saccharomyces cerevisiae chromosomes constructed by optical mapping." Science. 1993 Oct. 1; 262(5130):110-4.

Tupler R, Barbierato L, Memmi M, Sewry C A, De Grandis D, Maraschio P, Tiepolo L, Ferlini A (1998). "Identical de novo mutation at the D4F104S1 locus in monozygotic male twins affected by facioscapulohumeral muscular dystrophy (FSHD) with different clinical expression." J Med Genet.; 35(9):778-83.

Van der Maarel S M, Frants R R, Padberg G W (2007). "Facioscapulohumeral muscular dystrophy." Biochim Biophys Acta.; 1772(2):186-94.

Van der Maarel S M, Deidda G, Lemmers R J, van Overveld P G, van der Wielen M, Hewitt J E, Sandkuijl L, Bakker B, van Ommen G J, Padberg G W, Frants R R (2000). "De novo facioscapulohumeral muscular dystrophy: frequent somatic mosaicism, sex-dependent phenotype, and the role of mitotic transchromosomal repeat interaction between chromosomes 4 and 10." Am J Hum Genet.; 66(1):26-35.

Van Deutekom J C, Wijmenga C, van Tienhoven E A, Gruter A M, Hewitt J E, Padberg G W, van Ommen G J, Hofker M H, Frants R R (1993). "FSHD associated DNA rearrangements are due to deletions of integral copies of a 3.2 kb tandemly repeated unit." Hum Mol Genet.; 2(12): 2037-42.

Van Geel M, Dickson M C, Beck A F, Bolland D J, Frants R R, van der Maarel S M, de Jong P J, Hewitt J E (2002). "Genomic analysis of human chromosome 10q and 4q telomeres suggests a common origin." Genomics.; 79(2): 210-7.

Vaandrager J W, Schuuring E, Kluin-Nelemans H C, Dyer M J, Raap A K, Kluin P M (1996). "DNA fiber fluorescence in situ hybridization analysis of immunoglobulin class switching in B-cell neoplasia: aberrant CH gene rearrangements in follicle center-cell lymphoma." Blood. 1998 Oct. 15; 92(8):2871-8.

Wiegant J, Kalle W, Mullenders L, Brookes S, Hoovers J M, Dauwerse J G, van Ommen G J, Raap A K (1996). "High-resolution in situ hybridization using DNA halo preparations." Hum Mol Genet. 1992 November; 1(8): 587-91.

Windle B, Silvas E, Parra I (1996). "High resolution microscopic mapping of DNA using multi-color fluorescent hybridization." Electrophoresis. 1995 Feburary; 16(2): 273-8.

The invention claimed is:

1. A method for analysing in vitro D4Z4 tandem repeat arrays contained on nucleic acid representative of chromosomes, said method comprising a hybridization step of contacting nucleic acid representative of said chromosomes with a mix of at least the following probes:
- a probe or a set of probes called "repeat probe(s)", which is (are) specific for D4Z4 tandem repeat arrays;
- a probe or a set of probes which enable(s) to distinguish chromosome 4 (4q) from chromosome 10 (10q); and
- a probe or a set of probes which enable(s) to distinguish haplotype qA from haplotype qB, and
- optionally, a probe or a set of probes which enable(s) to distinguish chromosome Y from chromosome 4 and/or from chromosome 10,
- wherein said probes are optionally labelled, wherein either all the labelled probes being labelled with the same label(s) or at least one probe is labelled with one or more label(s) different from the label(s) of other probes.

2. The method according to claim 1, comprising the following steps:
a) providing a support on which a nucleic acid sample comprising nucleic acid representative of chromosomes has been previously stretched in linear and parallel strands and hybridizing said nucleic acid with the probes;
b) detecting the hybridization signals corresponding to the probes; and
c) analysing organization of D4Z4 tandem repeat arrays on nucleic acid representative of chromosomes and/or analysing methylation and/or analysing biochemical events in said D4Z4 tandem repeat arrays and/or in regions adjacent or essentially adjacent to said D4Z4 tandem repeat arrays.

3. The method according to claim 2, wherein the step of hybridization with the probes is performed before and/or after stretching the nucleic acid sample on the support, said step of hybridization being, if necessary, preceded by a step of denaturation of said nucleic acid sample and/or of the probes.

4. The method according to claim 2, wherein step b) further includes obtaining, for each nucleic acid which shows at least one hybridization signal corresponding to a repeat probe, information corresponding to one or a combination of the following categories: (1) typing of the hybridization signals, (2) the length of one or several hybridization signals, (3) the position of one or several hybridization signals relative to a D4Z4 tandem repeat array, and (4) the distance between two hybridization signals, in particular between two consecutive hybridization signals.

5. The method according to claim 4, wherein step b) further includes (i) measuring the length of every hybridization signal corresponding to a repeat probe and/or measuring, for every detected D4Z4 tandem repeat array, the distance between the first hybridization signal corresponding to a repeat probe and the last hybridization signal corresponding to a repeat probe on the same nucleic acid strand and optionally (ii) establishing a histogram of the measured lengths or distances.

6. The method according to claim 4, wherein the nucleic acid sample has been stretched on the support using a molecular combing technique.

7. The method according to claim 4, wherein the probe or set of probes which enables to distinguish chromosome 4 from chromosome 10 comprises:
(i) a probe which is specific for chromosome 4 or (ii) a probe or a set of probes hybridizing with chromosome 4, said probe or set of probes being chosen in such a way that upon hybridization to chromosome 4, the position of the probes, one compared to the others, forms a signature which is specific for chromosome 4;
(i) a probe which is specific for chromosome 10 or (ii) a probe or a set of probes hybridizing with chromosome 10, said probe or set of probes being chosen in such a way that upon hybridization to chromosome 10, the position of the probes, one compared to the others, forms a signature which is specific for chromosome 10;
wherein the probe or set of probes which enables to distinguish the qA haplotype from the qB haplotype comprises:
(i) a probe which is specific for the qA haplotype or (ii) a probe or a set of probes hybridizing with chromosomes of the qA haplotype, said probe or set of probes being chosen in such a way that upon hybridization to said chromosomes, the position of the probes, one compared to the others, forms a signature which is specific for the qA haplotype; and/or
(i) a probe which is specific for the qB haplotype or (ii) a probe or a set of probes hybridizing with chromosomes of the qB haplotype, said probe or set of probes being chosen in such a way that upon hybridization to said chromosomes, the position of the probes, one compared to the others, forms a signature which is specific for the qB haplotype;
wherein the probe or set of probes which enables to distinguish chromosome Y from chromosome 4 and/or from chromosome 10 comprises (i) a probe which is specific for chromosome Y or (ii) a probe or a set of probes hybridizing with chromosome Y, said probe or set of probes being chosen in such a way that upon hybridization to chromosome Y, the position of the probes, one compared to the others, forms a signature which is specific for chromosome Y.

8. The method according to claim 2, wherein step b) further includes (i) measuring the length of every hybridization signal corresponding to a repeat probe and/or measuring, for every detected D4Z4 tandem repeat array, the distance between the first hybridization signal corresponding to a repeat probe and the last hybridization signal corresponding to a repeat probe on the same nucleic acid strand and preferably (ii) establishing a histogram of the measured lengths or distances.

9. The method according to claim 8, wherein the nucleic acid sample has been stretched on the support using a molecular combing technique.

10. The method according to claim 8, wherein the probe or set of probes which enables to distinguish chromosome 4 from chromosome 10 comprises:
(i) a probe which is specific for chromosome 4 or (ii) a probe or a set of probes hybridizing with chromosome 4, said probe or set of probes being chosen in such a way that upon hybridization to chromosome 4, the position of the probes, one compared to the others, forms a signature which is specific for chromosome 4;
(i) a probe which is specific for chromosome 10 or (ii) a probe or a set of probes hybridizing with chromosome 10, said probe or set of probes being chosen in such a way that upon hybridization to chromosome 10, the position of the probes, one compared to the others, forms a signature which is specific for chromosome 10;
wherein the probe or set of probes which enables to distinguish the qA haplotype from the qB haplotype comprises:
(i) a probe which is specific for the qA haplotype or (ii) a probe or a set of probes hybridizing with chromosomes of the qA haplotype, said probe or set of probes being chosen in such a way that upon hybridization to said chromosomes, the position of the probes, one compared to the others, forms a signature which is specific for the qA haplotype; and/or
(i) a probe which is specific for the qB haplotype or (ii) a probe or a set of probes hybridizing with chromosomes of the qB haplotype, said probe or set of probes being chosen in such a way that upon hybridization to said chromosomes, the position of the probes, one compared to the others, forms a signature which is specific for the qB haplotype;
wherein if any, the probe or set of probes which enables to distinguish chromosome Y from chromosome 4 and/or from chromosome 10 comprises (i) a probe which is specific for chromosome Y or (ii) a probe or a set of probes hybridizing with chromosome Y, said probe or set of probes being chosen in such a way that upon hybridization to chromosome Y, the position of the probes, one compared to the others, forms a signature which is specific for chromosome Y.

11. A method for analyzing D4Z4 tandem repeat arrays of nucleic acid or for determining the number of D4Z4 repeat units in said D4Z4 tandem repeat arrays, said method comprising performing the method according to claim 8, in which step c) further includes determining, for every detected D4Z4 tandem repeat array, whether said repeat array is located on a chromosome of the qA haplotype and/or on a chromosome 4, and
optionally whether said repeat array is located on a chromosome of the qB haplotype; and
optionally, whether said repeat array is located on a chromosome 10; and
optionally, whether said repeat array is located on a chromosome Y.

12. The method according to claim 2, wherein the nucleic acid sample has been stretched on the support using a molecular combing technique.

13. The method according to claim 2, wherein the probe or set of probes which enables to distinguish chromosome 4 from chromosome 10 comprises:
(i) a probe which is specific for chromosome 4 or (ii) a probe or a set of probes hybridizing with chromosome 4, said probe or set of probes being chosen in such a way that upon hybridization to chromosome 4, the position of the probes, one compared to the others, forms a signature which is specific for chromosome 4;
(i) a probe which is specific for chromosome 10 or (ii) a probe or a set of probes hybridizing with chromosome 10, said probe or set of probes being chosen in such a way that upon hybridization to chromosome 10, the position of the probes, one compared to the others, forms a signature which is specific for chromosome 10;
wherein the probe or set of probes which enables to distinguish the qA haplotype from the qB haplotype comprises:
(i) a probe which is specific for the qA haplotype or (ii) a probe or a set of probes hybridizing with chromosomes of the qA haplotype, said probe or set of probes being chosen in such a way that upon hybridization to said chromosomes, the position of the probes, one compared to the others, forms a signature which is specific for the qA haplotype; and/or
(i) a probe which is specific for the qB haplotype or (ii) a probe or a set of probes hybridizing with chromosomes of the qB haplotype, said probe or set of probes being chosen in such a way that upon hybridization to said chromosomes, the position of the probes, one compared to the others, forms a signature which is specific for the qB haplotype;
wherein the probe or set of probes which enables to distinguish chromosome Y from chromosome 4 and/or from chromosome 10 comprises (i) a probe which is specific for chromosome Y or (ii) a probe or a set of probes hybridizing with chromosome Y, said probe or set of probes being chosen in such a way that upon hybridization to chromosome Y, the position of the probes, one compared to the others, forms a signature which is specific for chromosome Y.

14. The method according to claim 13, wherein
1) the probe which is specific for either chromosome 4 or chromosome 10, the probe forming a signature specific for either chromosome 4 or chromosome 10 or at least one probe of the set of probes forming a signature specific for either chromosome 4 or chromosome 10 hybridizes with a region of the long arm of either chromosome 4 or chromosome 10 respectively, which region is centromeric relatively to the D4Z4 tandem repeat array, comprising (i) the region of the long arm of chromosome 4 which is located 4-100 kb upstream of the centromeric end of the D4Z4 tandem repeat array or (ii) the region of the long arm of chromosome 10 which is located 42-75 kb upstream of the centromeric end of the D4Z4 tandem repeat array and/or
2) the probe which is specific for the qA or qB haplotype, the probe forming a signature specific for the qA or qB haplotype or at least one probe of the set of probes forming a signature specific for the qA or qB haplotype hybridizes with a region of the long arm of chromosome 4qA or 4qB respectively which is telomeric, or immediately telomeric, relatively to the D4Z4 tandem repeat array.

15. The method according to claim 13, wherein the repeat probe or at least one of the repeat probes hybridizes with the whole sequence of the D4Z4 repeat unit of a D4Z4 tandem repeat array or with a portion of the D4Z4 repeat unit of a D4Z4 tandem repeat array, wherein said portion is a portion consisting of about a half of said D4Z4 repeat unit or a portion located at one end of said D4Z4 repeat unit or close to one end of said D4Z4 repeat unit.

16. The method according to claim 13, wherein
the probe which is specific for chromosome 4, the probe forming a signature specific for chromosome 4 or the set of probes forming a signature specific for chromosome 4 comprises at least one probe comprising:
vi) a sequence chosen among sequences ranging from the following coordinates relative to the NCBI build 36.1 Human reference sequence: 191089412 to 19096843 (4q1 probe), 191106888 to 19116775 (4q2 probe), 191128570 to 19138567 (4q3 probe) and 191148576 to 19158554 (4q4 probe);
vii) a sequence complementary to sequence i);
viii) a sequence capable of hybridizing to sequence (i) or (ii) under stringent conditions;
ix) a nucleotide variant of sequence i); or
x) a portion of any of sequences (i), (ii), (iii) or (iv), and/or
the probe which is specific for chromosome 10, the probe forming a signature specific for chromosome 10 or the set of probes forming a signature specific for chromosome 10 comprises at least one probe comprising:
vi) a sequence chosen among sequences ranging from the following coordinates relative to the NCBI build 36.1 Human reference sequence: 135247926 to 135252909 (10q1 probe), 135257958 to 135262966 (10q2 probe), 135267992 to 135272976 (10q3 probe), and 135278058 to 135282988 (10q4 probe);
vii) a sequence complementary to sequence i);
viii) a sequence capable of hybridizing to sequence (i) or (ii) under stringent conditions;
ix) a nucleotide variant of sequence i); or
x) a portion of any of sequences (i), (ii), (iii) or (iv), and/or
the probe which is specific for the qA haplotype, the probe forming a signature specific for the qA haplotype or the set of probes forming a signature specific for the qA haplotype comprises or consists of at least one probe comprising:
vi) a sequence chosen among sequences ranging from the following coordinates relative to the Genbank accession number U74496.1: 2756 to 3556 (qA1 probe) and 8723 to 10672 (qA2 probe);
vii) a sequence complementary to sequence i);
viii) a sequence capable of hybridizing to sequence (i) or (ii) under stringent conditions;
ix) a nucleotide variant of sequence i); or
x) a portion of any of sequences (i), (ii), (iii) or (iv), and/or
the probe which is specific for the qB haplotype, the probe forming a signature specific for the qB haplotype or at least one probe of the set of probes forming a signature specific for the qB haplotype comprises:
vi) a sequence ranging from the following coordinates relative to the NCBI build 36.1 Human reference sequence: 191252023 to 19253372 (qB1-3 probe) and 191248879 to 19252040 (qB1-4 probe), or the unique probe formed of qB1-3 and qB1-4 resulting in qB1;
vii) a sequence complementary to sequence i);
viii) a sequence capable of hybridizing to sequence (i) or (ii) under stringent conditions;
ix) a nucleotide variant of sequence i); or
x) a portion of any of sequences (i), (ii), (iii) or (iv), and/or the repeat probe or at least one of the repeat probes consists of:
vi) a sequence chosen among sequences ranging from the following coordinates relative to the Genbank accession number U85056.1: 24213 to 27507 (DeeZee probe), 24213 to 25948 (Dee probe) and 25763 to 27507 (Zee probe);
vii) a sequence complementary to sequence i);
viii) a sequence capable of hybridizing to sequence (i) or (ii) under stringent conditions;
ix) a nucleotide variant of sequence i); or
x) a portion of any of sequences (i), (ii), (iii) or (iv).

17. The method according to claim 2, wherein the nucleic acid sample used for stretching is DNA.

18. The method according to claim 2, wherein the mix of probes further includes at least one of the following probes, which are optionally labelled,
a probe or a set of probes hybridizing with the region of about 42 kb which is immediately centromeric relatively to the D4Z4 tandem repeat array on the long arm of chromosome 4 or with a portion of this region and/or hybridizing with the region of about 42 kb which is immediately centromeric relatively to the D4Z4 tandem repeat array on the long arm of chromosome 10 or with a portion of this region; and/or
a probe or a set of probes hybridizing with the region of about 15 kb which is immediately telomeric relatively to the D4Z4 tandem repeat array on chromosomes of the qA haplotype and/or on chromosomes of the qB haplotype or with a portion of this region.

19. A method for analyzing D4Z4 tandem repeat arrays of nucleic acid or for determining the number of D4Z4 repeat units in said D4Z4 tandem repeat arrays, said method comprising performing the method according to claim 2, in which step c) further includes determining, for every detected D4Z4 tandem repeat array, whether said repeat array is located on a chromosome of the qA haplotype and/or on a chromosome 4, and
optionally whether said repeat array is located on a chromosome of the qB haplotype; and
optionally, whether said repeat array is located on a chromosome 10; and
optionally, whether said repeat array is located on a chromosome Y.

20. The method according to claim 1, wherein the probe or set of probes which enables to distinguish chromosome 4 from chromosome 10 comprises:
(i) a probe which is specific for chromosome 4 or (ii) a probe or a set of probes hybridizing with chromosome 4, said probe or set of probes being chosen in such a way that upon hybridization to chromosome 4, the position of the probes, one compared to the others, forms a signature which is specific for chromosome 4;
(i) a probe which is specific for chromosome 10 or (ii) a probe or a set of probes hybridizing with chromosome 10, said probe or set of probes being chosen in such a way that upon hybridization to chromosome 10, the position of the probes, one compared to the others, forms a signature which is specific for chromosome 10;
wherein the probe or set of probes which enables to distinguish the qA haplotype from the qB haplotype comprises:
(i) a probe which is specific for the qA haplotype or (ii) a probe or a set of probes hybridizing with chromosomes of the qA haplotype, said probe or set of probes being chosen in such a way that upon hybridization to said chromosomes, the position of the probes, one compared to the others, forms a signature which is specific for the qA haplotype; and/or (i) a probe which is specific for the qB haplotype or (ii) a probe or a set of probes hybridizing with chromosomes of the qB haplotype, said probe or set of probes being chosen in such a way that upon hybridization to said chromosomes, the position of the probes, one compared to the others, forms a signature which is specific for the qB haplotype;

wherein the probe or set of probes which enables to distinguish chromosome Y from chromosome 4 and/or from chromosome 10 comprises (i) a probe which is specific for chromosome Y or (ii) a probe or a set of probes hybridizing with chromosome Y, said probe or set of probes being chosen in such a way that upon hybridization to chromosome Y, the position of the probes, one compared to the others, forms a signature which is specific for chromosome Y.

21. The method according to claim 20, wherein 1) the probe which is specific for either chromosome 4 or chromosome 10, the probe forming a signature specific for either chromosome 4 or chromosome 10 or at least one probe of the set of probes forming a signature specific for either chromosome 4 or chromosome 10 hybridizes with a region of the long arm of either chromosome 4 or chromosome 10 respectively, which region is centromeric relatively to the D4Z4 tandem repeat array, comprising (i) the region of the long arm of chromosome 4 which is located at 4-100 kb upstream of the centromeric end of the D4Z4 tandem repeat array or (ii) the region of the long arm of chromosome 10 which is located at 42-75 kb upstream of the centromeric end of the D4Z4 tandem repeat array and/or 2) the probe which is specific for the qA or qB haplotype, the probe forming a signature specific for the qA or qB haplotype or at least one probe of the set of probes forming a signature specific for the qA or qB haplotype hybridizes with a region of the long arm of chromosome 4qA or 4qB respectively which is telomeric, or immediately telomeric, relatively to the D4Z4 tandem repeat array.

22. The method according to claim 20, wherein (i) the probe which is specific for the qA haplotype, the probe forming a signature specific for the qA haplotype or at least one probe of the set of probes forming a signature specific for the qA haplotype hybridizes with the repeat array of a 68 bp-beta-satellite sequence which is immediately telomeric relatively to the D4Z4 tandem repeat array on the long arm of chromosome 4qA or with a portion of this beta-satellite sequence; or the repeat array of about 1 kb of (TTAGGG)$_n$ repeat units which is immediately telomeric relatively to said repeat array of a beta-satellite sequence on the long arm of chromosome 4qA or with a portion of this region of about 1 kb; or the region of about 750 bp which is located about 2.5 kb downstream of the telomeric end of said repeat array of a beta-satellite sequence on the long arm of chromosome 4qA or with a portion of this region of about 750 bp; or the region of about 13 kb which is located at least about 8.5 kb downstream of the telomeric end of said repeat array of a beta-satellite sequence on the long arm of chromosome 4qA; and/or (ii) the probe which is specific for the qB haplotype, the probe forming a signature specific for the qB haplotype or at least one probe of the set of probes forming a signature specific for the qB haplotype hybridizes with the totality of the region of about 6 kb which is immediately telomeric relatively to the D4Z4 tandem repeat array on the long arm of chromosome 4qB or with a portion of this region, said portion comprising at least 2 kb of this region.

23. The method according to claim 20, wherein the repeat probe or at least one of the repeat probes hybridizes, with the whole sequence of the D4Z4 repeat unit of a D4Z4 tandem repeat array or with a portion of the D4Z4 repeat unit of a D4Z4 tandem repeat array, wherein said portion is a portion consisting of about a half of said D4Z4 repeat unit or a portion located at one end of said D4Z4 repeat unit or close to one end of said D4Z4 repeat unit.

24. The method according to claim 23, wherein the repeat probe or at least one of the repeat probes hybridizes with the whole sequence of the D4Z4 repeat unit of a D4Z4 tandem repeat array, and wherein the number of repeat units in a D4Z4 tandem repeat array is determined by:

1) measuring, for this repeat array, the total length (L) of the hybridization signal that corresponds to the hybridized repeat probes; and 2) calculating the number (n) of D4Z4 repeat units of said D4Z4 repeat units using the ratio n=L/l, wherein l corresponds to the length of one D4Z4 repeat unit.

25. The method according to claim 24, wherein at least two different repeat probes are used, wherein (i) said repeat probes hybridize with distinct regions of the D4Z4 repeat unit in a D4D4 repeat array and/or (ii) one of said probes hybridizes with a region of the D4Z4 repeat unit which is included, totally or in part, in the region of the D4Z4 repeat unit which hybridizes with another of said probes.

26. The method according to claim 20, wherein the probe which is specific for chromosome 4, the probe forming a signature specific for chromosome 4 or the set of probes forming a signature specific for chromosome 4 comprises at least one probe comprising or consisting of:

i) a sequence chosen among sequences ranging from the following coordinates relative to the NCBI build 36.1 Human reference sequence: 191089412 to 19096843 (4q1 probe), 191106888 to 19116775 (4q2 probe), 191128570 to 19138567 (4q3 probe) and 191148576 to 19158554 (4q4 probe);

ii) a sequence complementary to sequence i);

iii) a sequence capable of hybridizing to sequence (i) or (ii) under stringent conditions;

iv) a nucleotide variant of sequence i); or v) a portion of any of sequences (i), (ii), (iii) or (iv), and/or the probe which is specific for chromosome 10, the probe forming a signature specific for chromosome 10 or the set of probes forming a signature specific for chromosome 10 comprises at least one probe comprising:

i) a sequence chosen among sequences ranging from the following coordinates relative to the NCBI build 36.1 Human reference sequence: 135247926 to 135252909 (10q1 probe), 135257958 to 135262966 (10q2 probe), 135267992 to 135272976 (10q3 probe), and 135278058 to 135282988 (10q4 probe);

ii) a sequence complementary to sequence i);
iii) a sequence capable of hybridizing to sequence (i) or (ii) under stringent conditions;
a nucleotide variant of sequence i); or
v) a portion of any of sequences (i), (ii), (iii) or (iv), and/or
the probe which is specific for the qA haplotype, the probe forming a signature specific for the qA haplotype or the set of probes forming a signature specific for the qA haplotype comprises or consists of at least one probe comprising:
i) a sequence chosen among sequences ranging from the following coordinates relative to the Genbank accession number U74496.1: 2756 to 3556 (qA1 probe) and 8723 to 10672 (qA2 probe);
ii) a sequence complementary to sequence i);
iii) a sequence capable of hybridizing to sequence (i) or (ii) under stringent conditions;
iv) a nucleotide variant of sequence i); or
v) a portion of any of sequences (i), (ii), (iii) or (iv), and/or
the probe which is specific for the qB haplotype, the probe forming a signature specific for the qB haplotype or at least one probe of the set of probes forming a signature specific for the qB haplotype comprises or consists of:
i) a sequence ranging from the following coordinates relative to the NCBI build 36.1 Human reference sequence: 191252023 to 19253372 (qB1-3 probe) and 191248879 to 19252040 (qB1-4 probe), or the unique probe formed of qB1-3 and qB1-4 resulting in qB1;
ii) a sequence complementary to sequence i);
iii) a sequence capable of hybridizing to sequence (i) or (ii) under stringent conditions;
a nucleotide variant of sequence i); or
v) a portion of any of sequences (i), (ii), (iii) or (iv), and/or
the repeat probe or at least one of the repeat probes consists of:
i) a sequence chosen among sequences ranging from the following coordinates relative to the Genbank accession number U85056.1: 24213 to 27507 (DeeZee probe), 24213 to 25948 (Dee probe) and 25763 to 27507 (Zee probe);
ii) a sequence complementary to sequence i);
iii) a sequence capable of hybridizing to sequence (i) or (ii) under stringent conditions;
iv) a nucleotide variant of sequence i); or
v) a portion of any of sequences (i), (ii), (iii) or (iv).

27. The method according to claim 26, wherein the mix of probes further includes at least one of the following probes, which are optionally labelled:
a probe or a set of probes hybridizing with the region of about 42 kb which is immediately centromeric relatively to the D4Z4 tandem repeat array on the long arm of chromosome 4 or with a portion of this region and/or hybridizing with the region of about 42 kb which is immediately centromeric relatively to the D4Z4 tandem repeat array on the long arm of chromosome 10 or with a portion of this region; and/or
a probe or a set of probes hybridizing with the region of about 15 kb which is immediately telomeric relatively to the D4Z4 tandem repeat array on chromosomes of the qA haplotype and/or on chromosomes of the qB haplotype or with a portion of this region.

28. The method according to claim 1, wherein at least two different repeat probes are used, wherein (i) said repeat probes hybridize with distinct regions of the D4Z4 repeat unit in a D4Z4 repeat array and/or (ii) one of said probes hybridizes with a region of the D4Z4 repeat unit which is included, totally or in part, in the region of the D4Z4 repeat unit which hybridizes with another of said probes.

29. The method according to claim 1, wherein the mix of probes further includes at least one of the following probes, which are optionally labelled:
a probe or a set of probes hybridizing with the region of about 42 kb which is immediately centromeric relatively to the D4Z4 tandem repeat array on the long arm of chromosome 4 or with a portion of this region and/or hybridizing with the region of about 42 kb which is immediately centromeric relatively to the D4Z4 tandem repeat array on the long arm of chromosome 10 or with a portion of this region; and/or
a probe or a set of probes hybridizing with the region of about 15 kb which is immediately telomeric relatively to the D4Z4 tandem repeat array on chromosomes of the qA haplotype and/or on chromosomes of the qB haplotype or with a portion of this region.

30. The method according to claim 1, consisting of the following steps:
a) providing a support on which a nucleic acid sample comprising nucleic acid representative of chromosomes has been previously stretched in linear and parallel strands and hybridizing said nucleic acid with the probes;
b) detecting the hybridization signals corresponding to the probes; and
c) analysing organization of D4Z4 tandem repeat arrays on nucleic acid representative of chromosomes and/or analysing methylation and/or analysing biochemical events in said D4Z4 tandem repeat arrays and/or in regions adjacent or essentially adjacent to said D4Z4 tandem repeat arrays.

31. The method according to claim 1, wherein said probe or set of probes which enable(s) to distinguish chromosome 4 (4q) from chromosome 10 (10q) are located at least 42 kb or 45 kb upstream of the repeat array.

32. The method according to claim 1, wherein said probe or set of probes which enable(s) to distinguish haplotype qA from haplotype qB comprises a 68-bp beta-satellite sequence and/or a $TTAGGG_n$ telomeric repeat.

33. The method according to claim 1, wherein said probe or set of probes called "repeat probe(s)", which is (are) specific for D4Z4 tandem repeat arrays, is labelled with a label that is different from any other label used to label the other probes.

34. The method according to claim 1, wherein said mix further comprises a probe hybridizing with the region extending over 42 kb upstream (centromeric) of the repeat array on both chromosomes 4 and 10.

35. A method for in vitro detecting of susceptibility to facioscapulohumeral muscular dystrophy (FSHD) in a patient, said method comprising analyzing D4Z4 tandem repeat arrays on nucleic acid representative of chromosomes in a genomic DNA sample obtained from said patient, by a method comprising a hybridization step of contacting nucleic acid representative of said chromosomes with a mix of at least the following probes:
a probe or a set of probes called "repeat probe(s)", which is (are) specific for D4Z4 tandem repeat arrays;
a probe or a set of probes which enable(s) to distinguish chromosome 4 (4q) from chromosome 10 (10q); and
a probe or a set of probes which enable(s) to distinguish haplotype qA from haplotype qB; and
optionally, a probe or a set of probes which enable(s) to distinguish chromosome Y from chromosome 4 and/or from chromosome 10, wherein said probes are optionally labelled, wherein either all the labelled probes being labelled with the same label(s) or at least one probe is labelled with one or more label(s) different from the label(s) of other probes, and wherein the detection of a repeat array from a 4qA allele with a number of D4Z4 repeat units equal to or lower than 12 is indicative of a susceptibility to FSHD.

36. The method according to claim 35, comprising of the following steps:
 a) providing a support on which a nucleic acid sample comprising nucleic acid representative of chromosomes has been previously stretched in linear and parallel strands and hybridizing said nucleic acid with the probes;
 b) detecting the hybridization signals corresponding to the probes; and
 c) analysing organization of D4Z4 tandem repeat arrays on nucleic acid representative of chromosomes and/or analysing methylation and/or analysing biochemical events in said D4Z4 tandem repeat arrays and/or in regions adjacent or essentially adjacent to said D4Z4 tandem repeat arrays.

37. The method according to claim 35, consisting of the following steps:
 a) providing a support on which a nucleic acid sample comprising nucleic acid representative of chromosomes has been previously stretched in linear and parallel strands and hybridizing said nucleic acid with the probes;
 b) detecting the hybridization signals corresponding to the probes; and
 c) analysing organization of D4Z4 tandem repeat arrays on nucleic acid representative of chromosomes and/or analysing methylation and/or analysing biochemical events in said D4Z4 tandem repeat arrays and/or in regions adjacent or essentially adjacent to said D4Z4 tandem repeat arrays.

38. The method according to claim 35, wherein said probe or set of probes which enable(s) to distinguish chromosome 4 (4q) from chromosome 10 (10q) are located at least 42 kb/45 kb upstream of the repeat array.

39. The method according to claim 35, wherein said probe or set of probes which enable(s) to distinguish haplotype qA from haplotype qB comprises a 68-bp beta-satellite sequence and/or a $TTAGGG_n$ telomeric repeat.

40. The method according to claim 35, wherein said probe or set of probes called "repeat probe(s)", which is (are) specific for D4Z4 tandem repeat arrays, is labelled with a label that is different from any other label used to label the other probes.

41. The method according to claim 35, wherein said mix further comprises a probe hybridizing with the region extending over 42 kb upstream (centromeric) of the repeat array on both chromosomes 4 and 10.

* * * * *

SEQUENCE LISTING

```
<160> NUMBER OF SEQ ID NOS: 2

<210> SEQ ID NO 1
<211> LENGTH: 1772
<212> TYPE: DNA
<213> ORGANISM: Artificial
<220> FEATURE:
<223> OTHER INFORMATION: probe with added restriction sites on
      extremities (20 nucleotides each)
<220> FEATURE:
<221> NAME/KEY: misc_feature
<222> LOCATION: (19)..(1754)
<223> OTHER INFORMATION: the Dee probe sequence

<400> SEQUENCE: 1
tctagaaagc ttgctagcgc gcgcctgggg ctctcccaca gggggctttc gtgagccagg      60
cagcgagggc cgccccgcg ctgcagccca gccaggccgc gccggcagag gggatctccc     120
aacctgcccc ggcgcgcggg gatttcgcct acgccgcccc ggctcctccg gagccggggc    180
gctctcccac cctcaggctc ctcggtggcc tccgcacccg ggcaaaagcc gggaggaccg    240
ggacccgcag cgcgacggcc tgccgggccc ctgcgcggtg gcacagcctg ggcccgctca    300
agcggggccg cagggccaag gggtgcttgc gccacccacg tcccagggga gtccgtggtg    360
gggctggggc cggggtcccc aggtcgccgg ggcggcgtgg gaacccaag ccggggcagc     420 tccacctccc cagcccgcgc ccccggacg cctccgcctc cgcgcggcag gggcagatgc     480
aaggcatccc ggcgccctcc caggcgctcc aggagccggc gccctggtct gcactcccct    540
gcggcctgct gctggatgag ctcctggcga gcccggagtt tctgcagcag gcgcaacctc    600
tcctagaaac ggaggccccg ggggagctgg aggcctcgga agaggcgcct cgctggaagc    660 accctcagc gaggaagaat accgggctct gctggaggag ctttaggacg cggggttggg     720
acggggtcgg gtggttcggg gcagggcggt ggcctctctt tcgcggggaa cacctggctg    780
gctacggagg ggcgtgtctc cgccccgccc cctccaccgg gctgaccggc ctgggattcc    840
tgccttctag gtccaggccg gtgagagact ccacaccgcg gagaactgcc attctttcct    900
gggcatcccg gggatcccag agccggccca ggtaccagca ggtgggccgc ctactgcgca    960
cgcgcgggtt tgcgggcagc cgcctgggct gtgggagcag cccgggcaga gctctcctgc   1020
ctctccacca gcccaccccg ccgcctgacc gcccatccc cacccccac ccccaccccc      1080 cggaaaacgc gtcgtcccct gggctgggtg gagacccccg tcccgcgaaa caccgggccc   1140
cgcgcagcgt ccgggcctga caccgctccg gcggctcgcc tcctcctgt cgccccggg     1200 ccaccgtcgc ccgccgcccg ggcccctgca gccgcccagc tgccagcacg gagcgcctgg   1260
cggcggaacg cagaccccag gcccggcgca caccgggacg ctgagcgttc caggcgggag   1320
```

| | |
|---|---|
| ggaaggcggg cagagatgga gagaggaacg ggagacctag aggggcggaa ggatgggcgg | 1380 |
| agggacgtta ggagggaggc agggaggcag ggaggcaggg aggaacggag ggagagacag | 1440 |
| agcgacgcag ggactggggg cgggcggag ggagccgggg acggacgggg ggaggaaggc | 1500 |
| agggaggaaa agcggtcctc ggcctccggg agtagcggga cccccgccct ccgggaaaac | 1560 |
| ggtcagcgtc cggcgcgggc tgagggctgg gcccacagcg gccgcgccgg ccggcggggc | 1620 |
| accacccatt cgccccggtt ccggggccca gggagtgggc ggtttcctcc gggacaaaag | 1680 |
| accggaattc gggttgccgt cgggttttca cccgcgcggt tcacagaccg cacatcccca | 1740 |
| ggctgagccc tgcactcgag aagcttccat gg | 1772 |

<210> SEQ ID NO 2
<211> LENGTH: 1781
<212> TYPE: DNA
<213> ORGANISM: Artificial
<220> FEATURE:
<223> OTHER INFORMATION: probe with added restriction sites on
      extremities (20 nucleotides each)
<220> FEATURE:
<221> NAME/KEY: misc_feature
<222> LOCATION: (19)..(1763)
<223> OTHER INFORMATION: The Zee probe sequence

<400> SEQUENCE: 2

| | |
|---|---|
| tctagaaagc ttgctagctc cggcgcgggc tgagggctgg gcccacagcg gccgcgccgg | 60 |
| ccggcgggc accacccatt cgccccggtt ccggggccca gggagtgggc ggtttcctcc | 120 |
| gggacaaaag accggaattc gggttgccgt cgggttttca cccgcgcggt tcacagaccg | 180 |
| cacatcccca ggctgagccc tgcaacgcgg cgcgaggccg acagaccgg ccacggagga | 240 |
| gccacacgca ggacgacgga ggcgtgattt tggtttccgc gtggctttgc cctccgcaag | 300 |
| gcggcctgtt gctcacgtct ctccggcccc cgaaaggctg gccatgccga ctgtttgctc | 360 |
| ccggagctct gcgggcaccc ggaaacatgc agggaagggt gcaagccggg catggtgcct | 420 |
| tcgctctcct tgccaggttc caaaccggcc acactgcaga ctcccccacg ttgccgcacg | 480 |
| cgggaatcca tcgtcaggcc atcacgccgg ggaggcatct cctctctggg gtctcgctct | 540 |
| ggtcttctac gtggaaatga acgagagcca cacgcctgcg tgtgcgagac cgtcccggca | 600 |
| acggcgacgc ccacaggcat tgcctccttc acggagagag ggcctggcac actcaagact | 660 |
| cccacggagg ttcagttcca cactcccctc caccctccca ggctggtttc tccctgctgc | 720 |
| cgacgcgtgg gagcccagag agcggcttcc cgttcccgcg ggatccctgg agaggtccgg | 780 |
| agagccggcc cccgaaacgc gccccccctcc cccctccccc ctctccccct tcctcttcgt | 840 |
| ctctccggcc ccaccaccac caccgccacc acgccctccc ccccccccc ccccccccac | 900 |
| caccaccacc ccgccggccg gccccaggcc tcgacgccct gggtcccttc cggggtgggg | 960 |
| cgggctgtcc caggggggct caccgccatt catgaagggg tggagcctgc ctgcctgtgg | 1020 |
| gcctttacaa gggcggctgg ctggctggct ggctgtccgg gcaggcctcc tggctgcacc | 1080 |
| tgccgcagtg cacagtccgg ctgaggtgca cgggagcccg ccggcctctc tctgcccgcg | 1140 |
| tccgtccgtg aaattccggc cggggctcac cgcgatggcc ctcccgacac cctcggacag | 1200 |
| caccctcccc gcggaagccc ggggacgagg acggcgacgg agactcgttt ggaccccgag | 1260 |
| ccaaagcgag gccctgcgag cctgctttga gcggaacccg tacccgggca tcgccaccag | 1320 |
| agaacggctg gcccaggcca tcggcattcc ggagcccagg gtccagattt ggtttcagaa | 1380 |
| tgagaggtca cgccagctga ggcagcaccg gcgggaatct cggccctggc ccgggagacg | 1440 |

-continued

```
cggcccgcca gaaggccggc gaaagcggac cgccgtcacc ggatcccaga ccgccctgct    1500
cctccgagcc tttgagaagg atcgctttcc aggcatcgcc gcccgggagg agctggccag    1560
agagacgggc ctcccggagt ccaggattca gatctggttt cagaatcgaa gggccaggca    1620
cccgggacag ggtggcaggg cgcccgcgca ggcaggcggc ctgtgcagcg cggcccccgg    1680
cgggggtcac cctgctccct cgtgggtcgc cttcgcccac accggcgagt ggggaacggg    1740
gcttcccgca ccgcacgtgc cctctcgaga agcttccatg g                       1781
```